(12) United States Patent
Park et al.

(10) Patent No.: US 10,251,707 B2
(45) Date of Patent: Apr. 9, 2019

(54) GENERATION OF A COMPUTERIZED BONE MODEL REPRESENTATIVE OF A PRE-DEGENERATED STATE AND USEABLE IN THE DESIGN AND MANUFACTURE OF ARTHROPLASTY DEVICES

(71) Applicant: Howmedica Osteonics Corporation, Mahwah, NJ (US)

(72) Inventors: Ilwhan Park, Walnut Creek, CA (US); Charlie W. Chi, Milpitas, CA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 0 days.

(21) Appl. No.: 15/477,952

(22) Filed: Apr. 3, 2017

(65) Prior Publication Data

US 2017/0202622 A1     Jul. 20, 2017

Related U.S. Application Data

(60) Continuation of application No. 13/923,093, filed on Jun. 20, 2013, now Pat. No. 9,646,113, which is a
(Continued)

(51) Int. Cl.
*A61B 17/15* (2006.01)
*A61B 34/10* (2016.01)
(Continued)

(52) U.S. Cl.
CPC ............. *A61B 34/10* (2016.02); *A61B 17/15* (2013.01); *A61B 17/154* (2013.01);
(Continued)

(58) Field of Classification Search
CPC ...................................................... A61B 34/10
See application file for complete search history.

(56) References Cited

U.S. PATENT DOCUMENTS 5,150,304 A    9/1992  Berchem
5,417,694 A    5/1995  Marik
(Continued)

OTHER PUBLICATIONS

3-D Doctor, www.3d-doctor.com, Able Software Corp. Accessed May 21, 2018.*
(Continued)

*Primary Examiner* — David W Bates
(74) *Attorney, Agent, or Firm* — Polsinelli PC

(57) ABSTRACT

A method of generating a computerized bone model representative of at least a portion of a patient bone in a pre-degenerated state. The method includes: generating at least one image of the patient bone in a degenerated state; identifying a reference portion associated with a generally non-degenerated portion of the patient bone; identifying a degenerated portion associated with a generally degenerated portion of the patient bone; and using information from at least one image associated with the reference portion to modify at least one aspect associated with at least one image associated the generally degenerated portion. The method may further include employing the computerized bone model representative of the at least a portion of the patient bone in the pre-degenerated state in defining manufacturing instructions for the manufacture of a customized arthroplasty jig.

14 Claims, 42 Drawing Sheets

Related U.S. Application Data division of application No. 12/111,924, filed on Apr. 29, 2008, now Pat. No. 8,480,679.

(51) Int. Cl.
| | |
|---|---|
| *A61F 5/00* | (2006.01) |
| *G16H 50/50* | (2018.01) |
| *G06F 19/00* | (2018.01) |
| *G06T 17/00* | (2006.01) |
| *G06F 17/50* | (2006.01) |

(52) U.S. Cl.
CPC .......... *A61B 17/155* (2013.01); *A61B 17/157* (2013.01); *A61F 5/00* (2013.01); *G06F 17/50* (2013.01); *G06F 19/00* (2013.01); *G06F 19/321* (2013.01); *G06T 17/00* (2013.01); *G16H 50/50* (2018.01); *A61B 2034/102* (2016.02); *A61B 2034/105* (2016.02); *A61B 2034/108* (2016.02)

(56) References Cited

U.S. PATENT DOCUMENTS

| | | | |
|---|---|---|---|
| 5,454,717 | A | 10/1995 | Andreiko |
| 5,735,856 | A | 4/1998 | McCue |
| 5,762,125 | A | 6/1998 | Mastrorio |
| 6,033,415 | A | 3/2000 | Mittelstadt |
| 6,757,582 | B2 | 6/2004 | Brisson et al. |
| 9,549,782 | B2 | 1/2017 | Park et al. |
| 9,636,120 | B2 | 5/2017 | Park |
| 2002/0055679 | A1 | 5/2002 | Sati |
| 2006/0093240 | A1 | 5/2006 | Sabuncu et al. |
| 2007/0038223 | A1 | 2/2007 | Marquart |
| 2007/0066917 | A1 | 3/2007 | Hodorek |
| 2007/0270680 | A1 | 11/2007 | Sheffer |
| 2008/0132783 | A1 | 6/2008 | Revie et al. |
| 2009/0089026 | A1 | 4/2009 | Rodriguez Y Baena |
| 2009/0264894 | A1 | 10/2009 | Wasielewski |
| 2011/0009868 | A1 | 1/2011 | Sato |
| 2016/0213491 | A1 | 7/2016 | Schoenefeld |
| 2016/0228194 | A1 | 8/2016 | Park et al. |
| 2016/0228195 | A1 | 8/2016 | Park et al. |
| 2016/0228196 | A1 | 8/2016 | Park et al. |
| 2016/0228197 | A1 | 8/2016 | Park et al. |
| 2016/0270857 | A1 | 9/2016 | Park et al. |
| 2016/0270858 | A1 | 9/2016 | Park et al. |
| 2016/0270859 | A1 | 9/2016 | Park et al. |
| 2016/0310217 | A1 | 10/2016 | Park et al. |
| 2017/0007275 | A1 | 1/2017 | Park et al. |
| 2017/0196642 | A1 | 7/2017 | Park |
| 2017/0209219 | A1 | 7/2017 | Park et al. |
| 2017/0209221 | A1 | 7/2017 | Park et al. |
| 2017/0367716 | A1 | 12/2017 | Park et al. |
| 2018/0000497 | A1 | 1/2018 | Park et al. |
| 2018/0014836 | A1 | 1/2018 | Park et al. |

OTHER PUBLICATIONS

TechniCom, Inc. SolidWorks 2006 Office Premium. Raymond Kurland. Jan. 2006. Accessed May 21, 2018.*
Appeal Brief, U.S. Appl. No. 11/946,002, dated Oct. 13, 2016.
Canadian Office Action, 2721735, dated Aug. 24, 2016.
Canadian Office Action, CA2642616, dated Jan. 12, 2017.
Canadian Office Action, CA2721762, dated Jul. 20, 2016.
Decision on Appeal, U.S. Appl. No. 11/642,385, dated Mar. 2, 2017.
EP Examination Report, EP13188389.4, dated Jan. 30, 2017.
Examiner's Answer in appeal, U.S. Appl. No. 11/946,002, dated Jan. 23, 2017.
Extended European Search Report, EP11769533.8, dated Jan. 9, 2017.
Final Office Action, U.S. Appl. No. 14/084,255, dated Jul. 26, 2016.
Final Office Action, U.S. Appl. No. 14/869,762, dated Oct. 6, 2016.
Indian Examination Report, 673/KOLNP/2011, dated Jun. 29, 2017.
International Search Report and Written Opinion, PCT/US2016/034847, dated Dec. 8, 2016.
Non-Final Office Action, U.S. Appl. No. 14/335,460, dated Aug. 30, 2016.
Non-Final Office Action, U.S. Appl. No. 14/084,255, dated Jan. 19, 2017.
Non-Final Office Action, U.S. Appl. No. 14/086,878, dated Nov. 10, 2016.
Non-Final Office Action, U.S. Appl. No. 14/272,147, dated Jun. 17, 2016.
Non-Final Office Action, U.S. Appl. No. 14/335,431, dated Sep. 14, 2016.
Non-Final Office Action, U.S. Appl. No. 14/928,767, dated Jan. 12, 2017.
Non-Final Office Action, U.S. Appl. No. 14/946,106, dated Jun. 23, 2016.
Non-Final Office Action, U.S. Appl. No. 15/168,359, dated Dec. 30, 2016.
Non-Final Office Action, U.S. Appl. No. 15/168,359, dated Aug. 17, 2016.
Non-Final Office Action, U.S. Appl. No. 15/168,405, dated Jan. 12, 2017.
Non-Final Office Action, U.S. Appl. No. 15/168,405, dated Aug. 3, 2016.
Non-Final Office Action, U.S. Appl. No. 15/274,717, dated Apr. 26, 2017.
Notice of Allowance, U.S. Appl. No. 11/642,385, dated Jun. 16, 2017.
Notice of Allowance, U.S. Appl. No. 14/011,998, dated Jan. 11, 2017.
Notice of Allowance, U.S. Appl. No. 14/084,255, dated Jun. 8, 2017.
Notice of Allowance, U.S. Appl. No. 14/086,849, dated Jun. 6, 2017.
Notice of Allowance, U.S. Appl. No. 14/086,878, dated Jun. 14, 2017.
Notice of Allowance, U.S. Appl. No. 14/272,147, dated Nov. 21, 2016.
Notice of Allowance, U.S. Appl. No. 14/335,431, dated May 10, 2017.
Notice of Allowance, U.S. Appl. No. 14/335,460, dated Mar. 27, 2017.
Notice of Allowance, U.S. Appl. No. 14/946,106, dated Feb. 3, 2017.
Notice of Allowance, U.S. Appl. No. 15/167,614, dated Aug. 26, 2016.
Notice of Allowance, U.S. Appl. No. 15/168,359, dated Jul. 14, 2017.
Notice of Allowance, U.S. Appl. No. 15/168,405, dated Jun. 7, 2017.
Notice of Allowance, U.S. Appl. No. 15/195,639, dated Jul. 12, 2017.
Notice of Allowance, U.S. Appl. No. 15/242,312, dated Jan. 3, 2017.
Preliminary Amendment, U.S. Appl. No. 15/202,417, dated Sep. 15, 2016.
Response to Final Office Action, U.S. Appl. No. 14/084,255, dated Dec. 22, 2016.
Response to Final Office Action, U.S. Appl. No. 14/869,762, dated Jan. 4, 2017.
Response to Non-Final Office Action, U.S. Appl. No. 14/084,255, dated Apr. 19, 2017.
Response to Non-Final Office Action, U.S. Appl. No. 14/084,255, dated May 23, 2016.
Response to Non-Final Office Action, U.S. Appl. No. 14/086,849, dated Apr. 3, 2017.
Response to Non-Final Office Action, U.S. Appl. No. 14/086,878, dated Apr. 4, 2017.
Response to Non-Final Office Action, U.S. Appl. No. 14/272,147, dated Sep. 13, 2016.
Response to Non-Final Office Action, U.S. Appl. No. 14/335,460, dated Jan. 27, 2017.

(56) References Cited

OTHER PUBLICATIONS

Response to Non-Final Office Action, U.S. Appl. No. 14/869,762, dated Jun. 29, 2016.
Response to Non-Final Office Action, U.S. Appl. No. 14/928,767, dated Apr. 12, 2017.
Response to Non-Final Office Action, U.S. Appl. No. 15/168,359, dated Oct. 24, 2016.
Response to Non-Final Office Action, U.S. Appl. No. 15/168,359, dated Mar. 30, 2017.
Response to Non-Final Office Action, U.S. Appl. No. 15/168,405 dated Oct. 31, 2016.
Response to Non-Final Office Action, U.S. Appl. No. 15/168,405, dated Apr. 7, 2017.
Response to Non-Final Office Action, U.S. Appl. No. 15/274,717, dated Jul. 17, 2017.
Response to Restriction, U.S. Appl. No. 14/335,431, dated Aug. 31, 2016.
Response to Restriction, U.S. Appl. No. 15/274,717, dated Jan. 9, 2017.
Restriction Requirement, U.S. Appl. No. 14/335,431, dated Aug. 12, 2016.
Restriction Requirement, U.S. Appl. No. 15/274,717, dated Nov. 16, 2016.
Supplemental Amendment, U.S. Appl. No. 14/869,762, dated Jan. 13, 2017.
Canadian Office Action, CA2642616, dated Jan. 9, 2018.
EP Examination Report, EP13188389.4, dated Jan. 8, 2018.
EP Search Report, EP17183082.1, dated Oct. 10, 2017.
Final Office Action, U.S. Appl. No. 15/274,717 dated Aug. 18, 2017.
Indian Examination Report, 3927/KOLNP/2010, dated Nov. 17, 2017.
International Search Report and Written Opinion, PCT/US2017/049466, dated Dec. 11, 2017.
Non-Final Office Action, U.S. Appl. No. 14/869,762, dated Sep. 11, 2017.
Non-Final Office Action, U.S. Appl. No. 14/928,767, dated Nov. 9, 2017.
Non-Final Office Action, U.S. Appl. No. 15/167,710, dated Nov. 3, 2017.
Non-Final Office Action, U.S. Appl. No. 15/274,717, dated Feb. 23, 2018.
Non-Final Office Action, U.S. Appl. No. 15/483,560, dated Sep. 28, 2017.
Non-Final Office Action, U.S. Appl. No. 15/701,180, dated Nov. 9, 2017.
Notice of Allowance, U.S. Appl. No. 15/202,417, dated Oct. 12, 2017.
Notice of Allowance, U.S. Appl. No. 15/469,171, dated Aug. 7, 2017.
Response to Final Office Action, U.S. Appl. No. 15/274,717, dated Nov. 13, 2017.
Response to Non-Final Office Action, U.S. Appl. No. 14/928,767, dated Mar. 6, 2018.
Response to Non-Final Office Action, U.S. Appl. No. 15/167,710, dated Feb. 2, 2018.
Response to Non-Final Office Action, U.S. Appl. No. 15/483,560, dated Feb. 19, 2018.
Response to Non-Final Office Action, U.S. Appl. No. 15/701,180, dated Feb. 9, 2018.
Response to Restriction, U.S. Appl. No. 14/928,767, dated Aug. 22, 2017.
Response to Restriction, U.S. Appl. No. 15/703,519, dated Feb. 19, 2018.
Restriction Requirement, U.S. Appl. No. 14/928,767, dated Jul. 28, 2017.
Restriction Requirement, U.S. Appl. No. 15/178,065, dated Jul. 31, 2017.
Restriction Requirement, U.S. Appl. No. 15/703,519, dated Dec. 18, 2017.

* cited by examiner

GENERATE 2D IMAGES 16 OF PATIENT'S JOINT 14 VIA MEDICAL IMAGING.
[BLOCK 100]

IDENTIFY A POINT P IN THE IMAGES 16 THAT IS AT THE APPROXIMATE MEDIAL-LATERAL AND ANTERIOR-POSTERIOR CENTER OF THE PATIENT'S KNEE JOINT 14.
[BLOCK 105]

CONTINUED IN [BLOCK 130] IN FIG.1D

CONTINUED IN [BLOCK 110] IN FIG.1C

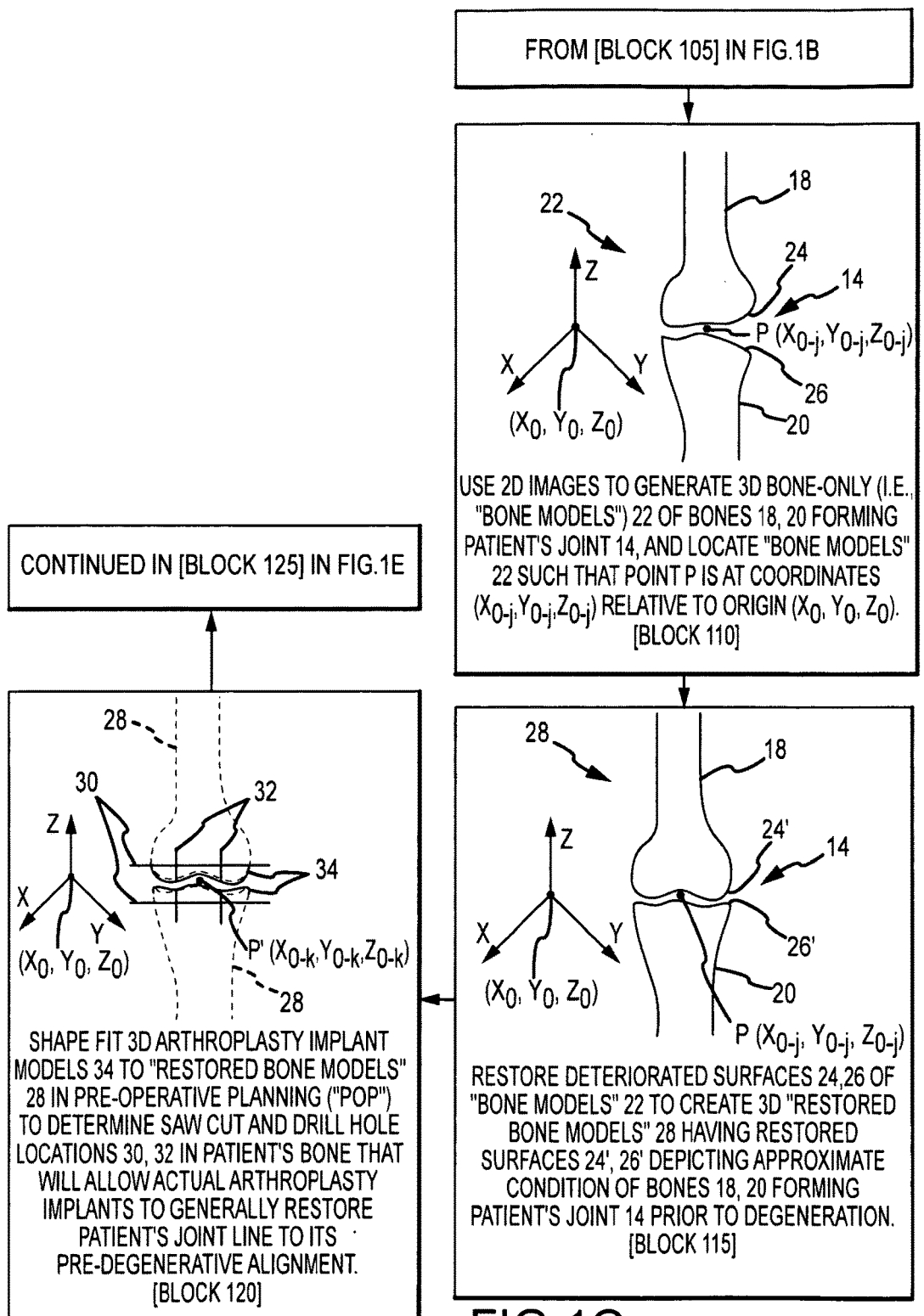

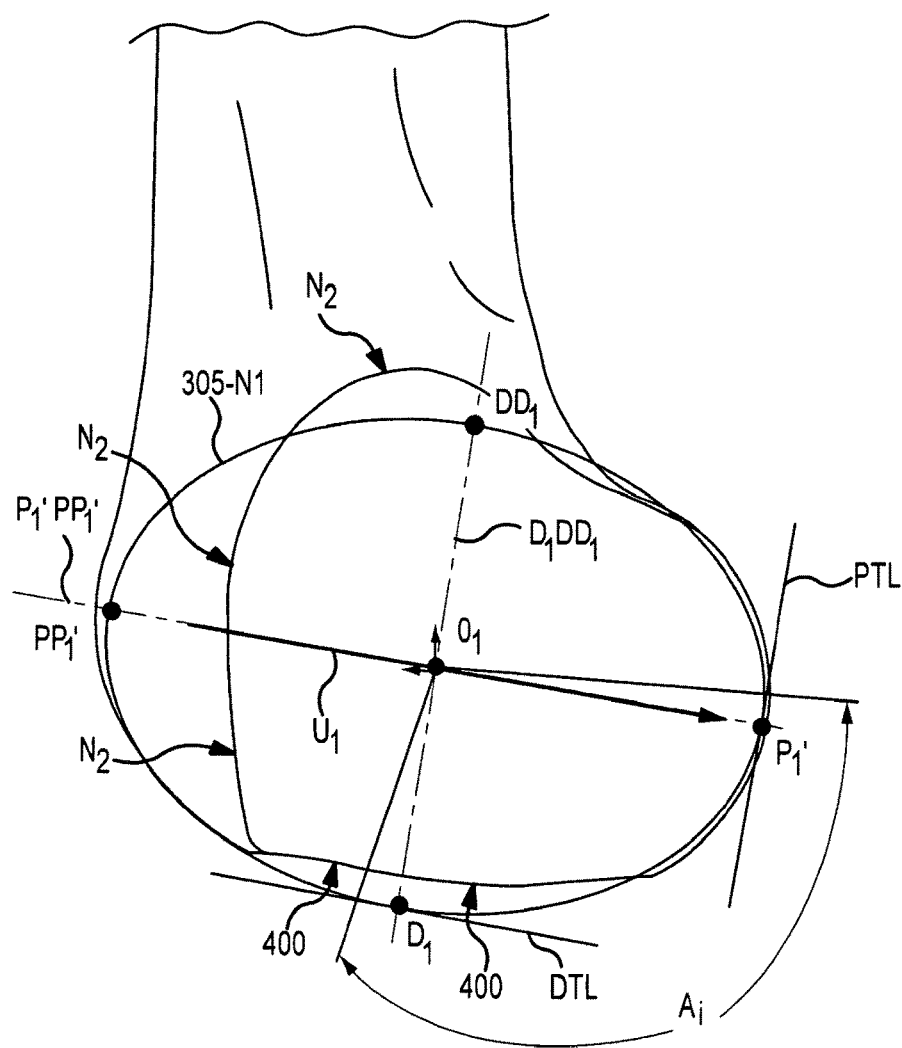
FIG.5C1

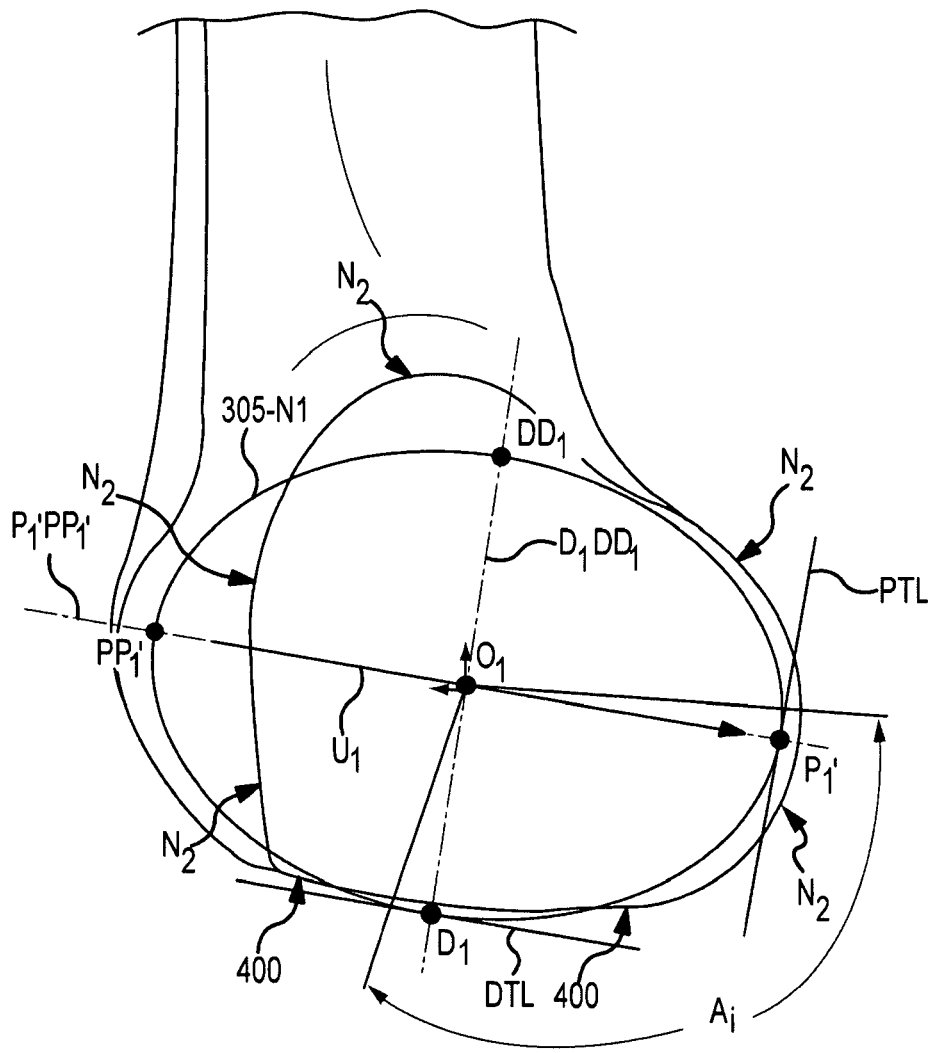
FIG.5C2

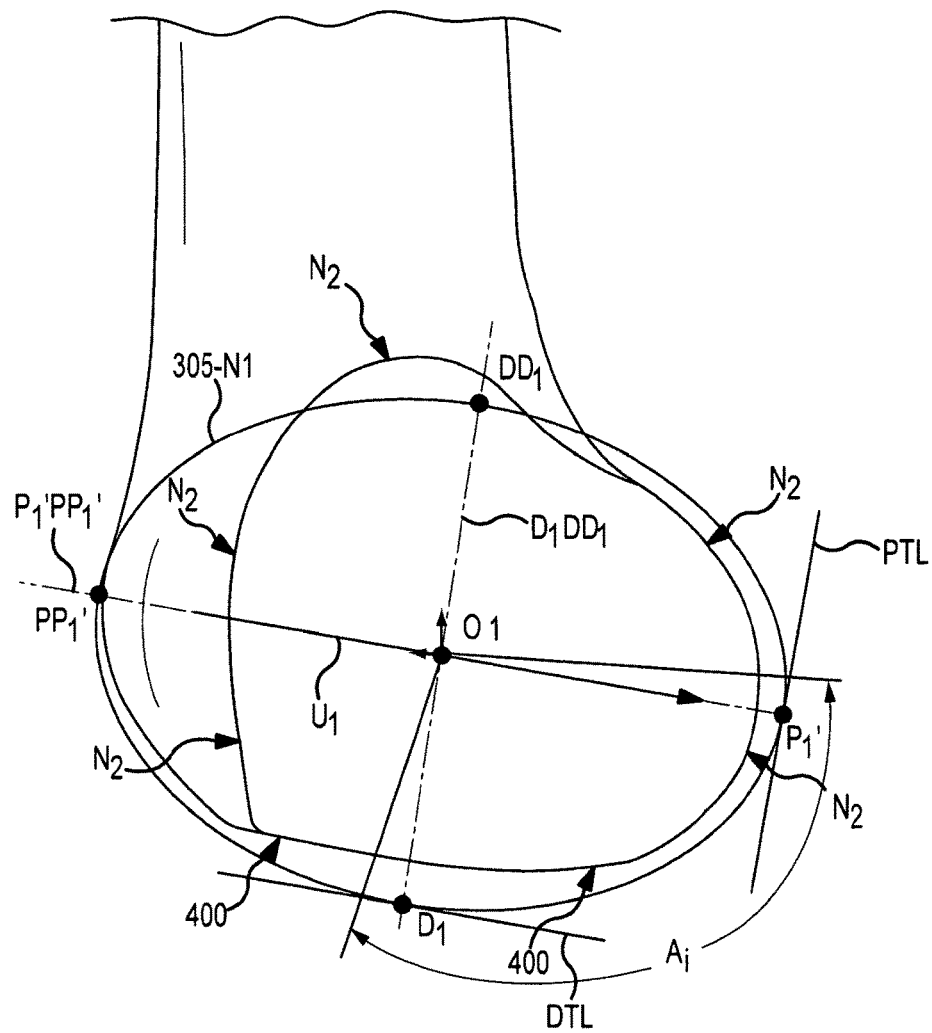
FIG.5C3

OSTEO ARTHRITIS KNEE BONE DAMAGE CRITERIA

| MEDIAL KNEE | | | LATERAL KNEE | | | RESTORATION (YES/NO) |
|---|---|---|---|---|---|---|
| SEVERE | MEDIUM | LIGHT | SEVERE | MEDIUM | LIGHT | |
|  |  | X |  |  | X | YES |
|  |  | X |  | X |  | YES |
|  |  | X | X |  |  | YES |
|  | X |  |  |  | X | YES |
|  | X |  |  | X |  | YES |
|  | X |  | X |  |  | NO |
| X |  |  |  |  | X | YES |
| X |  |  |  | X |  | NO |
| X |  |  | X |  |  | NO |

LIGHT: NO BONE DAMAGE OR BONE DAMAGE <<1mm
MEDIUM: BONE DAMAGE≈1mm
SEVERE: BONE DAMAGE >>1mm

FIG.7

GENERATION OF A COMPUTERIZED BONE MODEL REPRESENTATIVE OF A PRE-DEGENERATED STATE AND USEABLE IN THE DESIGN AND MANUFACTURE OF ARTHROPLASTY DEVICES

CROSS REFERENCE TO RELATED APPLICATIONS

The present application is a continuation application of U.S. application Ser. No. 13/923,093 filed Jun. 20, 2013, which application is a divisional application of U.S. application Ser. No. 12/111,924 filed Apr. 29, 2008, now U.S. Pat. No. 8,480,679, which application is hereby incorporated by reference in its entirety.

FIELD OF THE INVENTION

The present invention relates to systems and methods for manufacturing customized surgical devices. More specifically, the present invention relates to automated systems and methods for manufacturing customized arthroplasty jigs.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state. However, the system and method for generating the customized jigs often relies on a human to "eyeball" bone models on a computer screen to determine configurations needed for the generation of the customized jigs. This is "eyeballing" or manual manipulation of the bone models on the computer screen is inefficient and unnecessarily raises the time, manpower and costs associated with producing the customized arthroplasty jigs. Furthermore, a less manual approach may improve the accuracy of the resulting jigs.

There is a need in the art for a system and method for reducing the labor associated with generating customized arthroplasty jigs. There is also a need in the art for a system and method for increasing the accuracy of customized arthroplasty jigs.

SUMMARY

Preoperative assessment of bone loss is advantageous for prosthesis design, for example, to reduce the likelihood of prosthesis loosening and to provide a more reliable bone restoration method for preoperative implant design, thereby improving the success rate for such procedures such as total knee arthroplasty ("TKA") and partial knee arthroplasty (e.g., a unicompartment knee arthroplasty) and providing a patient-specific bone restoration method to fit an individual patient's knee features.

The current available joint reconstruction and replacement surgeries, including knee, ankle, hip, shoulder or elbow arthroplasty, are mainly based on standard guidelines and methods for acceptable performance. Taking this into account, the positioning and orientation of the arthroplasty work on a joint is based on standard values for orientation relative to the biomechanical axes, such as flexion/extension, varus/valgus, and range of motion.

One of the surgical goals of joint replacement/reconstruction should be to achieve a certain alignment relative to a load axes. However, the conventional standards are based on static load analysis and therefore may not be able to provide an optimal joint functionality for adopting individual knee features of OA patients. The methods disclosed herein provide a kinetic approach for bone restoration, properly balancing the unconstrained joint and ligaments surrounding the joint, and resulting in a placement of a prosthetic implant that generally restores the patient's knee to a generally pre-degenerated state.

In one embodiment, the result of the bone restoration process disclosed herein is a TKA or partial knee arthroplasty procedure that generally returns the knee to its pre-degenerated state whether that pre-degenerated state is naturally varus, valgus or neutral. In other words, if the patient's knee was naturally varus, valgus or neutral prior to degenerating, the surgical procedure will result in a knee that is generally restored to that specific natural pre-degenerated alignment, as opposed to simply making the knee have an alignment that corresponds to the mechanical axis, as is the common focus and result of most, if not all, arthroplasty procedures known in the art.

Disclosed herein is a method of generating a restored bone model representative of at least a portion of a patient bone in a pre-degenerated state. In one embodiment, the method includes: determining reference information from a reference portion of a degenerated bone model representative of the at least a portion of the patient bone in a degenerated state; and using the reference information to restore a degenerated portion of the degenerated bone model into a restored portion representative of the degenerated portion in the pre-degenerated state. In one embodiment, the method further includes employing the restored bone model in defining manufacturing instructions for the manufacture of a customized arthroplasty jig.

Also disclosed herein is a customized arthroplasty jig manufactured according to the above-described method. In one embodiment, the customized arthroplasty jig is configured to facilitate a prosthetic implant restoring a patient joint to a natural alignment. The prosthetic implant may be for a total joint replacement or partial joint replacement. The patient joint may be a variety of joints, including, but not limited to, a knee joint.

Disclosed herein is a method of generating a computerized bone model representative of at least a portion of a patient bone in a pre-degenerated state. In one embodiment, the method includes: generating at least one image of the patient bone in a degenerated state; identifying a reference portion associated with a generally non-degenerated portion of the patient bone; identifying a degenerated portion associated with a generally degenerated portion of the patient bone; and using information from at least one image associated with the reference portion to modify at least one aspect associated with at least one image associated the generally degenerated portion. In one embodiment, the method may further include employing the computerized bone model representative of the at least a portion of the patient bone in the pre-degenerated state in defining manufacturing instructions for the manufacture of a customized arthroplasty jig.

Also disclosed herein is a customized arthroplasty jig manufactured according to the above-described method. In one embodiment, the customized arthroplasty jig is configured to facilitate a prosthetic implant restoring a patient joint to a natural alignment. The prosthetic implant may be for a total joint replacement or partial joint replacement. The patient joint may be a variety of joints, including, but not limited to, a knee joint.

Disclosed herein is a method of generating a computerized bone model representative of at least a portion of a first patient bone in a pre-degenerated state. In one embodiment, the method includes: generating at least one image of the first patient bone in a degenerated state; identifying a reference portion associated with a generally non-degenerated portion of a second patient bone; identifying a degenerated portion associated with a generally degenerated portion of the first patient bone; and using information from at least one image associated with the reference portion to modify at least one aspect associated with at least one image associated the generally degenerated portion. In one embodiment, the method may further include employing the computerized bone model representative of the at least a portion of the first patient bone in the pre-degenerated state in defining manufacturing instructions for the manufacture of a customized arthroplasty jig.

Also disclosed herein is a customized arthroplasty jig manufactured according to the above-described method. In one embodiment, the customized arthroplasty jig is configured to facilitate a prosthetic implant restoring a patient joint to a natural alignment. The prosthetic implant may be for a total joint replacement or partial joint replacement. The patient joint may be a variety of joints, including, but not limited to, a knee joint.

Disclosed herein is a method of generating a computerized bone model representative of at least a portion of a first patient bone in a pre-degenerated state, wherein the first patient bone is part of a first patient joint. In one embodiment, the method includes: identifying a second patient bone of a second joint, wherein the second bone is a generally symmetrical mirror image of the first patient bone; generating a plurality of images of the second patient bone when the second patient bone is in a generally non-degenerated state; mirroring the plurality of images to reverse the order of the plurality images; and compiling the plurality of images in the reversed order to form the computerized bone model representative of the at least a portion of the first patient bone. In one embodiment, the method may further include employing the computerized bone model representative of the at least a portion of the first patient bone in the pre-degenerated state in defining manufacturing instructions for the manufacture of a customized arthroplasty jig.

Also disclosed herein is a customized arthroplasty jig manufactured according to the above-described method. In one embodiment, the customized arthroplasty jig is configured to facilitate a prosthetic implant restoring a patient joint to a natural alignment. The prosthetic implant may be for a total joint replacement or partial joint replacement. The patient joint may be a variety of joints, including, but not limited to, a knee joint.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 1B-1E are flow chart diagrams outlining the jig production method disclosed herein.

FIG. 5C1 is an N2 image slice of the medial condyle as taken along the N2 line in FIG. 5A.

FIG. 5C2 is the same view as FIG. 5C1, except illustrating the need to increase the size of the reference information prior to restoring the contour line of the N2 image slice.

FIG. 5C3 is the same view as FIG. 5C1, except illustrating the need to reduce the size of the reference information prior to restoring the contour line of the N2 image slice.

FIG. 7 is a table illustrating how OA knee conditions may impact the likelihood of successful bone restoration.

DETAILED DESCRIPTION

Figure 1A:
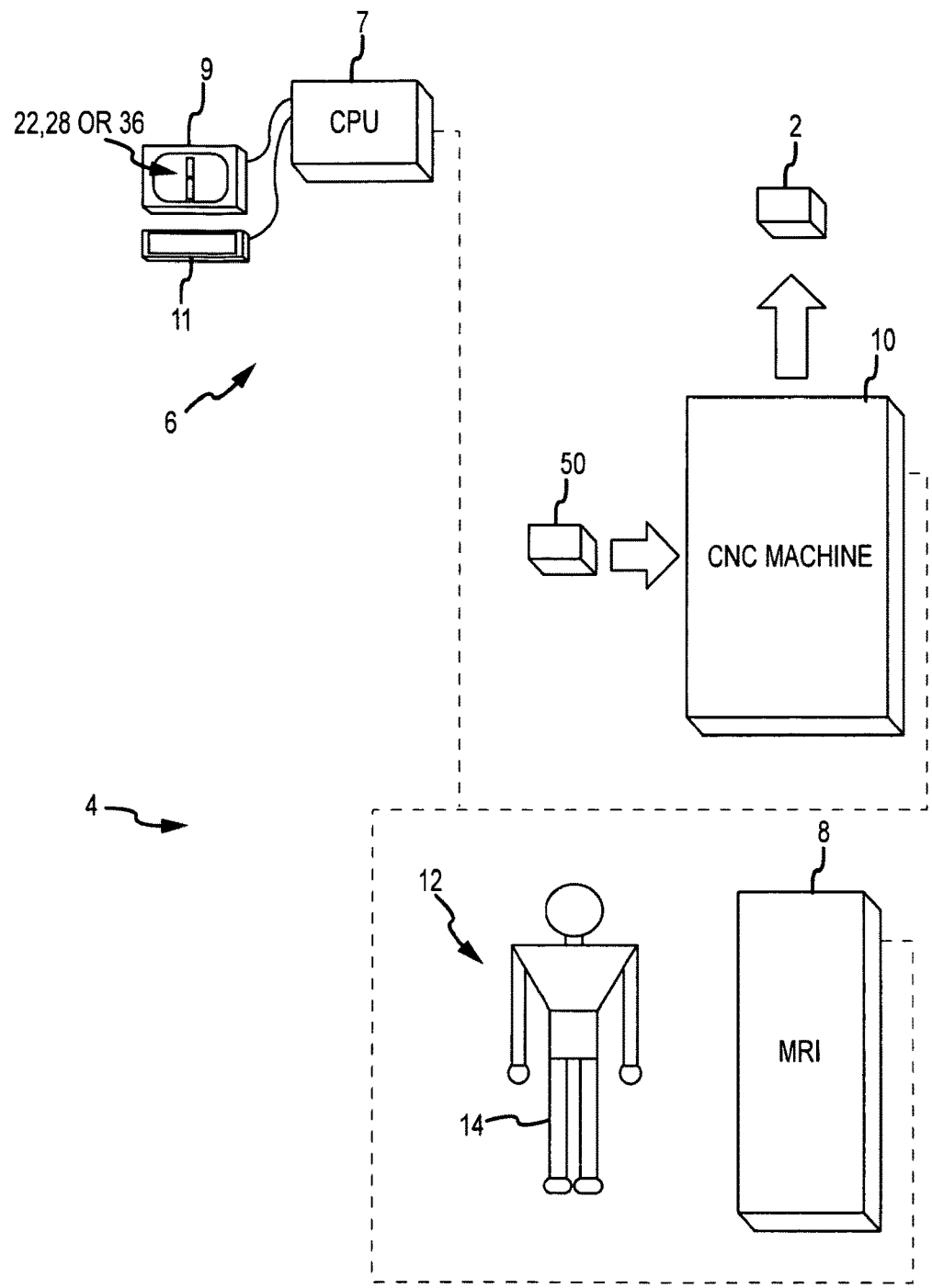
FIG. 1A is a schematic diagram of a system for employing the automated jig production method disclosed herein.

Disclosed herein are customized arthroplasty jigs 2 and systems 4 for, and methods of, producing such jigs 2. The jigs 2 are customized to fit specific bone surfaces of specific patients. Depending on the embodiment and to a greater or lesser extent, the jigs 2 are automatically planned and generated and may be similar to those disclosed in these three U.S. patent applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. patent applications are incorporated by reference in their entireties into this Detailed Description.

a. Overview of System and Method for Manufacturing Customized Arthroplasty Cutting Jigs For an overview discussion of the systems 4 for, and methods of, producing the customized arthroplasty jigs 2, reference is made to FIGS. 1A-1E. FIG. 1A is a schematic diagram of a system 4 for employing the automated jig production method disclosed herein. FIGS. 1B-1E are flow chart diagrams outlining the jig production method disclosed herein. The following overview discussion can be broken down into three sections.

The first section, which is discussed with respect to FIG. 1A and [blocks 100-125] of FIGS. 1B-1E, pertains to an example method of determining, in a three-dimensional ("3D") computer model environment, saw cut and drill hole locations 30, 32 relative to 3D computer models that are termed restored bone models 28. The resulting "saw cut and drill hole data" 44 is referenced to the restored bone models 28 to provide saw cuts and drill holes that will allow arthroplasty implants to generally restore the patient's joint to its pre-degenerated state. In other words, the patient's joint will be restored to its natural alignment prior to degeneration. Thus, where the patient's pre-degenerated joint had a certain degree of valgus, the saw cuts and drill holes will allow the arthroplasty implants to generally restore the patient's joint to that degree of valgus. Similarly, where the patient's pre-degenerated joint had a certain degree of varus, the saw cuts and drill holes will allow the arthroplasty implants to generally restore the patient's joint to that degree of varus, and where the patient's pre-degenerated joint was neutral, the saw cuts and drill holes will allow the arthroplasty implants to generally restore the patient's joint to neutral.

The second section, which is discussed with respect to FIG. 1A and [blocks 100-105 and 130-145] of FIGS. 1B-1E, pertains to an example method of importing into 3D computer generated jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

Figure 1B:
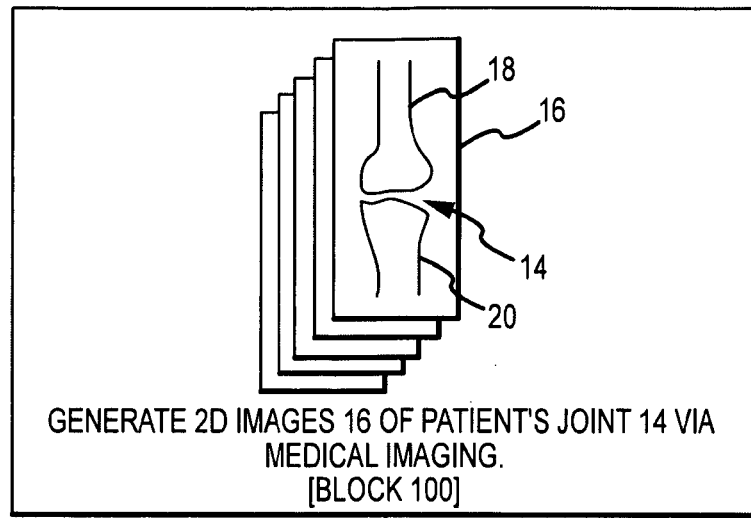
Figure 1B:
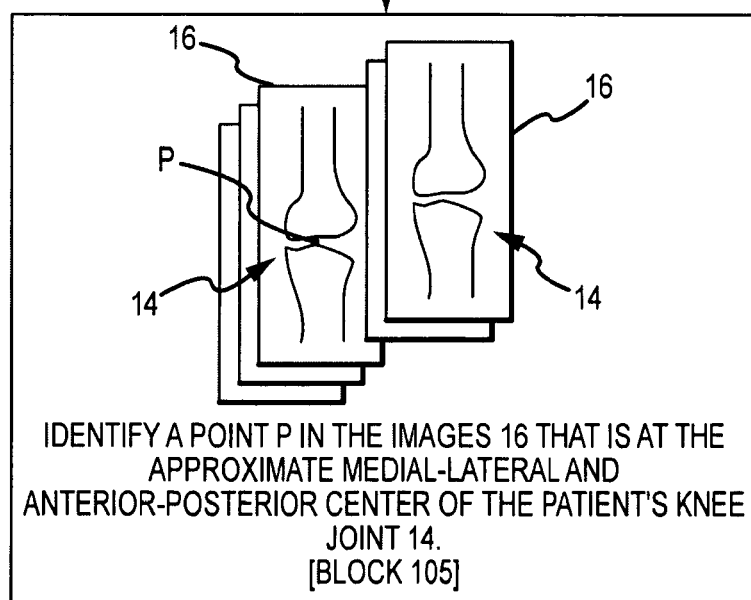
Figure 1D:
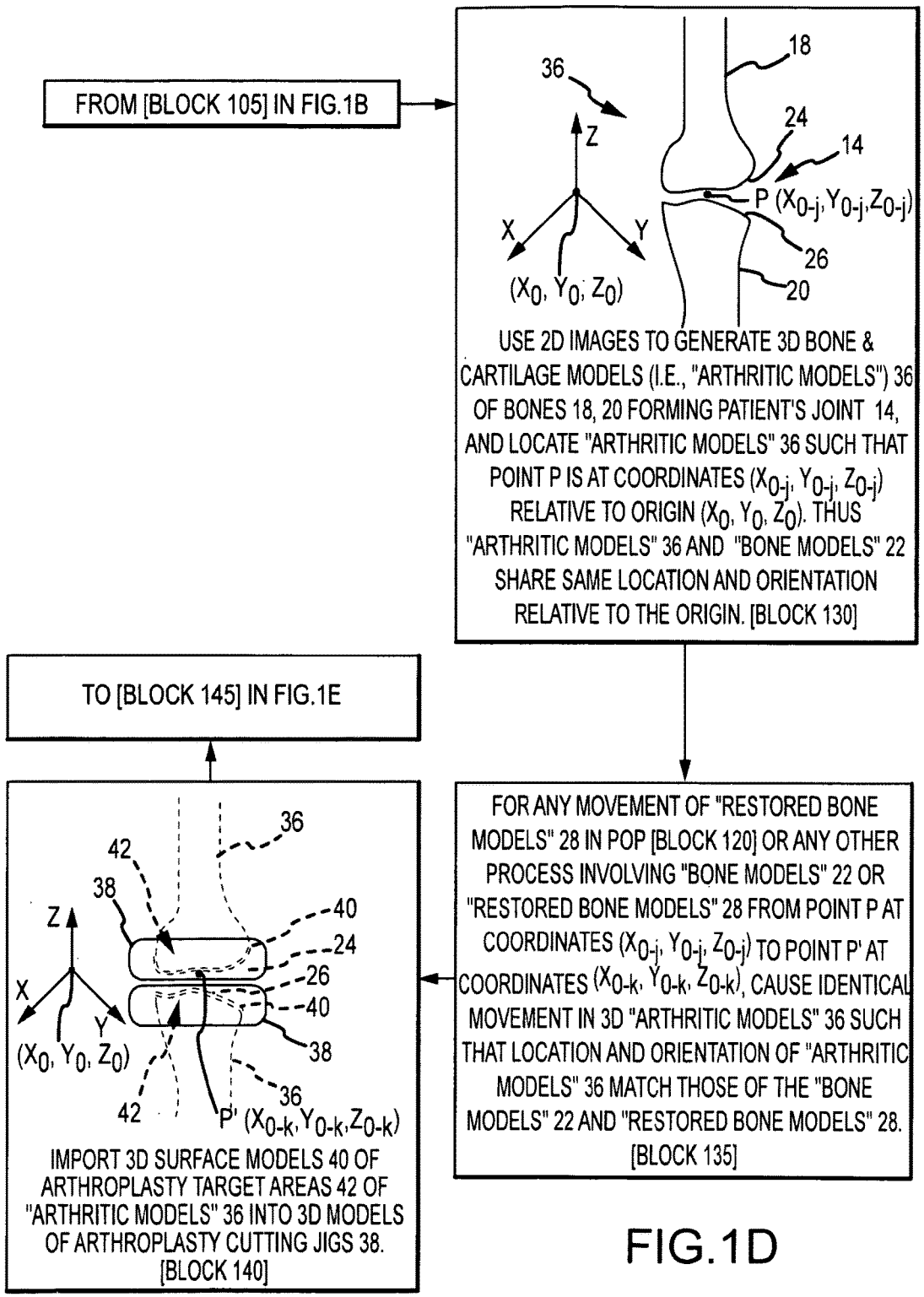
Figure 1E:
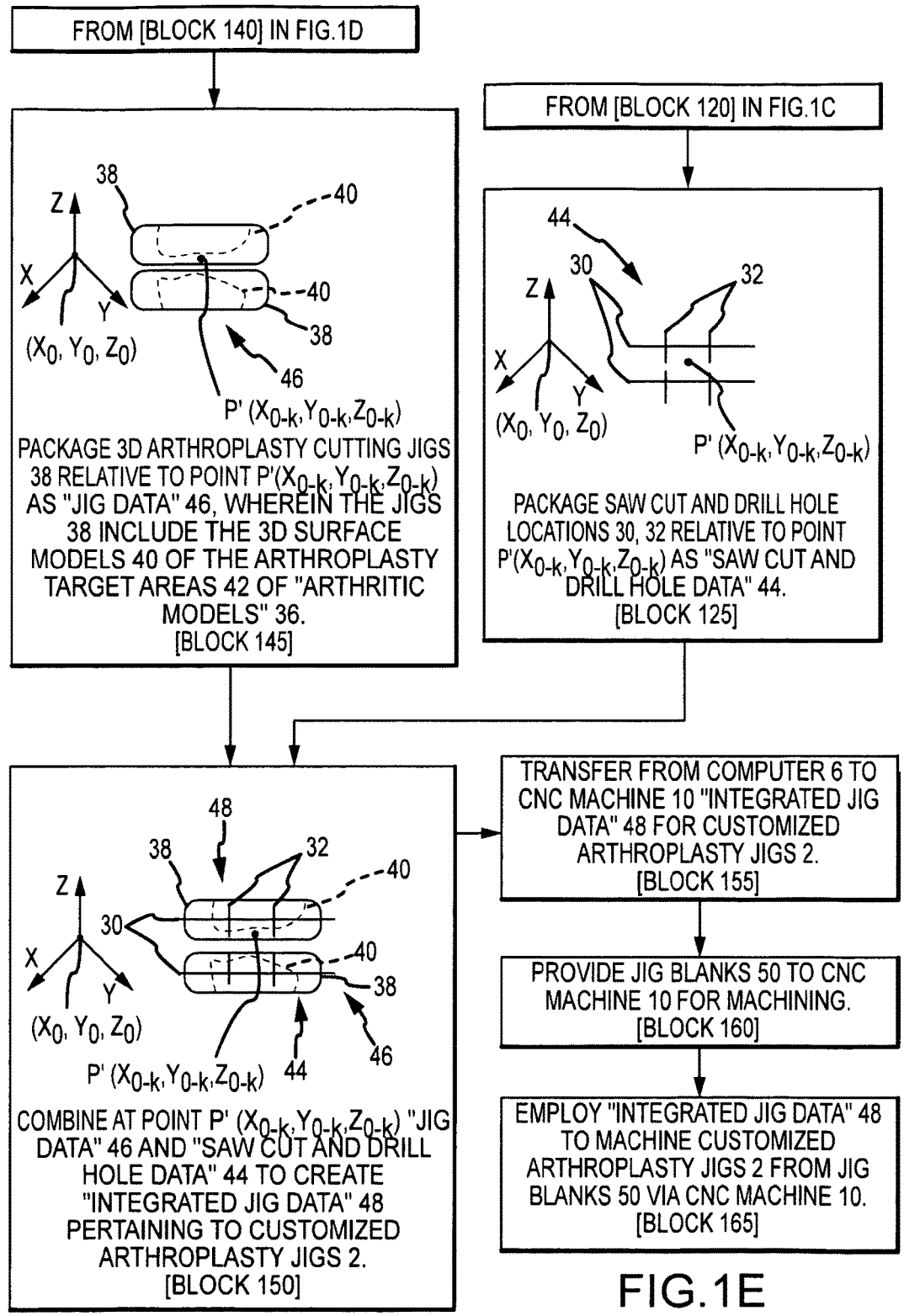

The third section, which is discussed with respect to FIG. 1A and [blocks 150-165] of FIG. 1E, pertains to a method of combining or integrating the "saw cut and drill hole data" 44 with the "jig data" 46 to result in "integrated jig data" 48. The "integrated jig data" 48 is provided to the CNC machine 10 for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated state. In other words, the customized arthroplasty jigs 2 facilitate preparing the patient's bone in a manner that allows the arthroplasty joint implants to restore the patient's joint to a natural alignment that corresponds to the patient's specific pre-degenerated alignment, whether that specific pre-degenerated alignment was valgus, varus or neutral.

As shown in FIG. 1A, the system 4 includes a computer 6 having a CPU 7, a monitor or screen 9 and an operator interface controls 11. The computer 6 is linked to a medical imaging system 8, such as a CT or MRI machine 8, and a computer controlled machining system 10, such as a CNC milling machine 10.

As indicated in FIG. 1A, a patient 12 has a joint 14 (e.g., a knee, elbow, ankle, wrist, hip, shoulder, skull/vertebrae or vertebrae/vertebrae interface, etc.) to be totally replaced (e.g., TKA), partially replaced (e.g., partial or compartmentalized replacement), resurfaced, or otherwise treated. The patient 12 has the joint 14 scanned in the imaging machine 8. The imaging machine 8 makes a plurality of scans of the joint 14, wherein each scan pertains to a thin slice of the joint 14.

As can be understood from FIG. 1B, the plurality of scans is used to generate a plurality of two-dimensional ("2D") images 16 of the joint 14 [block 100]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description.

As can be understood from FIG. 1A, the 2D images are sent to the computer 6 for creating computer generated 3D models. As indicated in FIG. 1B, in one embodiment, point P is identified in the 2D images 16 [block 105]. In one embodiment, as indicated in [block 105] of FIG. 1A, point P may be at the approximate medial-lateral and anterior-posterior center of the patient's joint 14. In other embodiments, point P may be at any other location in the 2D images 16, including anywhere on, near or away from the bones 18, 20 or the joint 14 formed by the bones 18, 20.

As described later in this overview, point P may be used to locate the computer generated 3D models 22, 28, 36 created from the 2D images 16 and to integrate information generated via the 3D models. Depending on the embodiment, point P, which serves as a position and/or orientation reference, may be a single point, two points, three points, a point plus a plane, a vector, etc., so long as the reference P can be used to position and/or orient the 3D models 22, 28, 36 generated via the 2D images 16.

As shown in FIG. 1C, the 2D images 16 are employed to create computer generated 3D bone-only (i.e., "bone models") 22 of the bones 18, 20 forming the patient's joint 14 [block 110]. The bone models 22 are located such that point P is at coordinates $(X_{0-j}, Y_{0-j}, Z_{0-j})$ relative to an origin $(X_0, Y_0, Z_0)$ of an X-Y-Z axis [block 110]. The bone models 22 depict the bones 18, 20 in the present deteriorated condition with their respective degenerated joint surfaces 24, 26, which may be a result of osteoarthritis, injury, a combination thereof, etc.

Computer programs for creating the 3D computer generated bone models 22 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

As indicated in FIG. 1C, the 3D computer generated bone models 22 are utilized to create 3D computer generated "restored bone models" or "planning bone models" 28 wherein the degenerated surfaces 24, 26 are modified or restored to approximately their respective conditions prior to degeneration [block 115]. Thus, the bones 18, 20 of the restored bone models 28 are reflected in approximately their condition prior to degeneration. The restored bone models 28 are located such that point P is at coordinates $(X_{0-j}, Y_{0-j}, Z_{0-j})$ relative to the origin $(X_0, Y_0, Z_0)$. Thus, the restored bone models 28 share the same orientation and positioning relative to the origin $(X_0, Y_0, Z_0)$ as the bone models 22.

In one embodiment, the restored bone models 28 are manually created from the bone models 22 by a person sitting in front of a computer 6 and visually observing the bone models 22 and their degenerated surfaces 24, 26 as 3D computer models on a computer screen 9. The person visually observes the degenerated surfaces 24, 26 to determine how and to what extent the degenerated surfaces 24, 26 on the 3D computer bone models 22 need to be modified to generally restore them to their pre-degenerated condition or an estimation or approximation of their pre-degenerated state. By interacting with the computer controls 11, the person then manually manipulates the 3D degenerated surfaces 24, 26 via the 3D modeling computer program to restore the surfaces 24, 26 to a state the person believes to represent the pre-degenerated condition. The result of this manual restoration process is the computer generated 3D restored bone models 28, wherein the surfaces 24', 26' are indicated in a non-degenerated state. In other words, the result is restored bone models 28 that can be used to represent the natural, pre-degenerated alignment and configuration of the patient's knee joint whether that pre-degenerated alignment and configuration was varus, valgus or neutral.

In one embodiment, the above-described bone restoration process is generally or completely automated to occur via a processor employing the methods disclosed herein. In other words, a computer program may analyze the bone models 22 and their degenerated surfaces 24, 26 to determine how and to what extent the degenerated surfaces 24, 26 surfaces on the 3D computer bone models 22 need to be modified to restore them to their pre-degenerated condition or an estimation or approximation of their pre-degenerated state. The computer program then manipulates the 3D degenerated surfaces 24, 26 to restore the surfaces 24, 26 to a state intended to represent the pre-degenerated condition. The result of this automated restoration process is the computer generated 3D restored bone models 28, wherein the surfaces 24', 26' are indicated in a non-degenerated state. A discussion of various embodiments of the automated restoration process employed to a greater or lesser extent by a computer is provided later in this Detailed Description.

As depicted in FIG. 1C, the restored bone models 28 are employed in a preoperative planning ("POP") procedure to determine saw cut locations 30 and drill hole locations 32 in the patient's bones that will allow the arthroplasty joint implants, whether in the context of total joint arthroplasty or partial or compartmentalized joint arthroplasty, to generally restore the patient's joint line to its pre-degenerative or natural alignment [block 120].

In one embodiment, the POP procedure is a manual process, wherein computer generated 3D implant models 34 (e.g., femur and tibia implants in the context of the joint being a knee) and restored bone models 28 are manually manipulated relative to each other by a person sitting in front of a computer 6 and visually observing the implant models 34 and restored bone models 28 on the computer screen 9 and manipulating the models 28, 34 via the computer controls 11. By superimposing the implant models 34 over the restored bone models 28, or vice versa, the joint surfaces of the implant models 34 can be aligned or caused to correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

In one embodiment, the POP process is generally or completely automated. For example, a computer program may manipulate computer generated 3D implant models 34 (e.g., femur and tibia implants in the context of the joint being a knee) and restored bone models or planning bone models 8 relative to each other to determine the saw cut and drill hole locations 30, 32 relative to the restored bone models 28. The implant models 34 may be superimposed over the restored bone models 28, or vice versa. In one embodiment, the implant models 34 are located at point P' $(X_{0-k}, Y_{0-k}, Z_{0-k})$ relative to the origin $(X_0, Y_0, Z_0)$, and the restored bone models 28 are located at point P $(X_{0-j}, Y_{0-j}, Z_{0-j})$. To cause the joint surfaces of the models 28, 34 to correspond, the computer program may move the restored bone models 28 from point P $(X_{0-j}, Y_{0-j}, Z_{0-j})$ to point P' $(X_{0-k}, Y_{0-k}, Z_{0-k})$, or vice versa. Once the joint surfaces of the models 28, 34 are in close proximity, the joint surfaces of the implant models 34 may be shape-matched to align or correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

As indicated in FIG. 1E, in one embodiment, the data 44 regarding the saw cut and drill hole locations 30, 32 relative to point P' $(X_{0-k}, Y_{0-k}, Z_{0-k})$ is packaged or consolidated as the "saw cut and drill hole data" 44 [block 145]. The "saw cut and drill hole data" 44 is then used as discussed below with respect to [block 150] in FIG. 1E.

As can be understood from FIG. 1D, the 2D images 16 employed to generate the bone models 22 discussed above with respect to [block 110] of FIG. 1C are also used to create computer generated 3D bone and cartilage models (i.e., "arthritic models") 36 of the bones 18, 20 forming the patient's joint 14 [block 130]. Like the above-discussed bone models 22, the arthritic models 36 are located such that point P is at coordinates $(X_{0-j}, Y_{0-j}, Z_{0-j})$ relative to the origin $(X_0, Y_0, Z_0)$ of the X-Y-Z axis [block 130]. Thus, the bone and arthritic models 22, 36 share the same location and orientation relative to the origin $(X_0, Y_0, Z_0)$. This position/orientation relationship is generally maintained throughout the process discussed with respect to FIGS. 1B-1E. Accordingly, movements relative to the origin $(X_0, Y_0, Z_0)$ of the bone models 22 and the various descendants thereof (i.e., the restored bone models 28, bone cut locations 30 and drill hole locations 32) are also applied to the arthritic models 36 and the various descendants thereof (i.e., the jig models 38). Maintaining the position/orientation relationship between the bone models 22 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2.

Computer programs for creating the 3D computer generated arthritic models 36 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

Similar to the bone models 22, the arthritic models 36 depict the bones 18, 20 in the present deteriorated condition with their respective degenerated joint surfaces 24, 26, which may be a result of osteoarthritis, injury, a combination thereof, etc. However, unlike the bone models 22, the arthritic models 36 are not bone-only models, but include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1D and already mentioned above, to coordinate the positions/orientations of the bone and arthritic models 36, 36 and their respective descendants, any movement of the restored bone models 28 from point P to point P' is tracked to cause a generally identical displacement for the "arthritic models" 36 [block 135].

As depicted in FIG. 1D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point P' ($X_{0-k}$, $Y_{0-k}$, $Z_{0-k}$) can also be imported into the jig models 38, resulting in jig models 38 positioned and oriented relative to point P' ($X_{0-k}$, $Y_{0-k}$, $Z_{0-k}$) to allow their integration with the bone cut and drill hole data 44 of [block 125].

In one embodiment, the procedure for indexing the jig models 38 to the arthroplasty target areas 42 is generally or completely automated, as disclosed in U.S. patent application Ser. No. 11/959,344 to Park, which is entitled System and Method for Manufacturing Arthroplasty Jigs, was filed Dec. 18, 2007 and is incorporated by reference in its entirety into this Detailed Description. For example, a computer program may create 3D computer generated surface models 40 of the arthroplasty target areas 42 of the arthritic models 36. The computer program may then import the surface models 40 and point P' ($X_{0-k}$, $Y_{0-k}$, $Z_{0-k}$) into the jig models 38, resulting in the jig models 38 being indexed to matingly receive the arthroplasty target areas 42 of the arthritic models 36. The resulting jig models 38 are also positioned and oriented relative to point P' ($X_{0-k}$, $Y_{0-k}$, $Z_{0-k}$) to allow their integration with the bone cut and drill hole data 44 of [block 125].

In one embodiment, the arthritic models 36 may be 3D volumetric models as generated from the closed-loop process discussed in U.S. patent application Ser. No. 11/959,344 filed by Park. In other embodiments, the arthritic models 36 may be 3D surface models as generated from the open-loop process discussed in U.S. patent application Ser. No. 11/959,344 filed by Park.

As indicated in FIG. 1E, in one embodiment, the data regarding the jig models 38 and surface models 40 relative to point P' ($X_{0-k}$, $Y_{0-k}$, $Z_{0-k}$) is packaged or consolidated as the "jig data" 46 [block 145]. The "jig data" 46 is then used as discussed below with respect to [block 150] in FIG. 1E.

As can be understood from FIG. 1E, the "saw cut and drill hole data" 44 is integrated with the "jig data" 46 to result in the "integrated jig data" 48 [block 150]. As explained above, since the "saw cut and drill hole data" 44, "jig data" 46 and their various ancestors (e.g., models 22, 28, 36, 38) are matched to each other for position and orientation relative to point P and P', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated state or, in other words, the joint's natural alignment.

As can be understood from FIGS. 1A and 1E, the "integrated jig data" 44 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50.

Figure 1F:
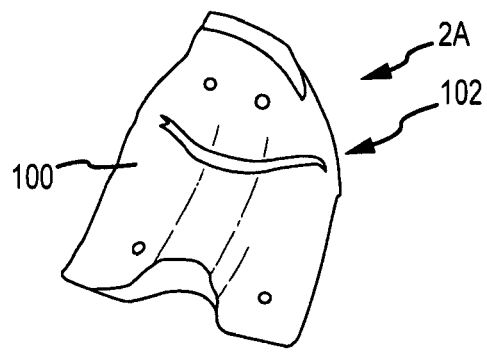
FIGS. 1F and 1G are, respectively, bottom and top perspective views of an example customized arthroplasty femur jig.
Figure 1G:
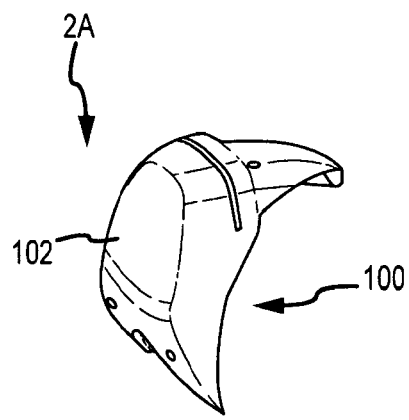
Figure 1H:
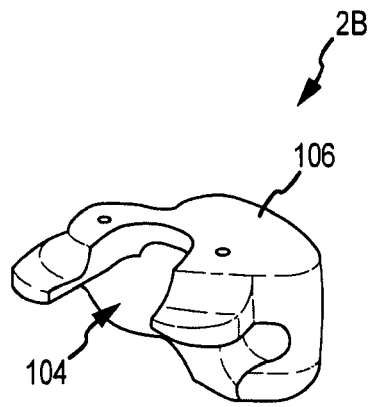
FIGS. 1H and 1I are, respectively, bottom and top perspective views of an example customized arthroplasty tibia jig.
Figure 1I:
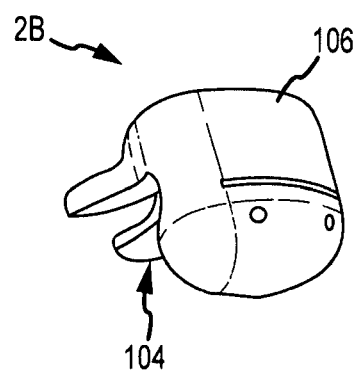

For a discussion of example customized arthroplasty cutting jigs 2 capable of being manufactured via the above-discussed process, reference is made to FIGS. 1F-1I. While, as pointed out above, the above-discussed process may be employed to manufacture jigs 2 configured for arthroplasty procedures (e.g., total joint replacement, partial joint replacement, joint resurfacing, etc.) involving knees, elbows, ankles, wrists, hips, shoulders, vertebra interfaces, etc., the jig examples depicted in FIGS. 1F-1I are for total knee replacement ("TKR") or partial knee replacement. Thus, FIGS. 1F and 1G are, respectively, bottom and top perspective views of an example customized arthroplasty femur jig 2A, and FIGS. 1H and 1I are, respectively, bottom and top perspective views of an example customized arthroplasty tibia jig 2B.

As indicated in FIGS. 1F and 1G, a femur arthroplasty jig 2A may include an interior side or portion 100 and an exterior side or portion 102. When the femur cutting jig 2A is used in a TKR or partial knee replacement procedure, the interior side or portion 100 faces and matingly receives the arthroplasty target area 42 of the femur lower end, and the exterior side or portion 102 is on the opposite side of the femur cutting jig 2A from the interior portion 100.

The interior portion 100 of the femur jig 2A is configured to match the surface features of the damaged lower end (i.e., the arthroplasty target area 42) of the patient's femur 18. Thus, when the target area 42 is received in the interior portion 100 of the femur jig 2A during the TKR or partial knee replacement surgery, the surfaces of the target area 42 and the interior portion 100 match.

The surface of the interior portion 100 of the femur cutting jig 2A is machined or otherwise formed into a selected femur jig blank 50A and is based or defined off of a 3D surface model 40 of a target area 42 of the damaged lower end or target area 42 of the patient's femur 18.

As indicated in FIGS. 1H and 1I, a tibia arthroplasty jig 2B may include an interior side or portion 104 and an exterior side or portion 106. When the tibia cutting jig 2B is used in a TKR or partial knee replacement procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR or partial knee replacement surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20.

b. Overview of Automated Processes for Restoring Damaged Regions of 3D Bone Models to Generate 3D Restored Bone Models As mentioned above with respect to [block 115] of FIG. 1C, the process for restoring damaged regions of 3D "bone models" 22 to generate 3D "restored bone models" 28 can be automated to be carried out to a greater or lesser extent by a computer. A discussion of various examples of such an automated process will now concern the remainder of this Detailed Description, beginning with an overview of various automated bone restoration processes.

As can be understood from FIG. 1A and [blocks 100-105] of FIG. 1B, a patient 12 has a joint 14 (e.g., a knee, elbow, ankle, wrist, shoulder, hip, vertebra interface, etc.) to be replaced (e.g., partially or totally) or resurfaced. The patient 12 has the joint 14 scanned in an imaging machine 10 (e.g., a CT, MRI, etc. machine) to create a plurality of 2D scan images 16 of the bones (e.g., femur 18 and tibia 20) forming the patient's joint 14 (e.g., knee). The process of creating the 2D scan images or slices 16 may occur as disclosed in Ser. No. 11/946,002, which was filed by Park Nov. 27, 2007 and is incorporated by reference in its entirety into this Detailed Description. Each scan image 16 is a thin slice image of the targeted bone(s) 18, 20. The scan images 16 are sent to the CPU 7, which may employ an open-loop or closed-loop image analysis along targeted features 42 of the scan images 16 of the bones 18, 20 to generate a contour line for each scan image 16 along the profile of the targeted features 42. The process of generating contour lines for each scan image 16 may occur as disclosed in Ser. No. 11/959,344, which is incorporated by reference in its entirety into this Detailed Description.

As can be understood from FIG. 1A and [block 110] of FIG. 1C, the CPU 7 compiles the scan images 16 and, more specifically, the contour lines to generate 3D computer surface or volumetric models ("bone models") 22 of the targeted features 42 of the patient's joint bones 18, 20. In the context of total knee replacement ("TKR") or partial knee replacement surgery, the targeted features 42 may be the lower or knee joint portions of the patient's femur 18 and the upper or knee joint portions of the patient's tibia 20. More specifically, for the purposes of generating the femur bone models 22, the targeted features 42 may include the condyle portion of the femur and may extend upward to include at least a portion of the femur shaft. Similarly, for purposes of generating the tibia bone models 22, the targeted features 42 may include the plateau portion of the tibia and may extend downward to include at least a portion of the tibia shaft.

In some embodiments, the "bone models" 22 may be surface models or volumetric solid models respectively formed via an open-loop or closed-loop process such that the contour lines are respectively open or closed loops. Regardless, the bone models 22 are bone-only 3D computer generated models of the joint bones that are the subject of the arthroplasty procedure. The bone models 22 represent the bones in the deteriorated condition in which they existed at the time of the medical imaging of the bones.

To allow for the POP procedure, wherein the saw cut and drill hole locations 30, 32 are determined as discussed with respect to [block 120] of FIG. 1C, the "bone models" 22 and/or the image slices 16 (see [block 100] of FIG. 1B) are modified to generate a 3D computer generated model that approximates the condition of the patient's bones prior to their degeneration. In other words, the resulting 3D computer generated model, which is termed a "restored bone model" 28, approximates the patient's bones in a non-degenerated or healthy state and can be used to represent the patient's joint in its natural alignment prior to degeneration.

Figure 2:
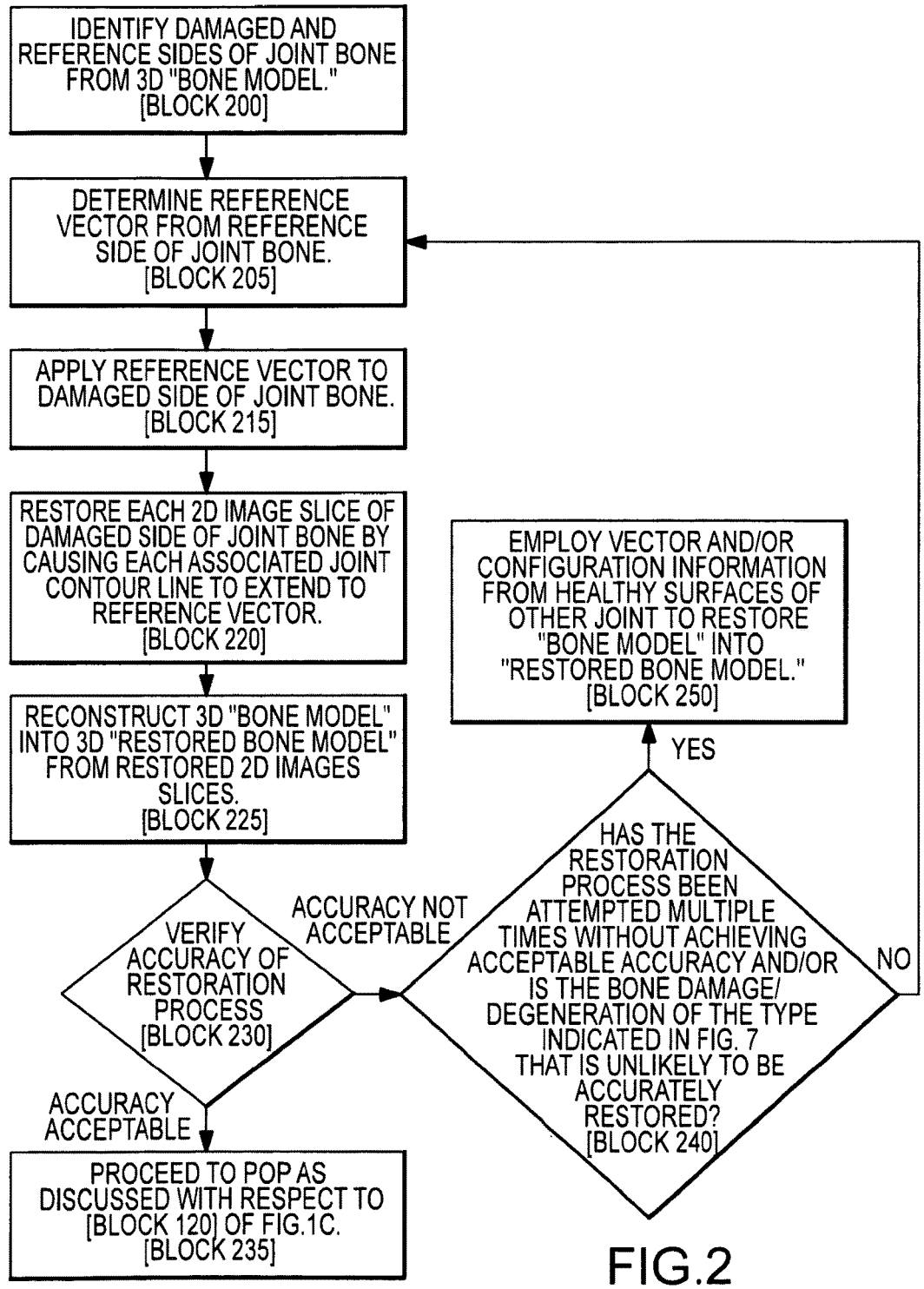
FIG. 2 is a diagram generally illustrating a bone restoration process for restoring a 3D computer generated bone model into a 3D computer generated restored bone model.

In one embodiment, the bone restoration process employed to generate the restored bone model 28 from the bone model 22 or image slices 16 may be as indicated in the process diagram depicted in FIG. 2. As shown in FIG. 2, the damaged and reference sides of a joint bone to undergo an arthroplasty procedure are identified from the 3D computer generated "bone model" [block 200]. The damaged side is the side or portion of the joint bone that needs to be restored in the bone model 22, and the reference side is the side of the joint bone that is generally undamaged or at least sufficiently free of deterioration that it can serve as a reference for restoring the damaged side.

As can be understood from FIG. 2, reference data or information (e.g., in the form of ellipses, ellipse axes, and/or vectors in the form of lines and/or planes) is then determined from the reference side of the joint bone [block 205]. The reference information or data is then applied to the damaged side of the joint bone [block 215]. For example, in a first embodiment and in the context of a knee joint, a vector associated with a femur condyle ellipse of the reference side is determined and applied to the damaged side femur condyle and damaged side tibia plateau. In a second embodiment and in the context of a knee joint, a vector associated with the highest anterior and posterior points of a tibia plateau of the reference side is determined and applied to the damaged side femur condyle and damaged side tibia plateau. These vectors are generally parallel with the condyle ellipse and generally parallel with the knee joint line.

As indicated in FIG. 2, each joint contour line associated with a 2D image slice of the damaged side of the joint bone is caused to extend to the reference vector or ellipse [block 220]. This restoration process is carried out slice-by-slice for the joint contour lines of most, if not all, image slices associated with the damaged side of the joint. The 3D "bone model" is then reconstructed into the 3D "restored bone model" from the restored 2D images slices [block 225].

Once generated from the "bone model" 22, the "restored bone model" 28 can then be employed in the POP process discussed with respect to [block 120] of FIG. 1C. As discussed with respect to [blocks 125 and 150], "saw cut and drill hole data" resulting from the POP process is indexed into "jig data" 46 to create "integrated jig data" 48. As discussed with respect to [blocks 155-165] of FIG. 1E, the "integrated jig data" 48 is utilized by a CNC machine 10 to produce customized arthroplasty jigs 2.

The systems 4 and methods disclosed herein allow for the efficient manufacture of arthroplasty jigs 2 customized for the specific bone features of a patient. Each resulting arthroplasty jig 2 includes an interior portion dimensioned specific to the surface features of the patient's bone that are the focus of the arthroplasty. Each jig 2 also includes saw cut slots and drill holes that are indexed relative to the interior portion of the jig such that saw cuts and drill holes administered to the patient's bone via the jig will result in cuts and holes that will allow joint implants to restore the patient's joint line to a pre-degenerated state or at least a close approximation of the pre-degenerated state.

Where the arthroplasty is for TKR or partial knee replacement surgery, the jigs will be a femur jig and/or a tibia jig. The femur jig will have an interior portion custom configured to match the damaged surface of the lower or joint end of the patient's femur. The tibia jig will have an interior portion custom configured to match the damaged surface of the upper or joint end of the patient's tibia.

The jigs 2 and systems 4 and methods of producing such jigs are illustrated herein in the context of knees and TKR or partial knee replacement surgery. However, those skilled in the art will readily understand the jigs 2 and system 4 and methods of producing such jigs can be readily adapted for use in the context of other joints and joint replacement or resurfacing surgeries, e.g., surgeries for elbows, shoulders, hips, etc. Accordingly, the disclosure contained herein regarding the jigs 2 and systems 4 and methods of producing such jigs should not be considered as being limited to knees and TKR or partial knee replacement surgery, but should be considered as encompassing all types of joint surgeries.

c. Overview of the Mechanics of an Accurate Restored Bone Model

An overview discussion of the mechanics of an accurate restored bone model 28 will first be given before discussing any of the bone restoration procedures disclosed herein. While this overview discussion is given in the context of a knee joint 14 and, more particularly, a femur restored bone model 28A and a tibia restored bone model 28B, it should be remembered that this discussion is applicable to other joints (e.g., elbows, ankles, wrists, hips, spine, etc.) and should not be considered as being limited to knee joints 14, but to include all joints.

Figure 3A:
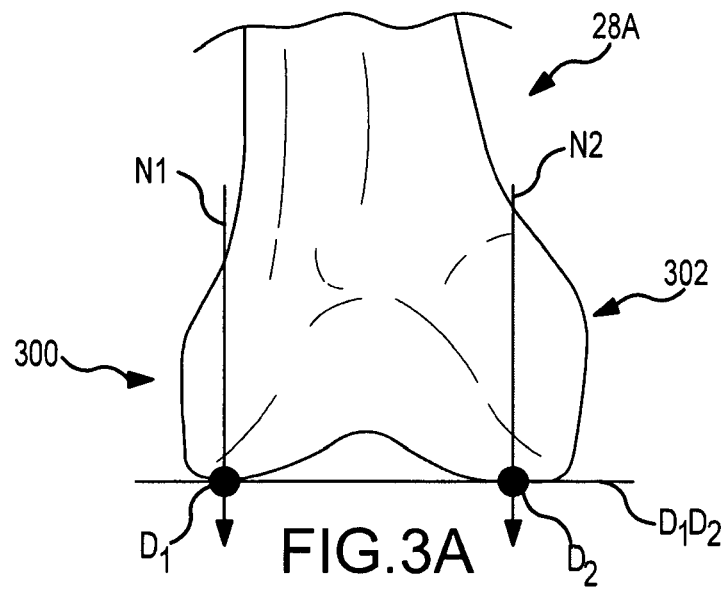
FIG. 3A is a coronal view of a distal or knee joint end of a femur restored bone model.

As shown in FIG. 3A, which is a coronal view of a distal or knee joint end of a femur restored bone model 28A, points $D_1$, $D_2$ represent the most distal tangent contact points of each of the femoral lateral and medial condyles 300, 302, respectively. In other words, points $D_1$, $D_2$ represent the lowest contact points of each of the femoral lateral and medial condyles 300, 302 when the knee is in zero degree extension. Line $D_1D_2$ can be obtained by extending across the two tangent contact points $D_1$, $D_2$. In this femur restored bone model 28A, line $D_1D_2$ is parallel or nearly parallel to the joint line of the knee when the knee is in zero degree extension.

The reference line N1 is perpendicular to line $D_1D_2$ at point $D_1$ and can be considered to represent a corresponding 2D image slice 16 taken along line N1. The reference line N2 is perpendicular to line $D_1D_2$ at point $D_2$ and can be considered to represent a corresponding 2D image slice 16 taken along line N2. The cross-sectional 2D image slices 16 taken along lines N1, N2 are perpendicular or nearly perpendicular to the tangent line $D_1D_2$ and joint line.

Figure 3B:
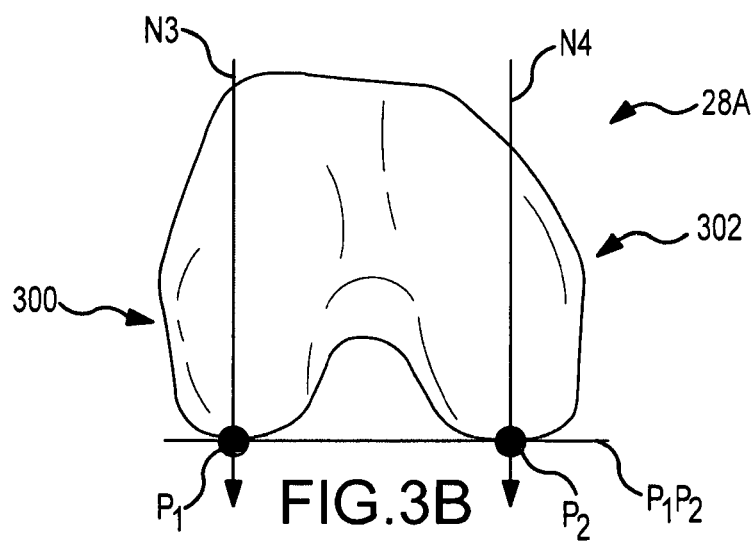
FIG. 3B is an axial view of a distal or knee joint end of a femur restored bone model.

As shown in FIG. 3B, which is an axial view of a distal or knee joint end of a femur restored bone model 28A, points $P_1$, $P_2$ represent the most posterior tangent contact points of each of the femoral lateral and medial condyles 300, 302, respectively. In other words, points $P_1$, $P_2$ represent the lowest contact points of each of the femoral lateral and medial condyles 300, 302 when the knee is in 90 degree extension. Line $P_1P_2$ can be obtained by extending across the two tangent contact points $P_1$, $P_2$. In this femur restored bone model 28A, line $P_1P_2$ is parallel or nearly parallel to the joint line of the knee when the knee is in 90 degree flexion.

The reference line N3 is perpendicular to line $P_1P_2$ at point $P_1$ and can be considered to represent a corresponding 2D image slice 16 taken along line N3. In some instances, the lines N1, N3 may occupy generally the same space on the femur restored bone model 28A or lines N1, N3 may be offset to a greater or lesser extent from each other along the joint line of the knee. The reference line N4 is perpendicular to line $P_1P_2$ at point $P_2$ and can be considered to represent a corresponding 2D image slice 16 taken along line N4. In some instances, the lines N2, N4 may occupy generally the same space on the femur restored bone model 28A or lines N2, N4 may be offset to a greater or lesser extent from each other along the joint line of the knee. The cross-sectional 2D image slices 16 taken along lines N3, N4 are perpendicular or nearly perpendicular to the tangent line $P_1P_2$ and joint line.

Figure 3C:
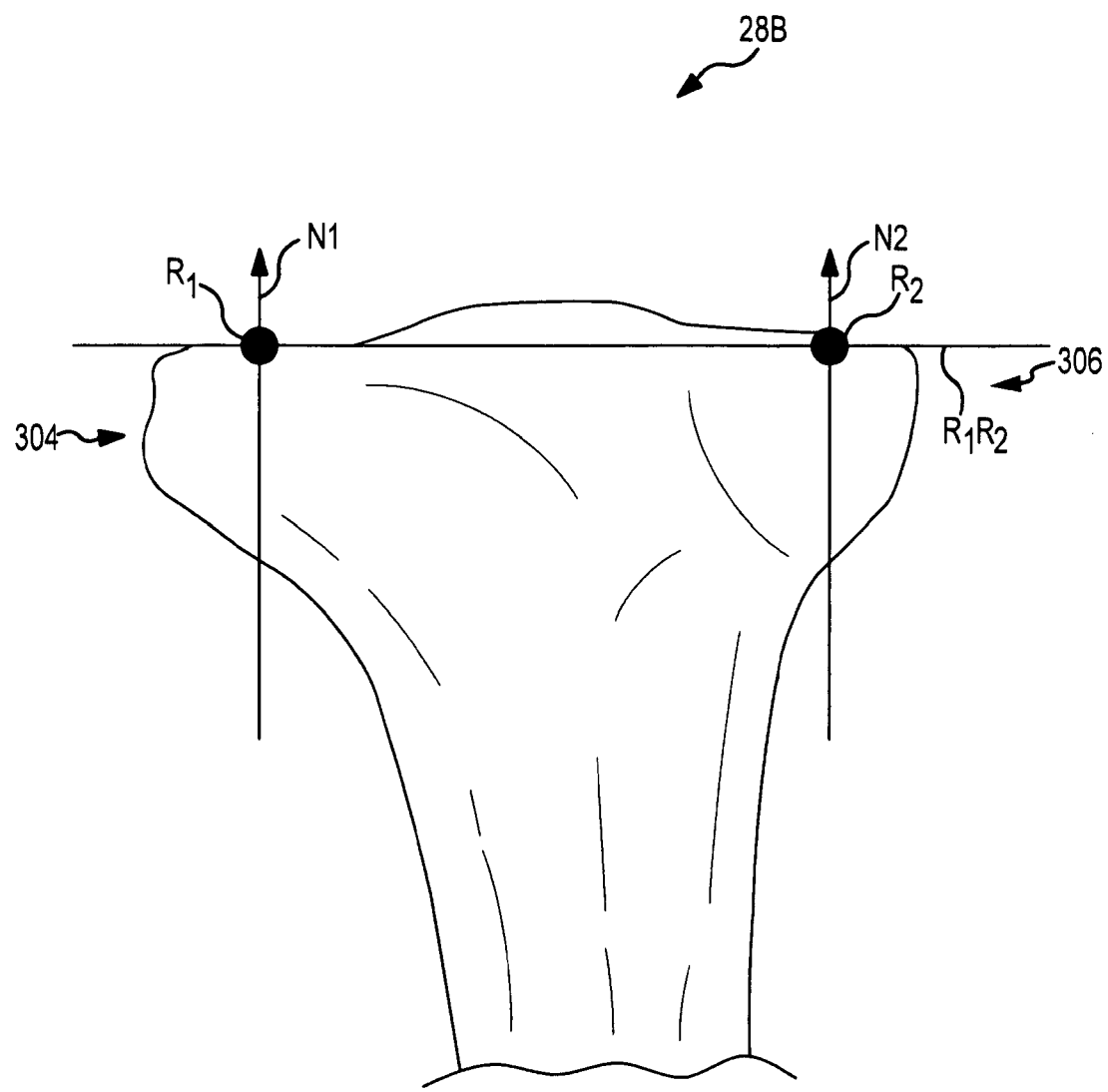
FIG. 3C is a coronal view of a proximal or knee joint end of a tibia restored bone model.

As shown in FIG. 3C, which is a coronal view of a proximal or knee joint end of a tibia restored bone model 28B, points $R_1$, $R_2$ represent the lowest tangent contact points of each of the tibial lateral and medial plateaus 304, 306, respectively. In other words, points $R_1$, $R_2$ represent the lowest points of contact of the tibia plateau with the femur condyles when the knee is in zero degree extension. Line $R_1R_2$ can be obtained by extending across the two tangent contact points $R_1$, $R_2$. In this tibia restored bone model 28B, line $R_1R_2$ is parallel or nearly parallel to the joint line of the knee when the knee is in zero degree extension. Also, when the knee joint is in zero degree extension, line $R_1R_2$ is parallel or nearly parallel to line $D_1D_2$. When the knee joint is in 90 degree extension, line $R_1R_2$ is parallel or nearly parallel to line $P_1P_2$.

The reference line N1 is perpendicular to line $R_1R_2$ at point $R_1$ and can be considered to represent a corresponding 2D image slice 16 taken along line N1. The reference line N2 is perpendicular to line $R_1R_2$ at point $R_2$ and can be considered to represent a corresponding 2D image slice 16 taken along line N2. The cross-sectional 2D image slices 16 taken along lines N1, N2 are perpendicular or nearly perpendicular to the tangent line $R_1R_2$ and joint line. Because both the femur and tibia restored bone models 28A, 28B represent the knee joint 14 prior to degeneration or damage, lines N1, N2 of the femur restored model 28A in FIG. 1A align with and may be the same as lines N1, N2 of the tibia restored bone model 28B when the knee joint is in zero degree extension. Thus, points $D_1$, $D_2$ align with points $R_1$, $R_2$ when the knee joint is in zero degree extension.

Figure 3D:
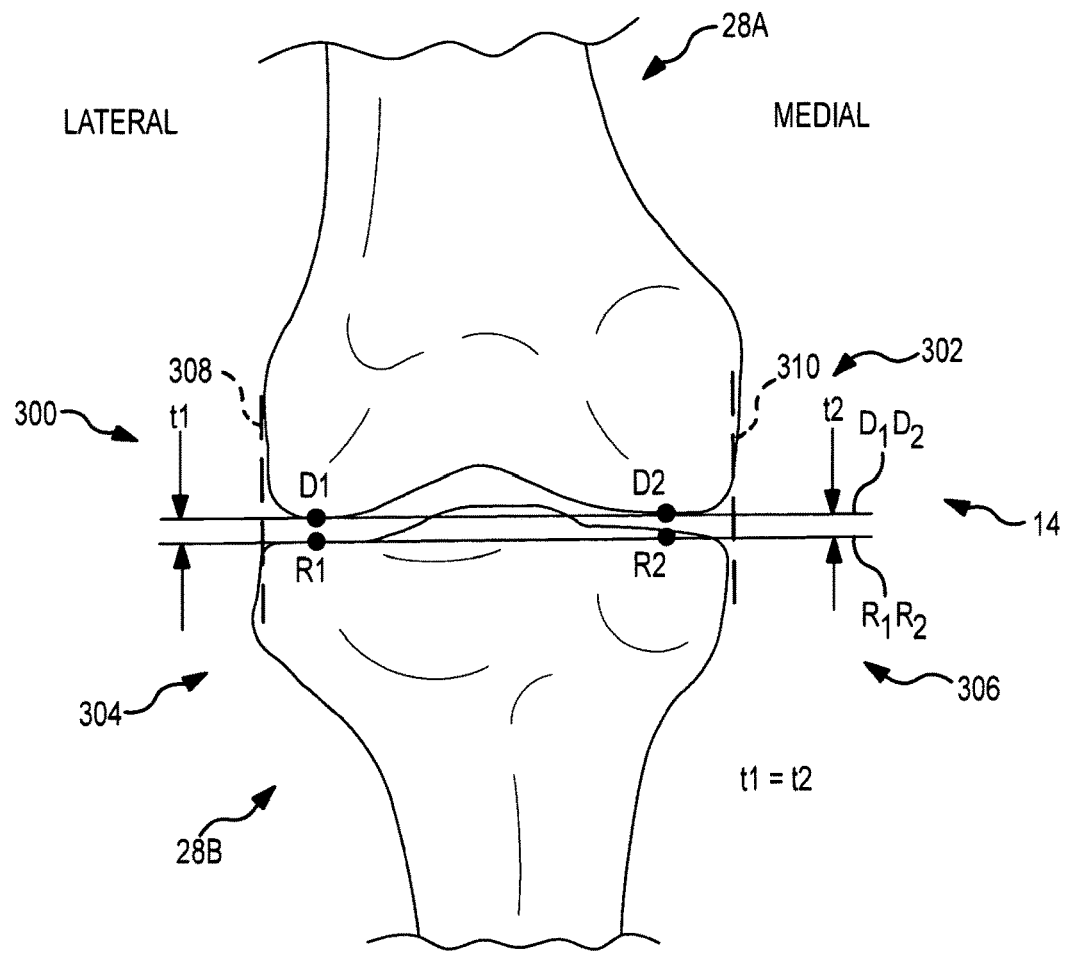
FIG. 3D represents the femur and tibia restored bone models in the views depicted in FIGS. 3A and 3C positioned together to form a knee joint.

FIG. 3D represents the femur and tibia restored bone models 28A, 28B in the views depicted in FIGS. 3A and 3C positioned together to form a knee joint 14. FIG. 3D shows the varus/valgus alignment of the femur and tibia restored bone models 28A, 28B intended to restore the patient's knee joint 14 back to its pre-OA or pre-degenerated state, wherein the knee joint 14 is shown in zero degree extension and in its natural alignment (e.g., neutral, varus or valgus) as the knee joint existed prior to degenerating. The respective locations of the lateral collateral ligament ("LCL") 308 and medial collateral ligament ("MCL") 310 are indicated in FIG. 3D by broken lines and serve as stabilizers for the side-to-side stability of the knee joint 14.

As can be understood from FIGS. 3A, 3C and 3D, when the knee joint 14 is in zero degree extension, lines N1, N2 are parallel or nearly parallel to the LCL 308 and MCL 310. Gap t1 represents the distance between the tangent contact point $D_1$ of the femoral lateral condyle 300 and the tangent contact point $R_1$ of the tibia lateral plateau 304. Gap t2 represents the distance between the tangent contact point $D_2$ of the femoral medial condyle 302 and the tangent contact point $R_2$ of the medial tibia plateau 306. For a properly restored knee joint 14, as depicted in FIG. 3D, in one embodiment, with respect to varus/valgus rotation and alignment, t1 is substantially equal to t2 such that the difference between t1 and t2 is less than one millimeter (e.g., [t1−t2] <<1 mm). Accordingly, line $D_1D_2$ is parallel or nearly parallel to the joint line and line $R_1R_2$.

Figure 3E:
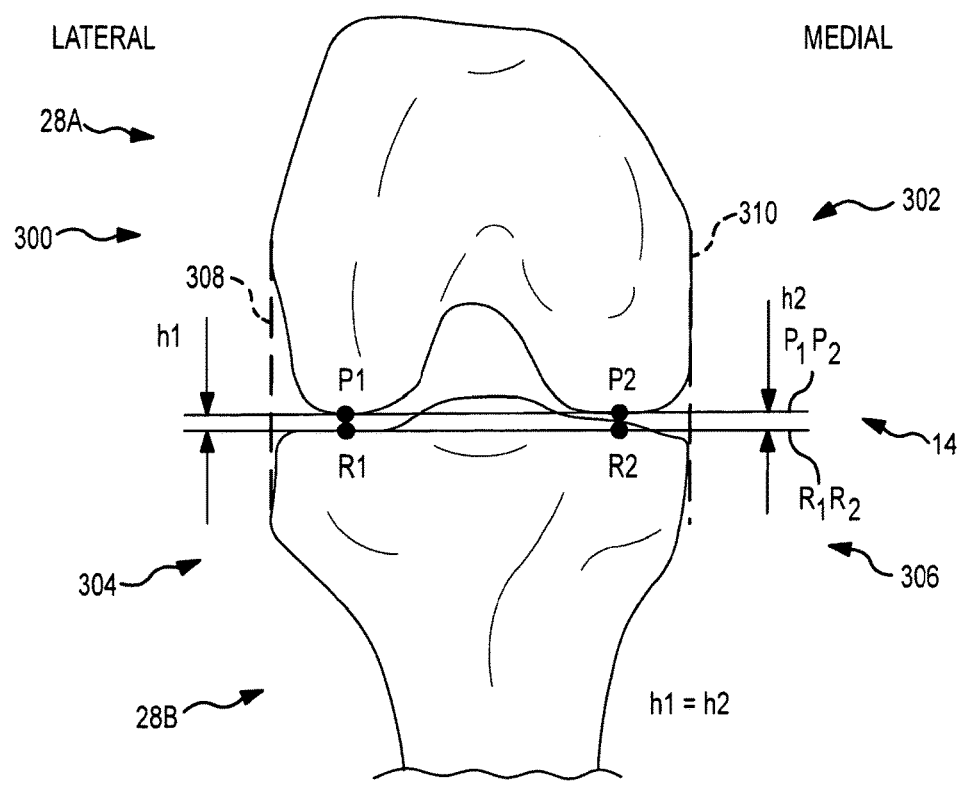
FIG. 3E represents the femur and tibia restored bone models in the views depicted in FIGS. 3B and 3C positioned together to form a knee joint.

FIG. 3E represents the femur and tibia restored bone models 28A, 28B in the views depicted in FIGS. 3B and 3C positioned together to form a knee joint 14. FIG. 3E shows the varus/valgus alignment of the femur and tibia restored bone models 28A, 28B intended to restore the patient's knee joint 14 back to its pre-OA or pre-degenerated state, wherein the knee joint 14 is shown in 90 degree flexion and in its natural alignment (e.g., neutral, varus or valgus) as the knee joint existed prior to degenerating. The respective locations of the lateral collateral ligament ("LCL") 308 and medial collateral ligament ("MCL") 310 are indicated in FIG. 3E by broken lines and serve as stabilizers for the side-to-side stability of the knee joint 14.

As can be understood from FIGS. 3B, 3C and 3E, when the knee joint 14 is in 90 degree flexion, lines N3, N4 are parallel or nearly parallel to the LCL 308 and MCL 310. Gap h1 represents the distance between the tangent contact point $P_1$ of the femoral lateral condyle 300 and the tangent contact point $R_1$ of the tibia lateral plateau 304. Gap h2 represents the distance between the tangent contact point $P_2$ of the femoral medial condyle 302 and the tangent contact point $R_2$ of the medial tibia plateau 306. For a properly restored knee joint 14, as depicted in FIG. 3E, in one embodiment, with respect to varus/valgus rotation and alignment, h1 is substantially equal to h2 such that the difference between h1 and h2 is less than one millimeter (e.g., [h1−h2]<<1 mm). Accordingly, line $P_1P_2$ is parallel or nearly parallel to the joint line and line $R_1R_2$.

Figure 3F:
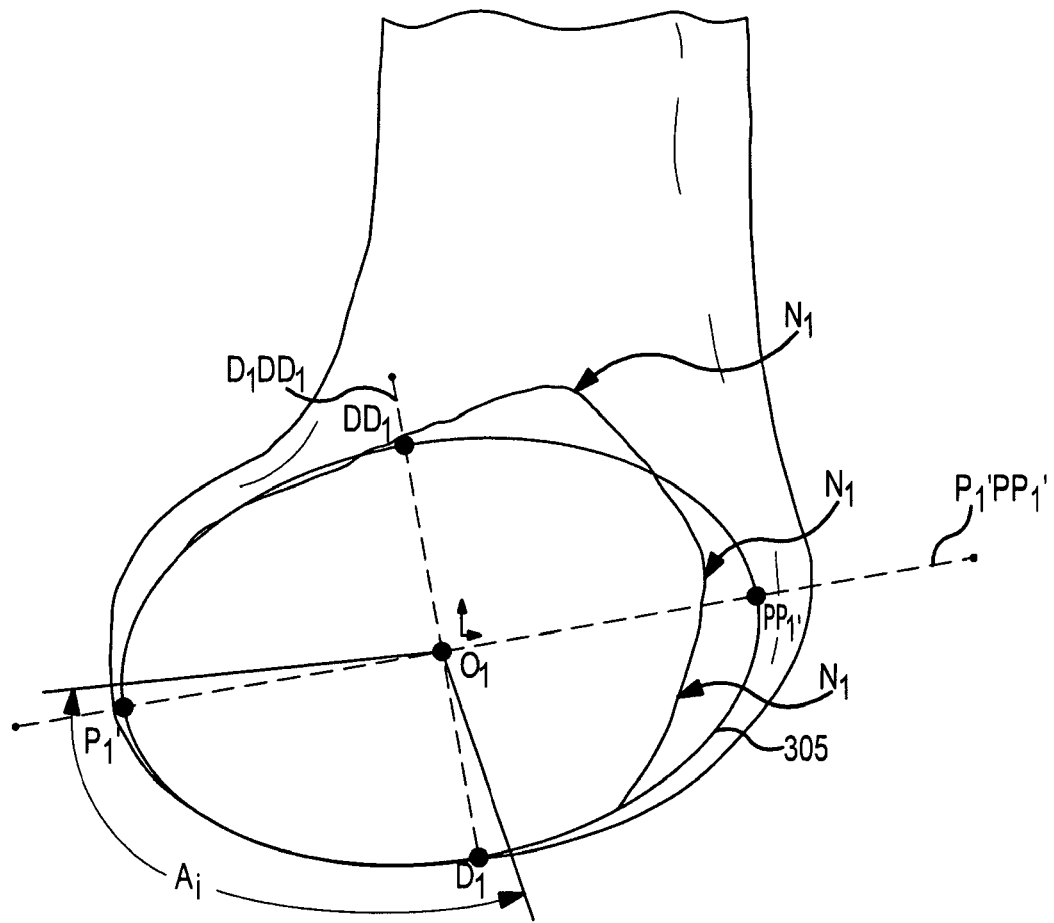
FIG. 3F is a sagittal view of the femoral medial condyle ellipse and, more specifically, the N1 slice of the femoral medial condyle ellipse as taken along line N1 in FIG. 3A.

FIG. 3F is a sagittal view of the femoral medial condyle ellipse 300 and, more specifically, the N1 slice of the femoral medial condyle ellipse 300 as taken along line N1 in FIG. 3A. The contour line $N_1$ in FIG. 3F represents the N1 image slice of the femoral medial condyle 300. The N1 image slice may be generated via such imaging methods as MRI, CT, etc. An ellipse contour 305 of the medial condyle 300 can be generated along contour line $N_1$. The ellipse 305 corresponds with most of the contour line $N_1$ for the N1 image slice, including the posterior and distal regions of the contour line $N_1$ and portions of the anterior region of the contour line $N_1$. As can be understood from FIG. 3F and discussed in greater detail below, the ellipse 305 provides a relatively close approximation of the contour line $N_1$ in a region of interest or region of contact $A_i$ that corresponds to an region of the femoral medial condyle surface that contacts and displaces against the tibia medial plateau.

As can be understood from FIGS. 3A, 3B and 3F, the ellipse 305 can be used to determine the distal extremity of the femoral medial condyle 300, wherein the distal extremity is the most distal tangent contact point $D_1$ of the femoral medial condyle 300 of the N1 slice. Similarly, the ellipse 305 can be used to determine the posterior extremity of the femoral medial condyle 300, wherein the posterior extremity is the most posterior tangent contact point $P_1'$ of the femoral medial condyle 300 of the N1 slice. The ellipse origin point $O_1$, the ellipse major axis $P_1'PP_1'$ and ellipse minor axis $D_1DD_1$ can be obtained based on the elliptical shape of the N1 slice of the medial condyle 300 in conjunction with well-known mathematical calculations for determining the characteristics of an ellipse.

As can be understood from FIG. 3F and as mentioned above, the region of contact $A_i$ represents or corresponds to the overlapping surface region between the medial tibia plateau 304 and the femoral medial condyle 300 along the N1 image slice. The region of contact $A_i$ for the N1 image slice is approximately 120° of the ellipse 305 of the N1 image slice from just proximal the most posterior tangent contact point PC to just anterior the most distal tangent contact point $D_1$.

Figure 3G:
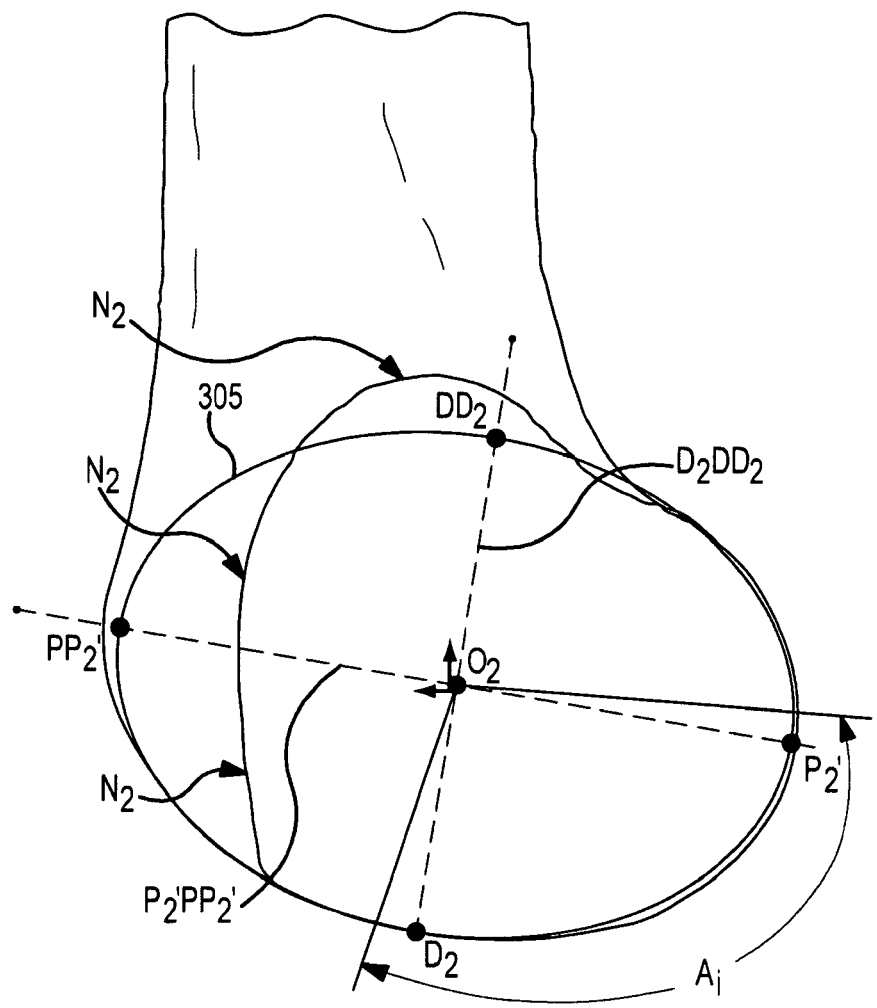
FIG. 3G is a sagittal view of the femoral lateral condyle ellipse and, more specifically, the N2 slice of the femoral lateral condyle ellipse as taken along line N2 in FIG. 3A.

FIG. 3G is a sagittal view of the femoral lateral condyle ellipse 302 and, more specifically, the N2 slice of the femoral lateral condyle ellipse 302 as taken along line N2 in FIG. 3A. The contour line $N_2$ in FIG. 3G represents the N2 image slice of the femoral lateral condyle 302. The N2 image slice may be generated via such imaging methods as MRI, CT, etc. An ellipse contour 305 of the lateral condyle 302 can be generated along contour line $N_2$. The ellipse 305 corresponds with most of the contour line $N_2$ for the N2 image slice, including the posterior and distal regions of the contour line $N_2$ and portions of the anterior region of the contour line $N_2$. As can be understood from FIG. 3G and discussed in greater detail below, the ellipse 305 provides a relatively close approximation of the contour line $N_2$ in a region of interest or region of contact $A_i$ that corresponds to an region of the femoral lateral condyle surface that contacts and displaces against the tibia lateral plateau.

As can be understood from FIGS. 3A, 3B and 3G, the ellipse 305 can be used to determine the distal extremity of the femoral lateral condyle 302, wherein the distal extremity is the most distal tangent contact point $D_2$ of the femoral lateral condyle 302 of the N2 slice. Similarly, the ellipse 305 can be used to determine the posterior extremity of the femoral lateral condyle 302, wherein the posterior extremity is the most posterior tangent contact point $P_2'$ of the femoral lateral condyle 302 of the N2 slice. The ellipse origin point $O_2$, the ellipse major axis $P_2'PP_2'$ and ellipse minor axis $D_2DD_2$ can be obtained based on the elliptical shape of the N2 slice of the lateral condyle 302 in conjunction with well-known mathematical calculations for determining the characteristics of an ellipse.

As can be understood from FIG. 3G and as mentioned above, the region of contact $A_i$ represents or corresponds to the overlapping surface region between the lateral tibia plateau 306 and the femoral lateral condyle 302 along the N2 image slice. The region of contact $A_i$ for the N2 image slice is approximately 120° of the ellipse 305 of the N2 image slice from just proximal the most posterior tangent contact point $P_2'$ to just anterior the most distal tangent contact point $D_2$.

Figure 3H:
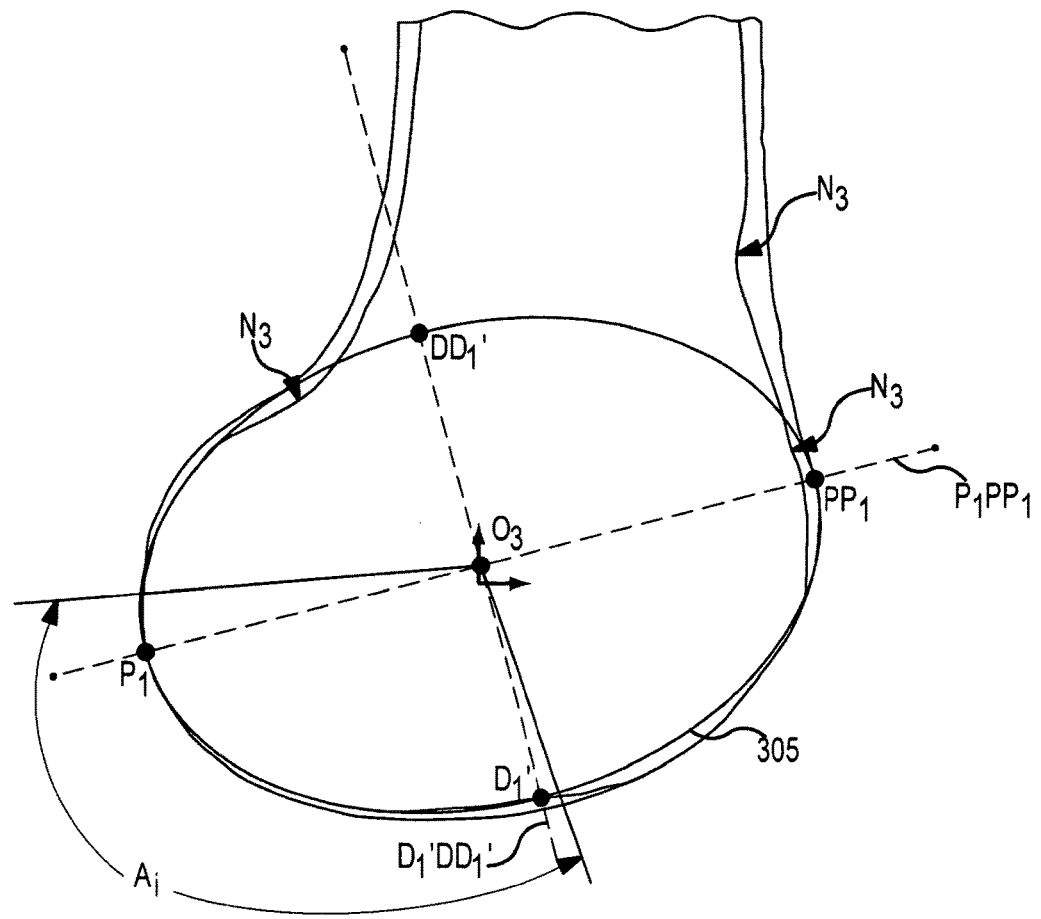
FIG. 3H is a sagittal view of the femoral medial condyle ellipse and, more specifically, the N3 slice of the femoral medial condyle ellipse as taken along line N3 in FIG. 3B.

FIG. 3H is a sagittal view of the femoral medial condyle ellipse 300 and, more specifically, the N3 slice of the femoral medial condyle ellipse 300 as taken along line N3 in FIG. 3B. The contour line $N_3$ in FIG. 3H represents the N3 image slice of the femoral medial condyle 300. The N3 image slice may be generated via such imaging methods as MRI, CT, etc. An ellipse contour 305 of the medial condyle 300 can be generated along contour line $N_3$. The ellipse 305 corresponds with most of the contour line $N_3$ for the N3 image slice, including the posterior and distal regions of the contour line $N_3$ and portions of the anterior region of the contour line $N_3$. As can be understood from FIG. 3H and discussed in greater detail below, the ellipse 305 provides a relatively close approximation of the contour line $N_3$ in a region of interest or region of contact $A_i$ that corresponds to an region of the femoral medial condyle surface that contacts and displaces against the tibia medial plateau.

As can be understood from FIGS. 3A, 3B and 3H, the ellipse 305 can be used to determine the distal extremity of the femoral medial condyle 300, wherein the distal extremity is the most distal tangent contact point $D_1'$ of the femoral medial condyle 300 of the N3 slice. Similarly, the ellipse 305 can be used to determine the posterior extremity of the femoral medial condyle 300, wherein the posterior extremity is the most posterior tangent contact point $P_1$ of the femoral medial condyle 300 of the N3 slice. The ellipse origin point $O_3$, the ellipse major axis $P_1PP_1$ and ellipse minor axis $D_1'DD_1'$ can be obtained based on the elliptical shape of the N3 slice of the medial condyle 300 in conjunction with well-known mathematical calculations for determining the characteristics of an ellipse.

As can be understood from FIG. 3H and as mentioned above, the region of contact $A_i$ represents or corresponds to the overlapping surface region between the medial tibia plateau 304 and the femoral medial condyle 300 along the N3 image slice. The region of contact $A_i$ for the N3 image slice is approximately 120° of the ellipse 305 of the N3 image slice from just proximal the most posterior tangent contact point $P_1$ to just anterior the most distal tangent contact point $D_1'$.

Figure 3I:
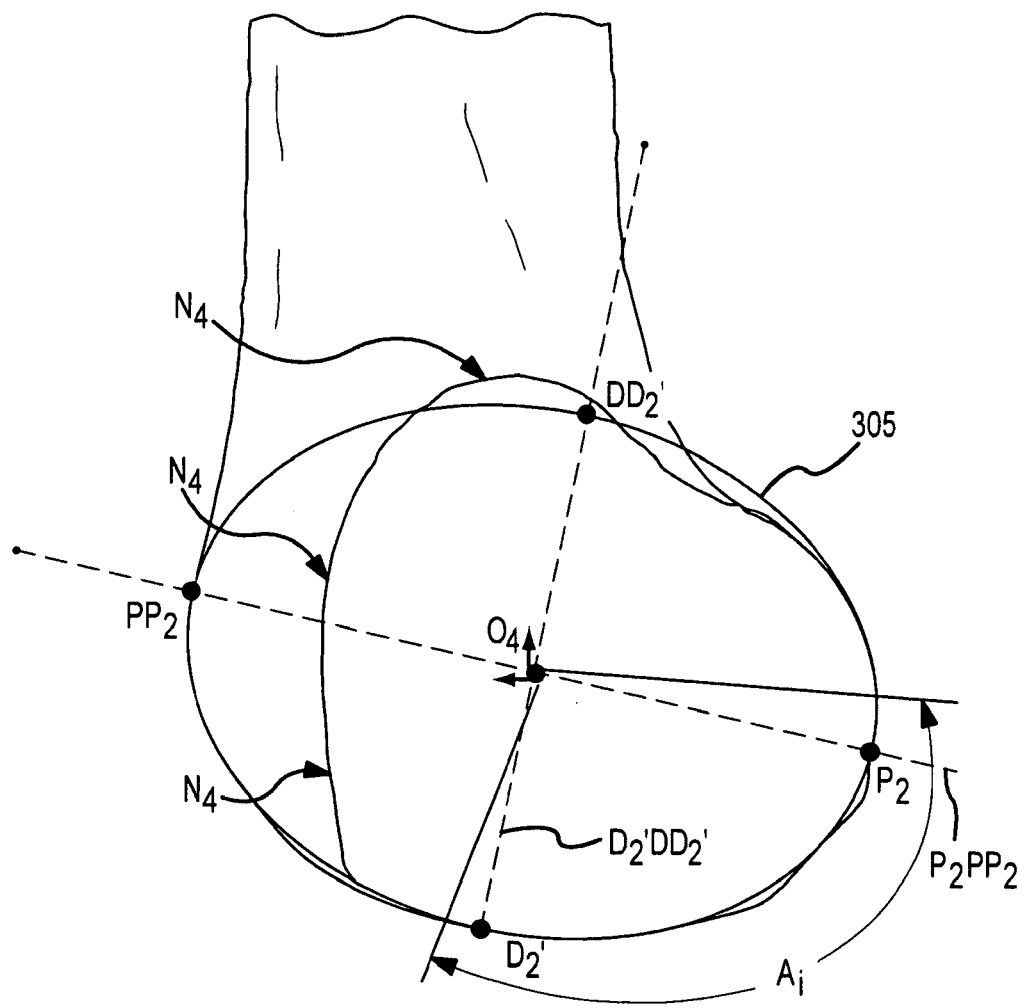
FIG. 3I is a sagittal view of the femoral lateral condyle ellipse and, more specifically, the N4 slice of the femoral lateral condyle ellipse as taken along line N4 in FIG. 3B.

FIG. 3I is a sagittal view of the femoral lateral condyle ellipse 302 and, more specifically, the N4 slice of the femoral lateral condyle ellipse 302 as taken along line N4 in FIG. 3B. The contour line $N_4$ in FIG. 3I represents the N4 image slice of the femoral lateral condyle 302. The N4 image slice may be generated via such imaging methods as MRI, CT, etc. An ellipse contour 305 of the lateral condyle 302 can be generated along contour line $N_4$. The ellipse 305 corresponds with most of the contour line $N_4$ for the N4 image slice, including the posterior and distal regions of the contour line $N_4$ and portions of the anterior region of the contour line $N_4$. As can be understood from FIG. 3G and discussed in greater detail below, the ellipse 305 provides a relatively close approximation of the contour line $N_4$ in a region of interest or region of contact $A_i$ that corresponds to an region of the femoral lateral condyle surface that contacts and displaces against the tibia lateral plateau.

As can be understood from FIGS. 3A, 3B and 3I, the ellipse 305 can be used to determine the distal extremity of the femoral lateral condyle 302, wherein the distal extremity is the most distal tangent contact point $D_2'$ of the femoral lateral condyle 302 of the N4 slice. Similarly, the ellipse 305 can be used to determine the posterior extremity of the femoral lateral condyle 302, wherein the posterior extremity is the most posterior tangent contact point $P_2$ of the femoral lateral condyle 302 of the N4 slice. The ellipse origin point $O_4$, the ellipse major axis $P_2PP_2$ and ellipse minor axis $D_2'DD_2'$ can be obtained based on the elliptical shape of the N4 slice of the lateral condyle 302 in conjunction with well-known mathematical calculations for determining the characteristics of an ellipse.

As can be understood from FIG. 3I and as mentioned above, the region of contact $A_i$ represents or corresponds to the overlapping surface region between the lateral tibia plateau 306 and the femoral lateral condyle 302 along the N4 image slice. The region of contact $A_i$ for the N4 image slice is approximately 120° of the ellipse 305 of the N4 image slice from just proximal the most posterior tangent contact point $P_2$ to just anterior the most distal tangent contact point $D_2'$.

While the preceding discussion is given in the context of image slices N1, N2, N3 and N4, of course similar elliptical contour lines, ellipse axes, tangent contact points and contact regions may be determined for the other image slices generated during the imaging of the patient's joint and which are parallel to image slices N1, N2, N3 and N4.

d. Employing Vectors from a Reference Side of a Joint to a Damaged Side of a Joint and Extending the Contour Lines of the Damaged Side to Meet the Vectors to Restore the Damaged Side A discussion of methods for determining reference vectors from a reference side of a joint bone for use in restoring a damaged side of the joint bone is first given, followed by specific examples of the restoration process in the context of MRI images. While this overview discussion is given in the context of a knee joint 14 and, more particularly, femur and tibia bone models 22A, 22B being converted image slice by slice into femur and tibia restored bone models 28A, 28B, it should be remembered that this discussion is applicable to other joints (e.g., elbows, ankles, wrists, hips, spine, etc.) and should not be considered as being limited to knee joints 14, but to include all joints. Also, while the image slices are discussed in the context of MRI image slices, it should be remembered that this discussion is applicable to all types of medical imaging, including CT scanning.

Figure 4A:
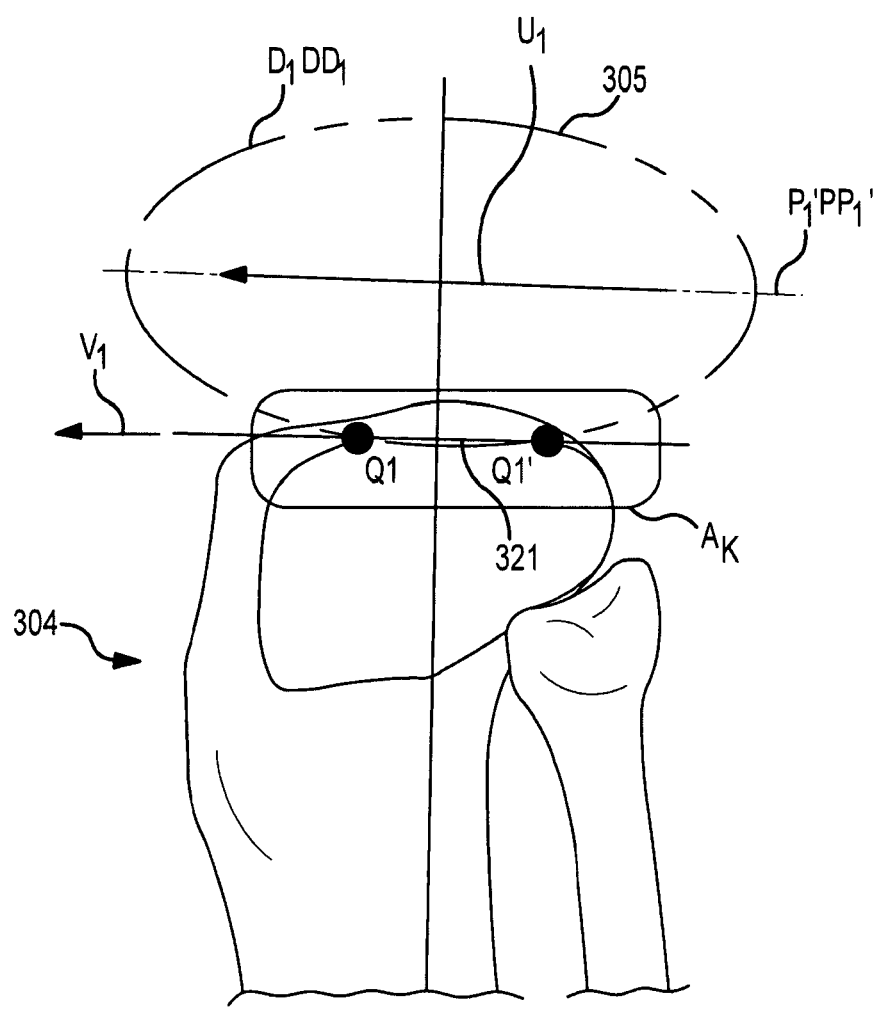
FIG. 4A is a sagittal view of the lateral tibia plateau with the lateral femur condyle ellipse of the N1 slice of FIG. 3F superimposed thereon.
Figure 4B:
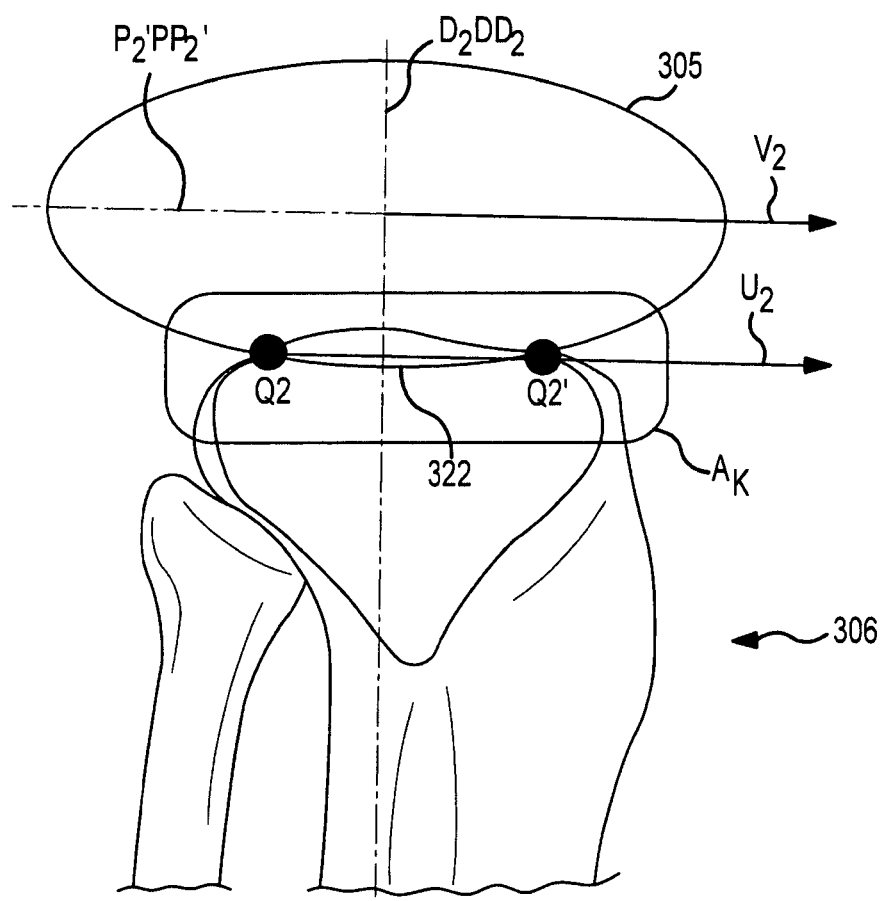
FIG. 4B is a sagittal view of the medial tibia plateau with the lateral femur condyle ellipse of the N2 slice of FIG. 3G superimposed thereon.

For a discussion of the motion mechanism of the knee and, more specifically, the motion vectors associated with the motion mechanism of the knee, reference is made to FIGS. 4A and 4B. FIG. 4A is a sagittal view of the lateral tibia plateau 304 with the lateral femur condyle ellipse 305 of the N1 slice of FIG. 3F superimposed thereon. FIG. 4B is a sagittal view of the medial tibia plateau 306 with the lateral femur condyle ellipse 305 of the N2 slice of FIG. 3G superimposed thereon.

The motion mechanism for a human knee joint operates as follows. The femoral condyles glide on the corresponding tibia plateaus as the knee moves, and in a walking theme, as a person's leg swings forward, the femoral condyles and the corresponding tibia plateaus are not under the compressive load of the body. Thus, the knee joint movement is a sliding motion of the tibia plateaus on the femoral condyles coupled with a rolling of the tibia plateaus on the femoral condyles in the same direction. The motion mechanism of the human knee as the femur condyles and tibia plateaus move relative to each other between zero degree flexion and 90 degree flexion has associated motion vectors. As discussed below, the geometrical features of the femur condyles and tibia plateaus can be analyzed to determine vectors $U_1$, $U_2$, $V_1$, $V_2$, $V_3$, $V_4$ that are associated with image slices N1, N2, N3 and N4. These vectors $U_1$, $U_2$, $V_1$, $V_2$, $V_3$, $V_4$ correspond to the motion vectors of the femur condyles and tibia plateaus moving relative to each other. The determined vectors $U_1$, $U_2$, $V_1$, $V_2$, $V_3$, $V_4$ associated with a healthy side of a joint 14 can be applied to a damaged side of a joint 14 to restore the bone model 22 to create a restored bone model 28.

In some embodiments of the bone restoration process disclosed herein and as just stated, the knee joint motion mechanism may be utilized to determine the vector references for the restoration of bone models 22 to restored bone models 28. As can be understood from a comparison of FIGS. 3F and 3G to FIGS. 4A and 4B, the $U_1$ and $U_2$ vectors respectively correspond to the major axes $P_1'PP_1'$ and $P_2'PP_2'$ of the ellipses 305 of the N1 and N2 slices. Since the major axes $P_1'PP_1'$ and $P_2'PP_2'$ exist in the N1 and N2 slices, which are planes generally perpendicular to the joint line, the $U_1$ and $U_2$ vectors may be considered to represent both vector lines and vector planes that are perpendicular to the joint line.

The $U_1$ and $U_2$ vectors are based on the joint line reference between the femur and the tibia from the zero degree flexion (full extension) to 90 degree flexion. The $U_1$ and $U_2$ vectors represent the momentary sliding movement force from zero degree flexion of the knee to any degree of flexion up to 90 degree flexion. As can be understood from FIGS. 4A and 4B, the $U_1$ and $U_2$ vectors, which are the vectors of the femoral condyles, are generally parallel to and project in the same direction as the $V_1$ and $V_2$ vectors of the tibia plateaus 321, 322. The vector planes associated with these vectors $U_1$, $U_2$, $V_1$, $V_2$ are presumed to be parallel or nearly parallel to the joint line of the knee joint 14 represented by restored bone model 28A, 28B such as those depicted in FIGS. 3D and 3E.

As shown in FIGS. 4A and 4B, the distal portion of the ellipses 305 extend along and generally correspond with the curved surfaces 321, 322 of the tibia plateaus. The curved portions 321, 322 of the tibia plateaus that generally correspond with the distal portions of the ellipses 305 represent the tibia contact regions $A_k$, which are the regions that contact and displace along the femur condyles and correspond with the condyle contact regions $A_i$ discussed with respect to FIGS. 3F-3I.

Figure 4C:
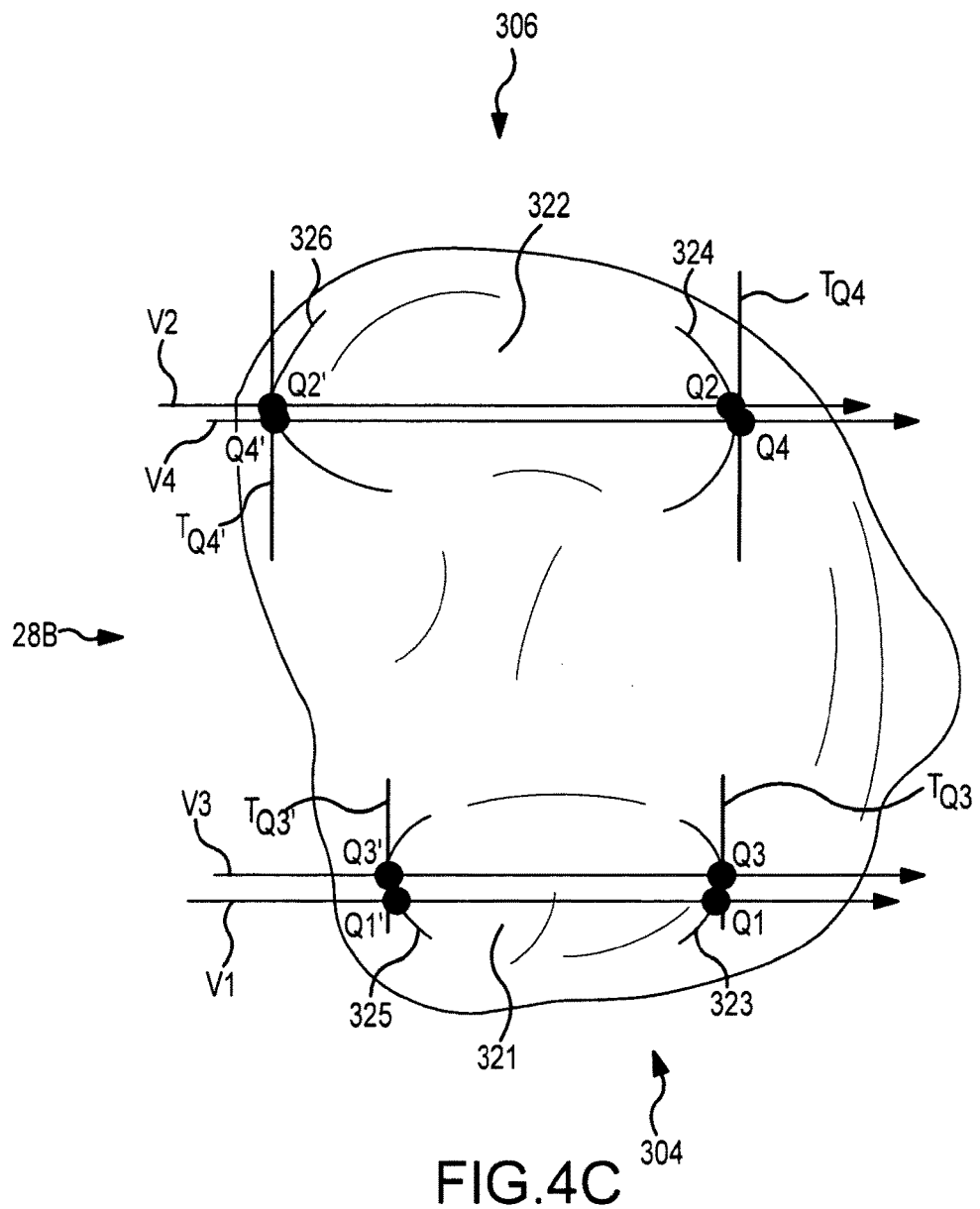
FIG. 4C is a top view of the tibia plateaus of a restored tibia bone model.
Figure 4D:
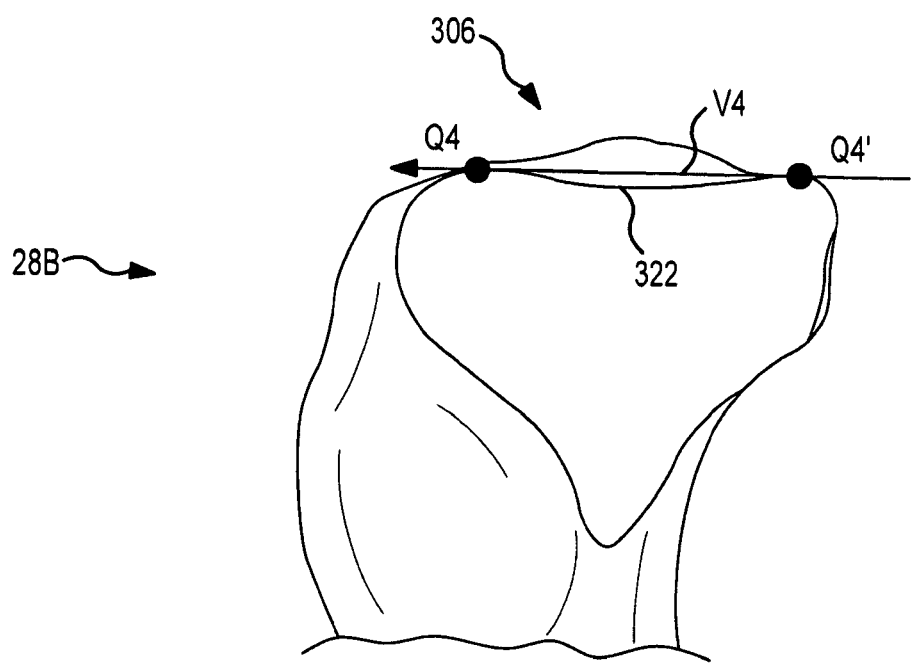
FIG. 4D is a sagittal cross section through a lateral tibia plateau of the restored bone model 28B of FIG. 4C and corresponding to the N3 image slice of FIG. 3B.
Figure 4E:
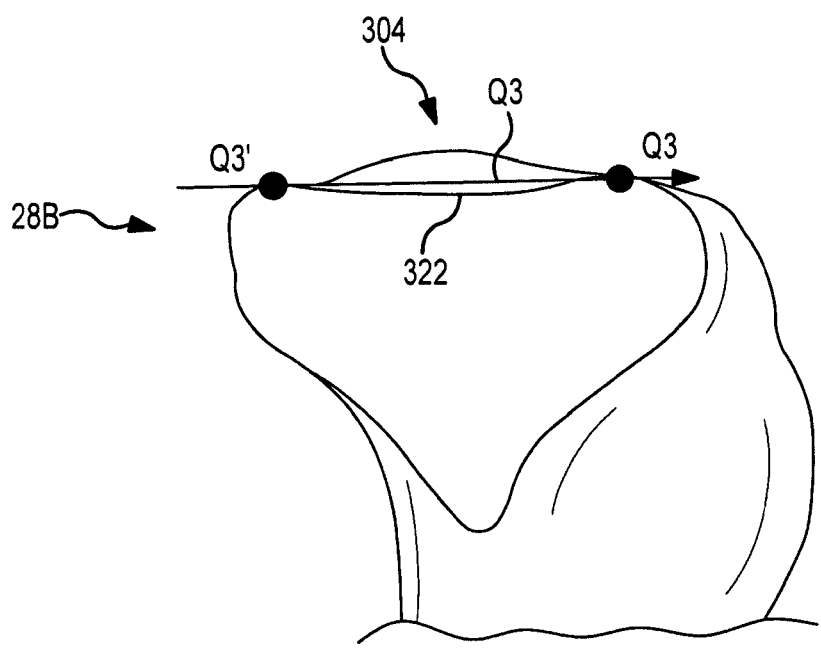
FIG. 4E is a sagittal cross section through a medial tibia plateau of the restored bone model of FIG. 4C and corresponding to the N4 image slice of FIG. 3B.

For a discussion of motion vectors associated with the tibia plateaus, reference is made to FIGS. 4C-4E. FIG. 4C is a top view of the tibia plateaus 304, 306 of a restored tibia bone model 28B. FIG. 4D is a sagittal cross section through a lateral tibia plateau 304 of the restored bone model 28B of FIG. 4C and corresponding to the N3 image slice of FIG. of FIG. 3B. FIG. 4E is a sagittal cross section through a medial tibia plateau 306 of the restored bone model 28B of FIG. 4C and corresponding to the N4 image slice of FIG. of FIG. 3B.

As shown in FIGS. 4C-4E, each tibia plateau 304, 306 includes a curved recessed condyle contacting surface 321, 322 that is generally concave extending anterior/posterior and medial/lateral. Each curved recessed surface 321, 322 is generally oval in shape and includes an anterior curved edge 323, 324 and a posterior curved edge 325, 326 that respectively generally define the anterior and posterior boundaries of the condyle contacting surfaces 321, 322 of the tibia plateaus 304, 306. Depending on the patient, the medial tibia plateau 306 may have curved edges 324, 326 that are slightly more defined than the curved edges 323, 325 of the lateral tibia plateau 304.

Anterior tangent lines $T_{Q3}$, $T_{Q4}$ can be extended tangentially to the most anterior location on each anterior curved edge 323, 324 to identify the most anterior points Q3, Q4 of the anterior curved edges 323, 324. Posterior tangent lines $T_{Q3'}$, $T_{Q4'}$ can be extended tangentially to the most posterior location on each posterior curved edge 325, 326 to identify the most posterior points Q3', Q4' of the posterior curved edges 325, 326. Such anterior and posterior points may correspond to the highest points of the anterior and posterior portions of the respective tibia plateaus.

Vector line V3 extends through anterior and posterior points Q3, Q3', and vector line V4 extends through anterior and posterior points Q4, Q4'. Each vector line V3, V4 may align with the lowest point of the anterior-posterior extending groove/valley that is the elliptical recessed tibia plateau surface 321, 322. The lowest point of the anterior-posterior extending groove/valley of the elliptical recessed tibia plateau surface 321, 322 may be determined via simple ellipsoid calculus. Each vector V3, V4 will be generally parallel to the anterior-posterior extending valleys of its respective elliptical recessed tibia plateau surface 321, 322 and will be generally perpendicular to it respective tangent lines $T_{Q3}$, $T_{Q4}$, $T_{Q3'}$, $T_{Q4'}$. The anterior-posterior extending valleys of the elliptical recessed tibia plateau surfaces 321, 322 and the vectors V3, V4 aligned therewith may be generally parallel with and even exist within the N3 and N4 image slices depicted in FIG. 3B.

As can be understood from FIGS. 4A-4E, the $V_3$ and $V_4$ vectors, which are the vectors of the tibia plateaus, are generally parallel to and project in the same direction as the other tibia plateau vectors $V_1$ and $V_2$ and, as a result, the femur condyle vectors $U_1$, $U_2$. The vector planes associated with these vectors $U_1$, $U_2$, $V_1$, $V_2$, $V_3$ and $V_4$ are presumed to be parallel or nearly parallel to the joint line of the knee joint 14 represented by restored bone models 28A, 28B such as those depicted in FIGS. 3D and 3E.

As indicated in FIGS. 4A-4C, tibia plateau vectors $V_1$ and $V_2$ in the N1 and N2 image slices can be obtained by superimposing the femoral condyle ellipses 305 of the N1 and N2 image slices onto their respective tibia plateaus. The ellipses 305 correspond to the elliptical tibia plateau surfaces 321, 322 along the condyle contact regions $A_k$ of the tibia plateaus 304, 306. The anterior and posterior edges 323, 324, 325, 326 of the elliptical tibia plateau surfaces 321, 322 can be determined at the locations where the ellipses 305 cease contact with the plateau surfaces 321. 322. These edges 323, 324, 325, 326 are marked as anterior and posterior edge points Q1, Q1', Q2, Q2' in respective image slices N1 and N2. Vector lines V1 and V2 are defined by being extended through their respective edge points Q1, Q1', Q2, Q2'.

As can be understood from FIG. 4C, image slices N1, N2, N3 and N4 and their respective vectors $V_1$, $V_2$, $V_3$ and $V_4$ may be medially-laterally spaced apart a greater or lesser extent, depending on the patient. With some patients, the N1 and N3 image slices and/or the N2 and N4 image slices may generally medially-laterally align.

While the preceding discussion is given with respect to vectors $U_1$, $U_2$, $V_1$, $V_2$, $V_3$ and $V_4$, contact regions $A_i$, $A_k$, and anterior and posterior edge points Q1, Q1', Q2, Q2', Q3, Q3', Q4, Q4' associated with image slices N1, N2, N3 and N4, similar vectors, contact regions, and anterior and posterior edge points can be determined for the other image slices 16 used to generate the 3D computer generated bone models 22 (see [block 100]-[block 110] of FIGS. 1A-1C).

As illustrated via the following examples given with respect to MRI slices, vectors similar to the $U_1$, $U_2$, $V_1$, $V_2$, $V_3$, $V_4$ vectors of FIGS. 4A-4E can be employed in restoring image slice-by-image slice the bone models 22A, 22B into restored bone models 28A, 28B. For example, a bone model 22 includes a femur bone model 22A and a tibia bone model 22B. The bone models 22A, 22B are 3D bone-only generated models compiled via any of the above-mentioned 3D computer programs from a number of image slices 16, as discussed with respect to [blocks 100]-[block 110] of FIGS. 1A-1C. Depending on the circumstances and generally speaking, either the medial side of the bone models will be generally undamaged and the lateral side of the bone models will be damaged, or vice versa.

Figure 4F:
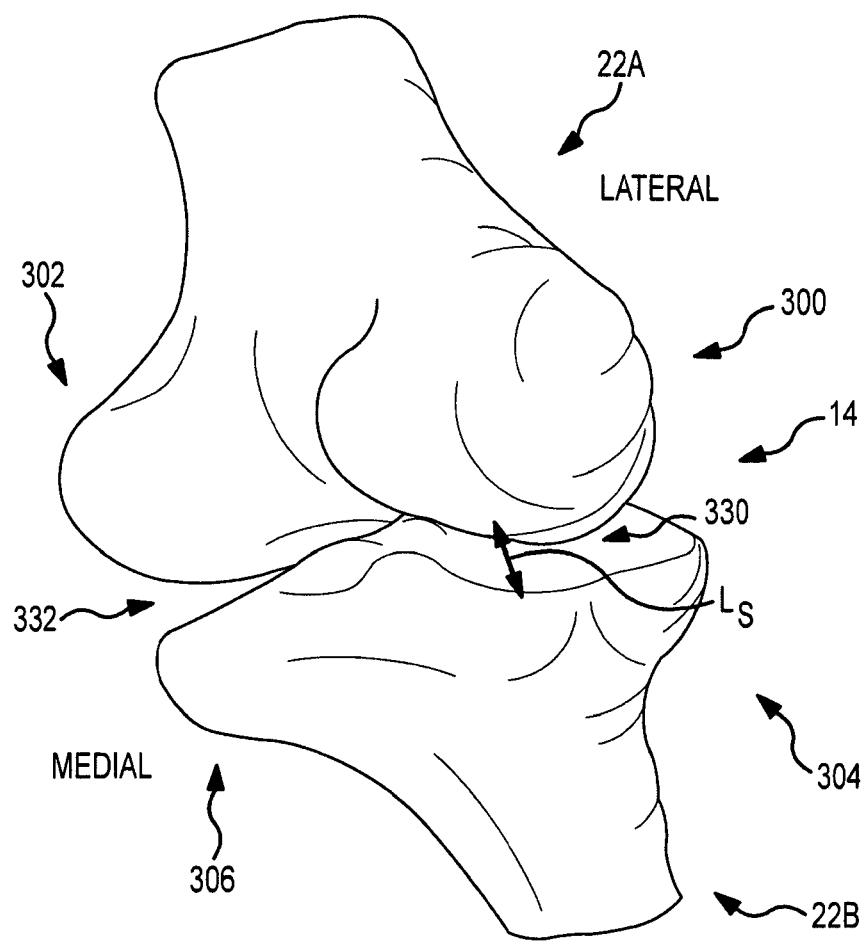
FIG. 4F is a posterior-lateral perspective view of femur and tibia bone models forming a knee joint.

For example, as indicated in FIG. 4F, which is a posterior-lateral perspective view of femur and tibia bone models 22A, 22B forming a knee joint 14, the medial sides 302, 306 of the bone models 22A, 22B are in a generally non-deteriorated condition and the lateral sides 300, 304 of the bone models 22A, 22B are in a generally deteriorated or damaged condition. The lateral sides 300, 304 of the femur and tibia bone models 22A, 22B depict the damaged bone attrition on the lateral tibia plateau and lateral femoral condyle. The lateral sides 300, 304 illustrate the typical results of OA, specifically joint deterioration in the region of arrow $L_S$ between the femoral lateral condyle 300 and the lateral tibia plateau 304, including the narrowing of the lateral joint space 330 as compared to medial joint space 332. As the medial sides 302, 306 of the bone models 22A, 22B are generally undamaged, these sides 302, 306 will be identified as the reference sides of the 3D bone models 22A, 22B (see [block 200] of FIG. 2). Also, as the lateral sides 300, 304 of the bone models 22A, 22B are damaged, these sides 300, 304 will be identified as the damaged sides of the 3D bone models 22A, 22B (see [block 200] of FIG. 2) and targeted for restoration, wherein the images slices 16 associated with the damaged sides 300, 304 of the bone models 22A, 22B are restored slice-by-slice.

Reference vectors like the $U_1$, $U_2$, $V_1$, $V_2$, $V_3$, $V_4$ vectors may be determined from the reference side of the bone models 22A, 22B (see [block 205] of FIG. 2). Thus, as can be understood from FIGS. 4B and 4F, since the medial sides 302, 306 are the reference sides 302, 306, the reference vectors $U_2$, $V_2$ $V_4$ may be applied to the damaged sides 300, 304 to restore the damaged sides 300, 304 2D image slice by 2D image slice (see [block 215]-[block 220] of FIG. 2). The restored image slices are then recompiled into a 3D computer generated model, the result being the 3D computer generated restored bone models 28A, 28B (see [block 225] of FIG. 2).

Figure 4G:
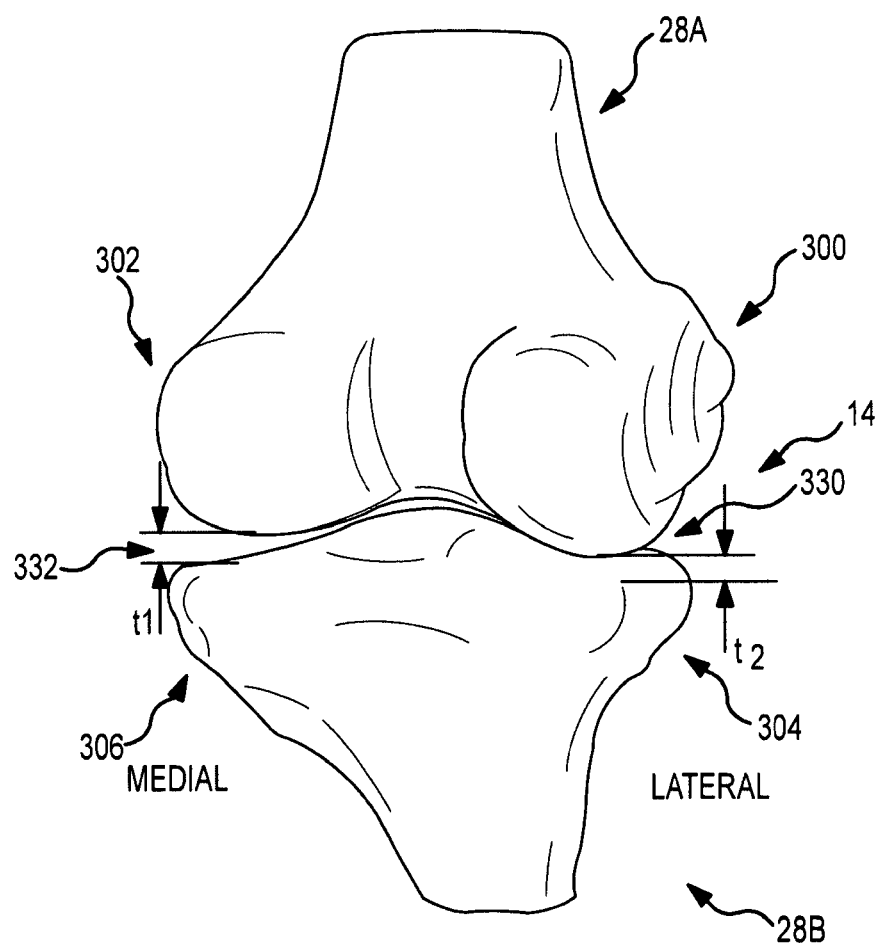
FIG. 4G is a posterior-lateral perspective view of femur and tibia restored bone models forming a knee joint.

As shown in FIG. 4G, which is a posterior-lateral perspective view of femur and tibia restored bone models 28A, 28B forming a knee joint 14, the lateral sides 300, 304 of the restored bone models 28A, 28B have been restored such that the lateral and medial joint spaces 330, 332 are generally equal. In other words, the distance t1 between the lateral femur condyle and lateral tibia plateau is generally equal to the distance t2 between the medial femur condyle and the medial tibia plateau.

The preceding discussion has occurred in the context of the medial sides 302, 306 being the reference sides and the lateral sides 300, 304 being the damaged sides; the reference vectors $U_2$, $V_2$ and $V_4$ of the medial sides 302, 306 being applied to the damaged sides 300, 304 in the process of restoring the damaged sides 300, 304. Of course, as stated above, the same process could occur in a reversed context, wherein the lateral sides 300, 304 are generally undamaged and are identified as the reference sides, and the medial sides 302, 306 are damaged and identified as the damaged sides. The reference vectors $U_1$, $V_1$ and $V_3$ of the lateral sides 300, 304 can then be applied to the damaged sides 302, 306 in the process of restoring the damaged sides 302, 306.

Multiple approaches are disclosed herein for identifying reference vectors and applying the reference vectors to a damaged side for the restoration thereof. For example, as can be understood from FIGS. 4B and 4F, where the medial sides 302, 306 are the undamaged reference sides 302, 304 and the lateral sides 300, 304 the damaged sides 300, 304, in one embodiment, the ellipses and vectors associated with the reference side femur condyle 302 (e.g., the ellipse 305 of the N2 slice and the vector $U_2$) can be applied to the damaged side femur condyle 300 and damaged side tibia plateau 304 to restore the damaged condyle 300 and damaged plateau 304. Alternatively or additionally, the ellipses and vectors associated with the reference side femur condyle 302 as applied to the reference side tibia plateau 306 (e.g., the ellipse 305 of the N2 slice and the vector $V_2$) can be applied to the damaged side femur condyle 300 and damaged side tibia plateau 304 to restore the damaged condyle 300 and damaged plateau 304. In another embodiment, as can be understood from FIGS. 4C, 4E and 4F, the vectors associated with the reference side tibia plateau 306 (e.g., the vector $V_4$) can be applied to the damaged side femur condyle 300 and damaged side tibia plateau 304 to restore the damaged condyle 300 and damaged plateau 304. Of course, if the conditions of the sides 300, 302, 304, 306 were reversed in FIG. 4F, the identification of the reference sides, the damaged sides, the reference vectors and the application thereof would be reversed from examples given in this paragraph.

Figure 5A:
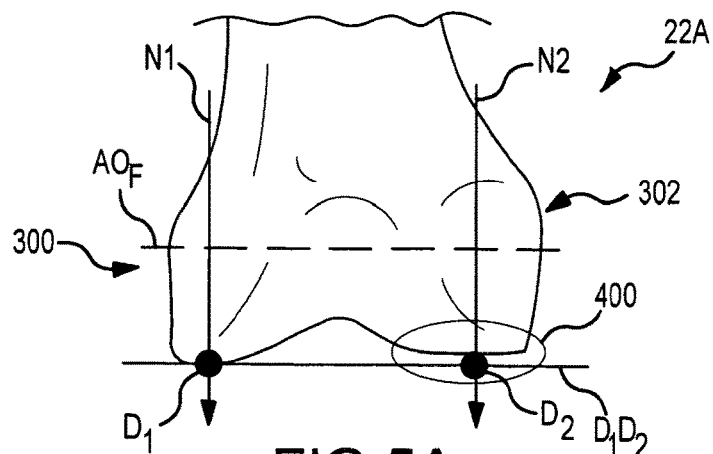
FIG. 5A is a coronal view of a femur bone model.
Figure 5B:
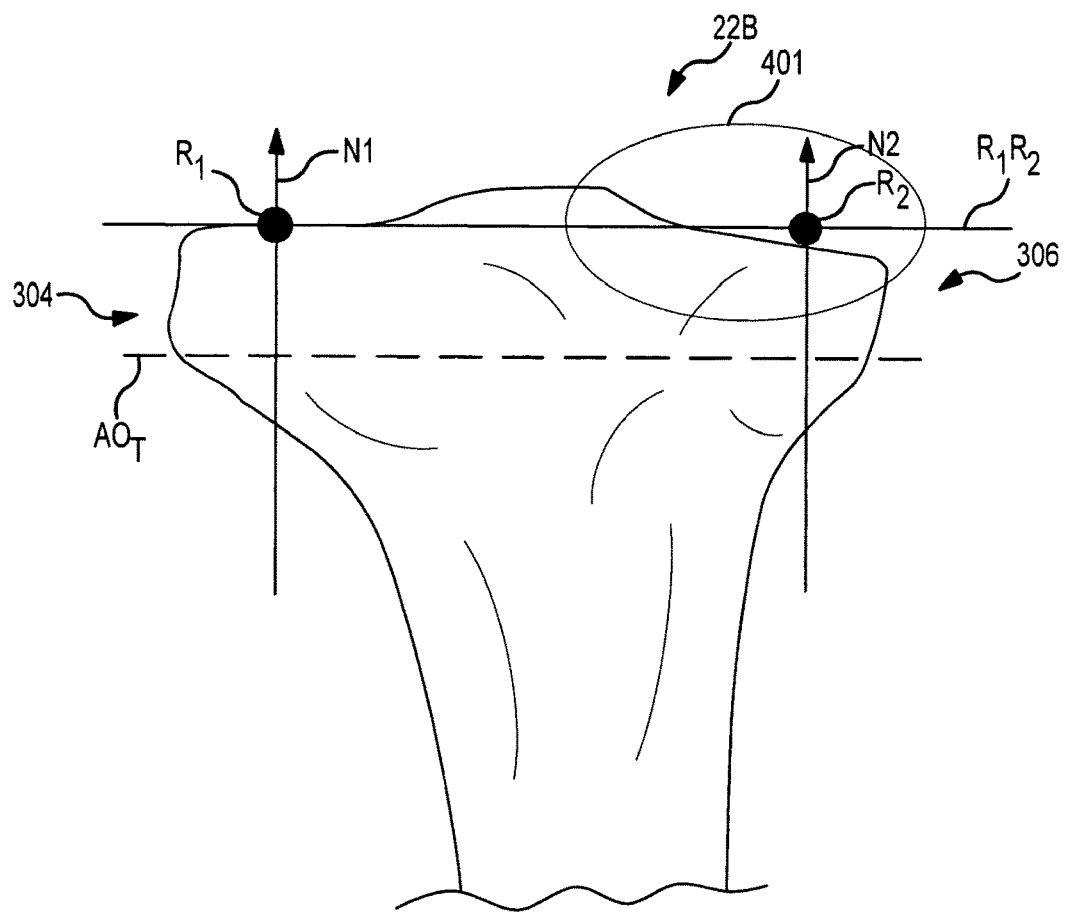
FIG. 5B is a coronal view of a tibia bone model.

1. Employing Vectors from a Femur Condyle of a Reference Side of a Knee Joint to Restore the Femur Condyle and Tibia Plateau of the Damaged Side For a discussion of a first scenario, wherein the medial sides 302, 306 are the damaged sides and the lateral sides 300, 304 are the reference sides, reference is made to FIGS. 5A-5B. FIG. 5A is a coronal view of a femur bone model 22A, and FIG. 5B is a coronal view of a tibia bone model 22B.

As shown in FIG. 5A, the medial femur condyle 302 is deteriorated in region 400 such that the most distal point of the medial condyle 302 fails to intersect point $D_2$ on line $D_1D_2$, which will be corrected once the femur bone model 22A is properly restored to a restored femur bone model 28A such as that depicted in FIG. 3A. As illustrated in FIG. 5B, the medial tibia plateau 306 is deteriorated in region 401 such that the lowest point of the medial plateau 306 fails to intersect point $R_2$ on line $R_1R_2$, which will be corrected once the tibia bone model 22B is properly restored to a restored tibia bone model 28B such as that depicted in FIG. 3C. Because the medial condyle 302 and medial plateau 306 of the bone models 22A, 22B are deteriorated, they will be identified as the damaged sides and targeted for restoration ([block 200] of FIG. 2).

As illustrated in FIG. 5A, the lateral condyle 300 and lateral plateau 304 of the bone models 22A, 22B are in a generally non-deteriorated state, the most distal point $D_1$ of the lateral condyle 300 intersecting line $D_1D_2$, and the lowest point $R_1$ of the lateral plateau 304 intersecting line $R_1R_2$. Because the lateral condyle 300 and lateral plateau 304 of the bone models 22A, 22B are generally in a non-deteriorated state, they will be identified as the reference sides and the source of information used to restore the damaged sides 302, 306 ([block 200] of FIG. 2).

As can be understood from FIGS. 3F, 4A and 5A, for most if not all of the image slices 16 of the lateral condyle 300, image slice information or data such as ellipses and vectors can be determined. For example, an ellipse 305 and vector $U_1$ can be determined for the N1 slice ([block 205] of FIG. 2). The data or information associated with one or more of the various slices 16 of the lateral condyle 300 is applied to or superimposed on one or more image slices 16 of the medial condyle 302 ([block 215] of FIG. 2). For example, as shown in FIG. 5C1, which is an N2 image slice of the medial condyle 302 as taken along the N2 line in FIG. 5A, data or information pertaining to the N1 slice is applied to or superimposed on the N2 image slice to determine the extent of restoration needed in deteriorated region 400. For example, the data or information pertaining to the N1 slice may be in the form of the N1 slice's ellipse 305-N1, vector $U_1$, ellipse axes $P_1'PP_1'$, $D_1DD_1$, etc. The ellipse 305-N1 will inherently contain its major and minor axis information, and the vector $U_1$ of the N1 slice will correspond to the major axis of the 305-N1 ellipse and motion vector of the femur condyles relative to the tibia plateaus. The major axis of the 305-N1 and the vector $U_1$ of the N1 slice are generally parallel to the joint line plane.

In a first embodiment, the N1 slice information may be applied only to the contour line of the N2 slice or another specific slice. In other words, information of a specific reference slice may be applied to a contour line of a single specific damaged slice with which the specific reference slice is coordinated with via manual selection or an algorithm for automatic selection. For example, in one embodiment, the N1 slice information may be manually or automatically coordinated to be applied only to the N2 slice contour line, and the N3 slice information may be manually or automatically coordinated to be applied only to the N4 slice contour line. Other reference side slice information may be similarly coordinated with and applied to other damaged side slice contours in a similar fashion. Coordination between a specific reference slice and a specific damaged slice may be according to various criteria, for example, similarity of the function and/or shape of the bone regions pertaining to the specific reference slice and specific damaged slice and/or similarity of accuracy and dependability for the specific reference slice and specific damaged slice.

In a second embodiment, the N1 slice information or the slice information of another specific slice may be the only image slice used as a reference slice for the contour lines of most, if not all, of the damaged slices. In other words, the N1 image slice information may be the only reference side information used (i.e., to the exclusion of, for example, the N3 image slice information) in the restoration of the contour lines of most, if not each, damaged side image slice (i.e., the N1 image slice information is applied to the contour lines of the N2 and N4 image slices and the N3 image slice information is not used). In such an embodiment, the appropriate single reference image slice may be identified via manual identification or automatic identification via, for example, an algorithm. The identification may be according to certain criteria, such as, for example, which reference image slice is most likely to contain the most accurate and dependable reference information.

While the second embodiment is discussed with respect to information from a single reference image being applied to the contour lines of most, if not all, damaged side image slices, in other embodiments, the reference information applied to the contour lines of the damaged image slices may be from more than one image slice. For example, information from two or more reference image slices (e.g., N1 image slice and N3 image slice) are applied individually to the contour lines of the various damage image slices. In one embodiment, the information from the two or more reference image slices may be combined (e.g., averaged) and the combined information then applied to the contour lines of individual damaged image slices.

In some embodiments, the reference side data or information may include a distal tangent line DTL and a posterior tangent line PTL. The distal tangent line DTL may tangentially intersect the extreme distal point of the reference image slice and be parallel to the major axis of the reference image slice ellipse. For example, with respect to the N1 image slice serving as a reference side image slice, the distal tangent line DTL may tangentially intersect the extreme distal point $D_1$ of the reference N1 image slice and be parallel to the major axis $P_1'PP_1'$ of the reference N1 image slice ellipse 305-N1.

The posterior tangent line PTL may tangentially intersect the extreme posterior point of the reference image slice and be parallel to the major axis of the reference image slice ellipse. For example, with respect to the N1 image slice serving as a reference side image slice, the posterior tangent line PTL may tangentially intersect the extreme posterior point $P_1$ of the reference N1 image slice and be parallel to the minor axis $D_1DD_1$ of the reference N1 image slice ellipse 305-N1.

As can be understood from FIGS. 3F-3I, most, if not all, femur condyle image slices N1, N2, N3, N4 will have an origin $O_1$, $O_2$, $O_3$, $O_4$ associated with the ellipse 305 used to describe or define the condyle surfaces of each slice N1, N2, N3, N4. When these image slices are combined together to form the 3D computer generated bone models 22, the various origins $O_1$, $O_2$, $O_3$, $O_4$ will generally align to form a femur axis $AO_F$ extending medial-lateral through the femur bone model 22A as depicted in FIG. 5A. This axis $AO_F$ can be used to properly orient reference side data (e.g., the ellipse 305-N1 and vector $U_1$ of the N1 slice in the current example) when being superimposed onto a damaged side image slice (e.g., the N2 image slice in the current example). The orientation of the data or information of the reference side does not change as the data or information is being superimposed or otherwise applied to the damaged side image slice. For example, the orientation of the ellipse 305-N1 and vector $U_1$ of the N1 slice is maintained or held constant during the superimposing of such reference information onto the N2 slice such that the reference information does not change with respect to orientation or spatial ratios relative to the femur axis $AO_F$ when being superimposed on or otherwise applied to the N2 slice. Thus, as described in greater detail below, since the reference side information is indexed to the damaged side image slice via the axis $AO_F$ and the orientation of the reference side information does not change in the process of being applied to the damaged side image slice, the reference side information can simply be adjusted with respect to size, if needed and as described below with reference to FIGS. 5C2 and 5C3, to assist in the restoration of the damaged side image slice.

While the reference side information may be positionally indexed relative to the damaged side image slices via the femur reference axis $AO_F$ when being applied to the damaged side image slices, other axes may be used for indexing besides an AO axis that runs through or near the origins of the respective image slice ellipses. For example, a reference axis similar to the femur reference axis $AO_F$ and running medial-lateral may pass through other portions of the femur bone model 22A or outside the femur bone model 22A and may be used to positionally index the reference side information to the respective damaged side image slices.

The contour line $N_2$ of the N2 image slice, as with any contour line of any femur or tibia image slice, may be generated via an open or closed loop computer analysis of the cortical bone of the medial condyle 302 in the N2 image slice, thereby outlining the cortical bone with an open or closed loop contour line $N_2$. Where the contour lines are closed loop, the resulting 3D models 22, 28 will be 3D volumetric models. Where the contour lines are open loop, the resulting 3D models 22, 28 will be 3D surface models.

Figure 5D:
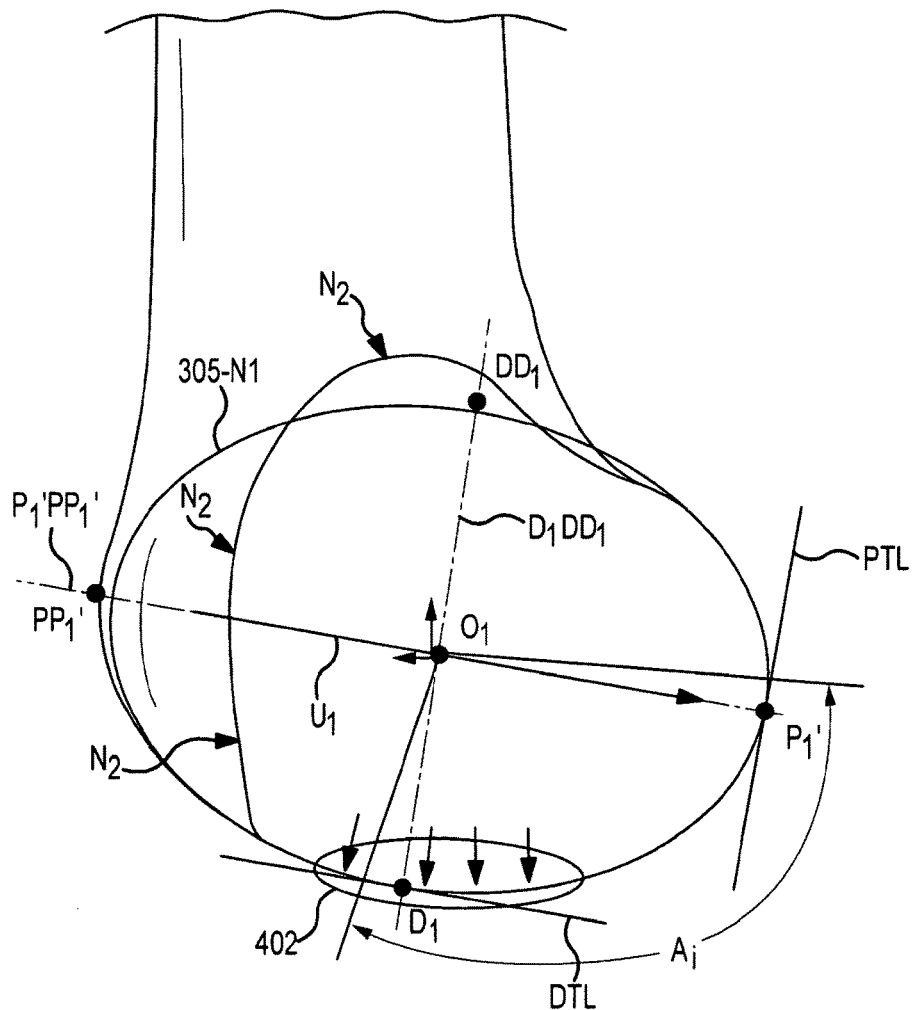
FIG. 5D is the N2 image slice of FIG. 5C1 subsequent to restoration.

While in some cases the reference information from a reference image slice may be substantially similar in characteristics (e.g., size and/or ratios) to the damaged image slice contour line to be simply applied to the contour line, in many cases, the reference information may need to be adjusted with respect to size and/or ratio prior to using the reference information to restore the damaged side contour line as discussed herein with respect to FIGS. 5C1 and 5D. For example, as indicated in FIG. 5C2, which is the same view as FIG. 5C1, except illustrating the reference information is too small relative to the damaged side contour line, the reference information should be increased prior to being used to restore the damaged side contour line. In other words, the N1 information (e.g., the N1 ellipse, vector and tangent lines PTL, DTL), when applied to the contour line of the N2 image slice based on the AO axis discussed above, is too small for at least some of the reference information to match up with at least some of the damaged contour line at the most distal or posterior positions. Accordingly, as can be understood from a comparison of FIGS. 5C1 and 5C2, the N1 information may be increased in size as needed, but maintaining its ratios (e.g., the ratio of the major/minor ellipse axes to each other and the ratios of the offsets of the PTL, DTL from the origin or AO axis), until the N1 information begins to match a boundary of the contour line of the N2 image slice. For example, as depicted in FIG. 5C2, the N1 ellipse is superimposed over the N2 image slice and positionally coordinated with the N2 image slice via the AO axis. The N1 ellipse is smaller than needed to match the contour line of the N2 image slice and is expanded in size until a portion (e.g., the PTL and $P_1'$ of the N1 ellipse) matches a portion (e.g., the most posterior point) of the elliptical contour line of the N2 image slice. A similar process can also be applied to the PTL and DTL, maintaining the ratio of the PTL and DTL relative to the AO axis. As illustrated in FIG. 5C1, the N1 information now corresponds to at least a portion of the damaged image side contour line and can now be used to restore the contour line as discussed below with respect to FIG. 5D.

as indicated in FIG. 5C3, which is the same view as FIG. 5C1, except illustrating the reference information is too large relative to the damaged side contour line, the reference information should be decreased prior to being used to restore the damaged side contour line. In other words, the N1 information (e.g., the N1 ellipse, vector and tangent lines PTL, DTL), when applied to the contour line of the N2 image slice based on the AO axis discussed above, is too large for at least some of the reference information to match up with at least some of the damaged contour line at the most distal or posterior positions. Accordingly, as can be understood from a comparison of FIGS. 5C1 and 5C3, the N1 information may be decreased in size as needed, but maintaining its ratios (e.g., the ratio of the major/minor ellipse axes to each other and the ratios of the offsets of the PTL, DTL from the origin or AO axis), until the N1 information begins to match a boundary of the contour line of the N2 image slice. For example, as depicted in FIG. 5C3, the N1 ellipse is superimposed over the N2 image slice and positionally coordinated with the N2 image slice via the AO axis. The N1 ellipse is larger than needed to match the contour line of the N2 image slice and is reduced in size until a portion (e.g., the PTL and $P_1'$ of the N1 ellipse) matches a portion (e.g., the most posterior point) of the elliptical contour line of the N2 image slice. A similar process can also be applied to the PTL and DTL, maintaining the ratio of the PTL and DTL relative to the AO axis. As illustrated in FIG. 5C1, the N1 information now corresponds to at least a portion of the damaged image side contour line and can now be used to restore the contour line as discussed below with respect to FIG. 5D.

As can be understood from FIG. 5D, which is the N2 image slice of FIG. 5C1 subsequent to restoration, the contour line $N_2$ of the N2 image slice has been extended out to the boundaries of the ellipse 305-N1 in the restored region 402 ([block 220] of FIG. 2). This process of applying information (e.g., ellipses 305 and vectors) from the reference side to the damaged side is repeated slice-by-slice for most, if not all, image slices 16 forming the damaged side of the femur bone model 22A. Once most or all of the image slices 16 of the damaged side have been restored, the image slices used to form the femur bone model 22A, including the recently restored images slices, are recompiled via 3D computer modeling programs into a 3D femur restored bone model 28A similar to that depicted in FIG. 3A ([block 225] of FIG. 2).

As can be understood from FIGS. 5C1 and 5D, in one embodiment, the damaged contour line $N_2$ of the N2 image slice is adjusted based on the ratio of the reference side major axis major axis $P_1'PP_1'$ to the reference side minor axis $D_1DD_1$. In one embodiment, the damaged contour line $N_2$ of the N2 image slice is adjusted based on reference side ellipse 305-N1. Therefore, the damaged contour lines of the damaged side image slices can be assessed to be enlarged according to the ratios pertaining to the ellipses of the reference side image slices.

Depending on the relationship of the joint contour lines of the damaged side image slice relative to the ratios obtained from the reference side information or data, the joint contour lines of the damaged side image slice may be manipulated so the joint contour line is increased along its major axis and/or its minor axis. Depending on the patient's knee shape, the major axis and minor axis of the condyle ellipse varies from person to person. If the major axis is close to the minor axis in the undamaged condyle, then the curvature of the undamaged condyle is close to a round shape. In such configured condyles, in the restoration procedure, the contour of the damaged condyle can be assessed and increased in a constant radius in both the major and minor axis. For condyles of other configurations, such as where the undamaged condyle shows an ellipse contour with a significantly longer major axis as compared to its minor axis, the bone restoration may increase the major axis length in order to modify the damaged condyle contour.

A damaged side tibia plateau can also be restored by applying data or information from the reference side femur condyle to the damaged side tibia plateau. In this continued example, the damaged side tibia plateau will be the medial tibia plateau 306, and the reference side femur condyle will be the lateral femur condyle 300. In one embodiment, the process of restoring the damaged side tibia plateau 306 begins by analyzing the damaged side tibia plateau 306 to determine at least one of a highest anterior point or a highest posterior point of the damaged side tibia plateau 306.

In one embodiment, as can be understood from FIG. 4C as viewed along the N4 image slice and assuming the damage to the medial tibia plateau 306 is not so extensive that at least one of the highest anterior or posterior points Q4, Q4' still exists, the damaged tibia plateau 306 can be analyzed via tangent lines to identify the surviving high point Q4, Q4'. For example, if the damage to the medial tibia plateau 306 was concentrated in the posterior region such that the posterior highest point Q4' no longer existed, the tangent line $T_{Q4}$ could be used to identify the anterior highest point Q4. Similarly, if the damage to the medial tibia plateau 306 was concentrated in the anterior region such that the anterior highest point Q4 no longer existed, the tangent line $T_{Q4'}$ could be used to identify the posterior highest point Q4'. In some embodiments, a vector extending between the highest points Q4, Q4' may be generally perpendicular to the tangent lines $T_{Q4}$, $T_{Q4'}$.

Figure 5E:
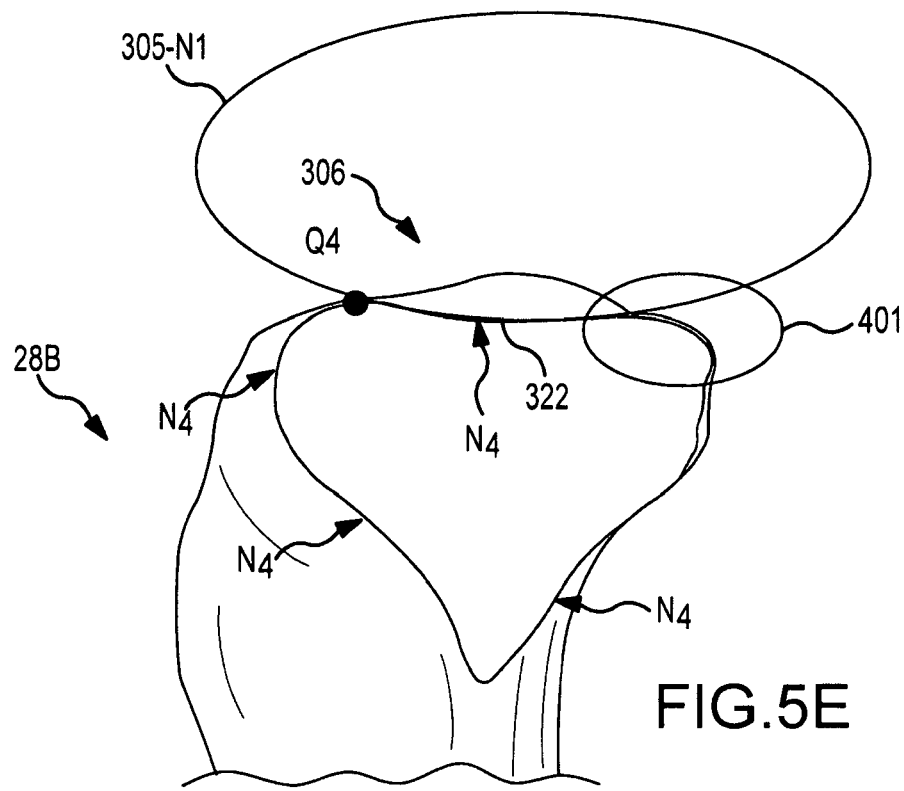
FIG. 5E is a sagittal view of the medial tibia plateau along the N4 image slice, wherein damage to the plateau is mainly in the posterior region.

In another embodiment, the reference side femur condyle ellipse 305-N1 can be applied to the damaged medial tibia plateau 306 to determine at least one of the highest anterior or posterior points Q4, Q4' along the N4 image slice. This process may be performed assuming the damage to the medial tibia plateau 306 is not so extensive that at least one of the highest anterior or posterior points Q4, Q4' still exists. For example, as illustrated by FIG. 5E, which is a sagittal view of the medial tibia plateau 306 along the N4 image slice, wherein damage 401 to the plateau 306 is mainly in the posterior region, the reference side femur condyle ellipse 305-N1 can be applied to the damaged medial tibia plateau 306 to identify the anterior highest point Q4 of the tibia plateau 306. Similarly, in another example, as illustrated by FIG. 5F, which is a sagittal view of the medial tibia plateau 306 along the N4 image slice, wherein damage 401 to the plateau 306 is mainly in the anterior region, the reference side femur condyle ellipse 305-N1 can be applied to the damaged medial tibia plateau 306 to identify the posterior highest point Q4' of the tibia plateau 306.

In one embodiment in a manner similar to that discussed above with respect to FIGS. 5C2 and 5C3, the reference information (e.g., N1 information such as the N1 ellipse) may be applied to the damaged contour line via the AO axis and adjusted in size (e.g., made smaller or larger) until the N1 ellipse matches a portion of the damaged contour line in order to find the highest point, which may be, for example, Q4 or Q4'. As explained above with respect to FIGS. 5C2 and 5C3, the adjustments in size for reference information may be made while maintaining the ratio of the N1 information.

Figure 5F:
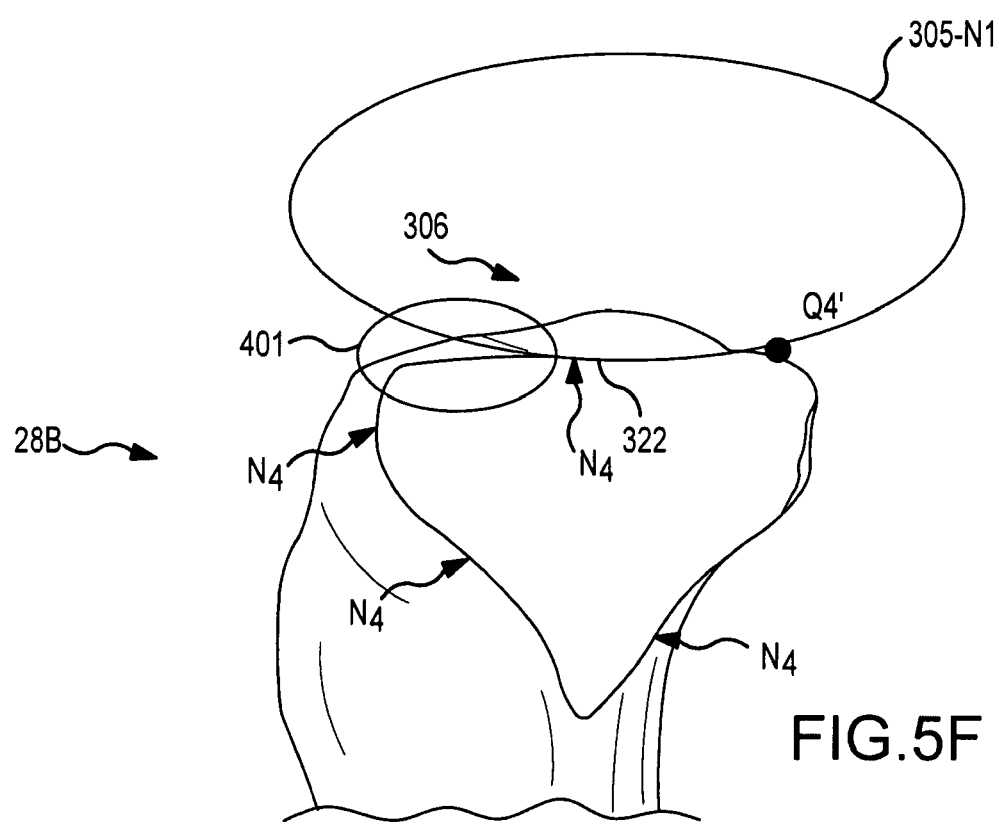
FIG. 5F is a sagittal view of the medial tibia plateau along the N4 image slice, wherein damage to the plateau is mainly in the anterior region.
Figure 5G:
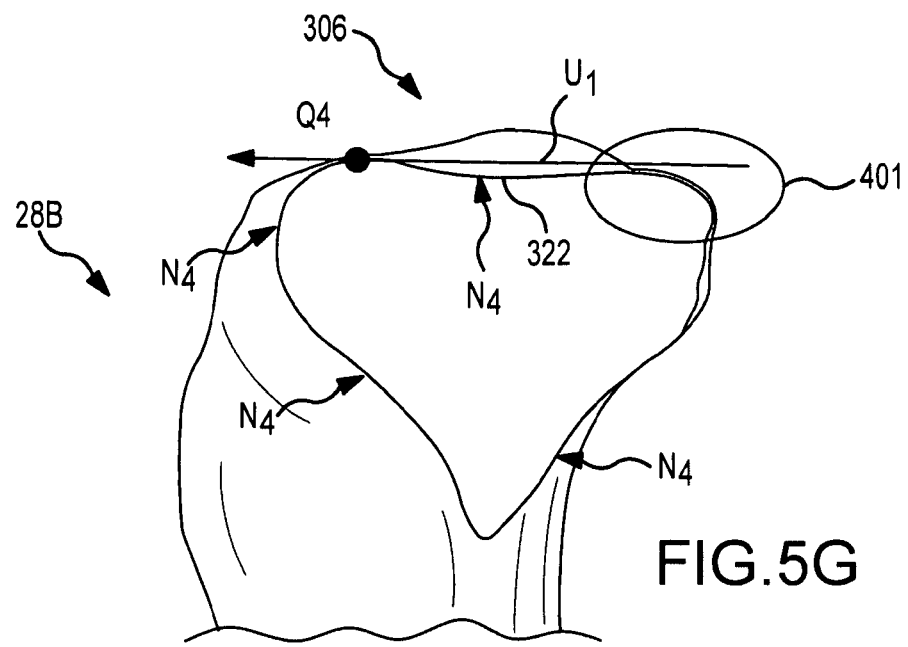
FIG. 5G is the same view as FIG. 5E, except showing the reference side femur condyle vector extending through the anterior highest point of the tibia plateau.
Figure 5H:
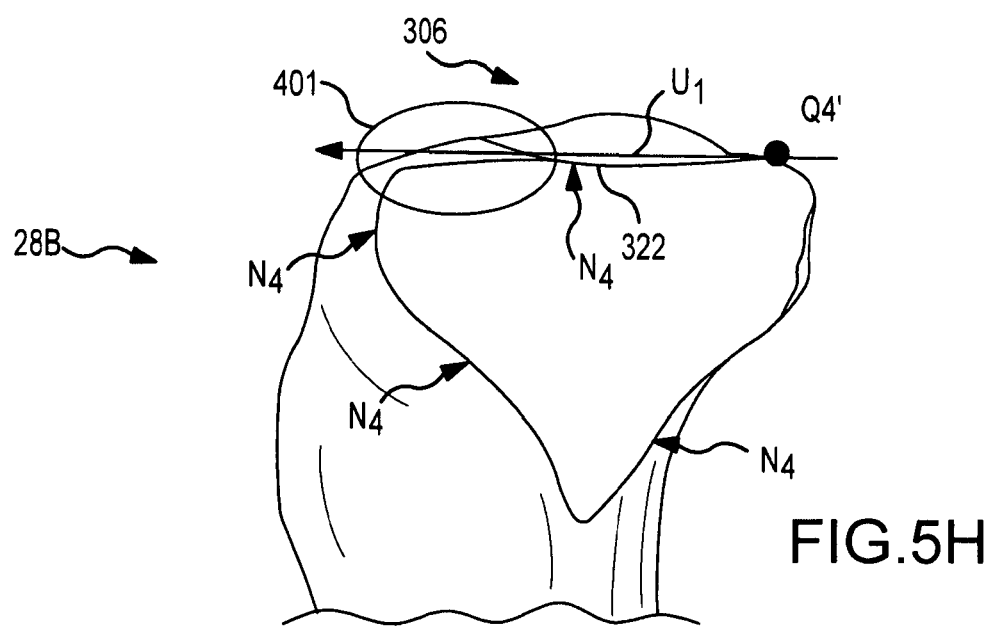
FIG. 5H is the same view as FIG. 5F, except showing the reference side femur condyle vector extending through the posterior highest point of the tibia plateau.

Once the highest point is determined through any of the above-described methods discussed with respect to FIGS. 4C, 5E and 5F, the reference side femur condyle vector can be applied to the damaged side tibia plateau to determine the extent to which the tibia plateau contour line 322 needs to be restored ([block 215] of FIG. 2). For example, as illustrated by FIGS. 5G and 5H, which are respectively the same views as FIGS. 5E and 5F, the vector from the reference side lateral femur condyle 300 (e.g., the vector $U_1$ from the N1 image slice) is applied to the damaged side medial tibia plateau 306 such that the vector $U_1$ intersects the existing highest point. Thus, as shown in FIG. 5G, where the existing highest point is the anterior point Q4, the vector $U_1$ will extend through the anterior point Q4 and will spaced apart from damage 401 in the posterior region of the tibia plateau contour line 322 by the distance the posterior region of the tibia plateau contour line 322 needs to be restored. Similarly, as shown in FIG. 5H, where the existing highest point is the posterior point Q4', the vector $U_1$ will extend through the posterior point Q4' and will spaced apart from the damage 401 of the anterior region of the tibia plateau contour line 322 by the distance the anterior region of the tibia plateau contour line 322 needs to be restored.

Figure 5I:
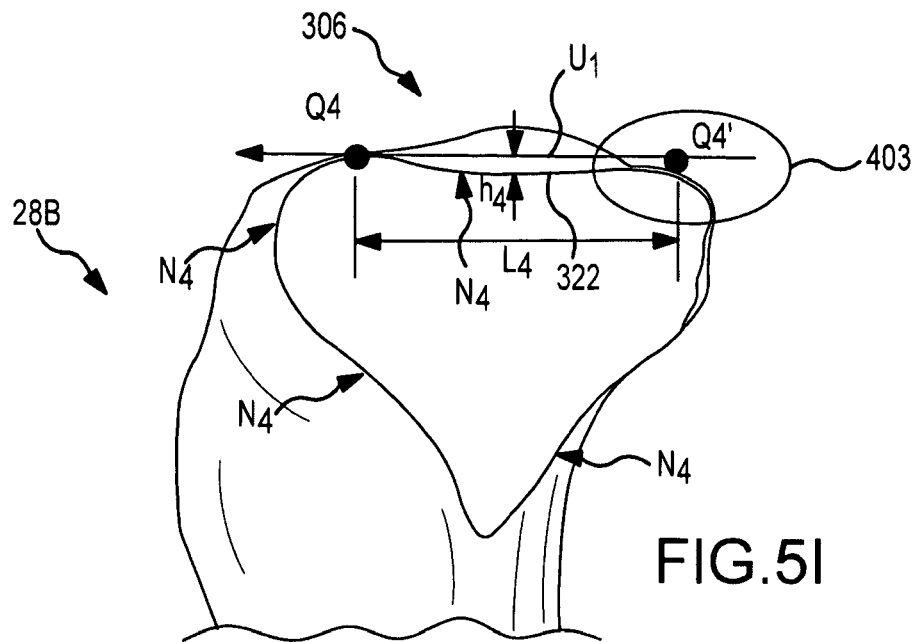
FIG. 5I is the same view as FIG. 5G, except showing the anterior highest point of the tibia plateau restored.
Figure 5J:
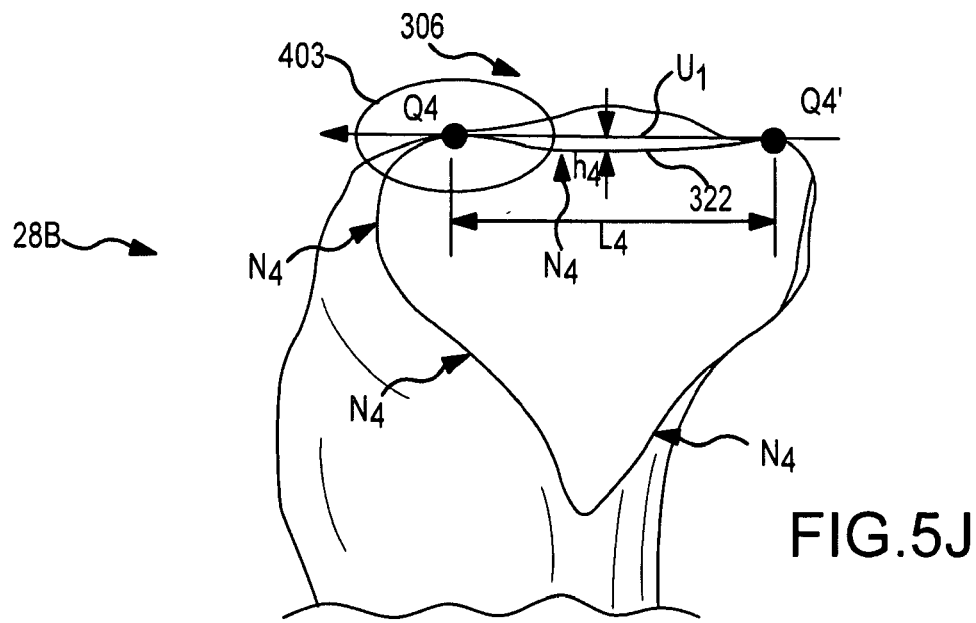
FIG. 5J is the same view as FIG. 5H, except showing the posterior highest point of the tibia plateau restored.

As shown in FIGS. 5I and 5J, which are respectively the same views as FIGS. 5G and 5H, the damaged region 401 of the of the tibia plateau contour line 322 is extended up to intersect the reference vector $U_1$, thereby restoring the missing posterior high point Q4' in the case of FIG. 5I and the anterior high point Q4 in the case of and FIG. 5J, the restoring resulting in restored regions 403. As can be understood from FIGS. 5E, 5F, 5I and 5J, in one embodiment, the reference side femur condyle ellipse 305-N1 may be applied to the damaged side tibia plateau 306 to serve as a guide to locate the proper offset distance $L_4$ between the existing high point (i.e., Q4 in FIG. 5I and Q4' in FIG. 5I) and the newly restored high point (i.e., Q4' in FIG. 5I and Q4 in FIG. 5I) of the restored region 403. Also, in one embodiment, the reference side femur condyle ellipse 305-N1 may be applied to the damaged side tibia plateau 306 to serve as a guide to achieve the proper curvature for the tibia plateau contour line 322. The curvature of the tibia plateau contour line 322 may such that the contour line 322 near the midpoint between the anterior and posterior high points Q4, Q4' is offset from the reference vector $U_1$ by a distance $h_4$. In some embodiments, the ratio of the distances $h_4/L_4$ after the restoration is less than approximately 0.01. As discussed above, the reference ellipse may be applied to the damaged contour line and adjusted in size, but maintaining the ratio, until the ellipse matches a portion of the damaged contour line.

As discussed above with respect to the femur condyle image slices being positionally referenced to each other via a femur reference axis $AO_F$, and as can be understood from FIG. 5B, each tibia image slice N1, N2, N3, N4 will be generated relative to a tibia reference axis $AO_T$, which may be the same as or different from the femur reference axis $AO_F$. The tibia reference axis $AO_T$ will extend medial-lateral and may pass through a center point of each area defined by the contour line of each tibia image slice N1, N2, N3, N4. The tibia reference axis $AO_T$ may extend through other regions of the tibia image slices N1, N2, N3, N4 or may extend outside of the tibia image slices, even, for example, through the origins $O_1$, $O_2$, $O_3$, $O_4$ of the respective femur images slices N1, N2, N3, N4 (in such a case the tibia reference axis $AO_F$ and femur reference axis $AO_F$ may be the same or share the same location).

The axis $AO_T$ can be used to properly orient reference side data (e.g., the ellipse 305-N1 and vector $U_1$ of the N1 slice in the current example) when being superimposed onto a damaged side image slice (e.g., the N4 image slice in the current example). The orientation of the data or information of the reference side does not change as the data or information is being superimposed or otherwise applied to the damaged side image slice. For example, the orientation of the ellipse 305-N1 and vector $U_1$ of the N1 slice is maintained or held constant during the superimposing of such reference information onto the N4 slice such that the reference information does not change when being superimposed on or otherwise applied to the N4 slice. Thus, since the reference side information is indexed to the damaged side image slice via the axis $AO_T$ and the orientation of the reference side information does not change in the process of being applied to the damaged side image slice, the reference side information can simply be adjusted with respect to size to assist in the restoration of the damaged side image slice.

The contour line $N_4$ of the N4 image slice, as with any contour line of any femur or tibia image slice, may be generated via an open or closed loop computer analysis of the cortical bone of the medial tibia plateau 306 in the N4 image slice, thereby outlining the cortical bone with an open or closed loop contour line $N_4$. Where the contour lines are closed loop, the resulting 3D models 22, 28 will be 3D volumetric models. Where the contour lines are open loop, the resulting 3D models 22, 28 will be 3D surface models.

The preceding example discussed with respect to FIGS. 5A-5J is given in the context of the lateral femur condyle 300 serving as the reference side and the medial femur condyle 302 and medial tibia condyle 306 being the damaged sides. Specifically, reference data or information (e.g., ellipses, vectors, etc.) from lateral femur condyle 300 is applied to the medial femur condyle 302 and medial tibia plateau 306 for the restoration thereof. The restoration process for the contour lines of the damaged side femur condyle 302 and damaged side tibia plateau 306 take place slice-by-slice for the image slices 16 forming the damaged side of the bone models 22A, 22B ([block 220] of FIG. 2). The restored image slices 16 are then utilized when a 3D computer modeling program recompiles the image slices 16 to generate the restored bone models 28A, 28B ([block 225] of FIG. 2).

While a specific example is not given to illustrate the reversed situation, wherein the medial femur condyle 302 serves as the reference side and the lateral femur condyle 300 and lateral tibia condyle 304 are the damaged sides, the methodology is the same as discussed with respect to FIGS. 5A-5J and need not be discussed in such great detail. It is sufficient to know that reference data or information (e.g., ellipses, vectors, etc.) from the medial femur condyle 302 is applied to the lateral femur condyle 300 and lateral tibia plateau 304 for the restoration thereof, and the process is the same as discussed with respect to FIGS. 5A-5J.

2. Employing Vectors from a Tibia Plateau of a Reference Side of a Knee Joint to Restore the Tibia Plateau of the Damaged Side A damaged side tibia plateau can also be restored by applying data or information from the reference side tibia plateau to the damaged side tibia plateau. In this example, the damaged side tibia plateau will be the medial tibia plateau 306, and the reference side tibia plateau will be the lateral tibia plateau 304.

In one embodiment, the process of restoring the damaged side tibia plateau 306 begins by analyzing the reference side tibia plateau 304 to determine the highest anterior point and a highest posterior point of the reference side tibia plateau 304. Theses highest points can then be used to determine the reference vector.

In one embodiment, as can be understood from FIG. 4C as viewed along the N3 image slice, the reference side tibia plateau 304 can be analyzed via tangent lines to identify the highest points Q3, Q3'. For example, tangent line $T_{Q3}$ can be used to identify the anterior highest point Q3, and tangent line $T_{Q3'}$ can be used to identify the posterior highest point Q3'. In some embodiments, a vector extending between the highest points Q3, Q3' may be generally perpendicular to the tangent lines $T_{Q3}$, $T_{Q3'}$.

In another embodiment, the reference side femur condyle ellipse 305-N1 can be applied to the reference side lateral tibia plateau 304 to determine the highest anterior or posterior points Q3, Q3' along the N3 image slice. For example, as can be understood from FIG. 4A, the reference side femur condyle ellipse 305-N1 (or ellipse 305-N3 if analyzed in the N3 image slice) can be applied to the reference side lateral tibia plateau 304 to identify the anterior highest point Q1 of the tibia plateau 304, and the reference side femur condyle ellipse 305-N1 (or ellipse 305-N3 if analyzed in the N3 image slice) can be applied to the reference side lateral tibia plateau 304 to identify the posterior highest point Q1' of the tibia plateau 306. Where the ellipse 305-N3 of the N3 image slice is utilized, the highest tibia plateau points may be Q3, Q3'.

As can be understood from FIG. 4A, once the highest points are determined, a reference vector can be determined by extending a vector through the points. For example, vector $V_1$ can be found by extending the vector through highest tibia plateau points Q1, Q1' in the N1 slice.

In one embodiment, the process of restoring the damaged side tibia plateau 306 continues by analyzing the damaged side tibia plateau 306 to determine at least one of a highest anterior point or a highest posterior point of the damaged side tibia plateau 306.

In one embodiment, as can be understood from FIG. 4C as viewed along the N4 image slice and assuming the damage to the medial tibia plateau 306 is not so extensive that at least one of the highest anterior or posterior points Q4, Q4' still exists, the damaged tibia plateau 306 can be analyzed via tangent lines to identify the surviving high point Q4, Q4'. For example, if the damage to the medial tibia plateau 306 was concentrated in the posterior region such that the posterior highest point Q4' no longer existed, the tangent line $T_{Q4}$ could be used to identify the anterior highest point Q4. Similarly, if the damage to the medial tibia plateau 306 was concentrated in the anterior region such that the anterior highest point Q4 no longer existed, the tangent line $T_{Q4'}$ could be used to identify the posterior highest point Q4'.

In another embodiment, the reference side femur condyle ellipse 305-N1 can be applied to the damaged medial tibia plateau 306 to determine at least one of the highest anterior or posterior points Q4, Q4' along the N4 image slice. This process may be performed assuming the damage to the medial tibia plateau 306 is not so extensive that at least one of the highest anterior or posterior points Q4, Q4' still exists. For example, as illustrated by FIG. 5E, which is a sagittal view of the medial tibia plateau 306 along the N4 image slice, wherein damage 401 to the plateau 306 is mainly in the posterior region, the reference side femur condyle ellipse 305-N1 can be applied to the damaged medial tibia plateau 306 to identify the anterior highest point Q4 of the tibia plateau 306. Similarly, in another example, as illustrated by FIG. 5F, which is a sagittal view of the medial tibia plateau 306 along the N4 image slice, wherein damage 401 to the plateau 306 is mainly in the anterior region, the reference side femur condyle ellipse 305-N1 can be applied to the damaged medial tibia plateau 306 to identify the posterior highest point Q4' of the tibia plateau 306.

In one embodiment in a manner similar to that discussed above with respect to FIGS. 5C2 and 5C3, the reference information (e.g., N1 information such as the N1 ellipse) may be applied to the damaged contour line via the AO axis and adjusted in size (e.g., made smaller or larger) until the N1 ellipse matches a portion of the damaged contour line in order to find the highest point, which may be, for example, Q4 or Q4'. As explained above with respect to FIGS. 5C2 and 5C3, the adjustments in size for reference information may be made while maintaining the ratio of the N1 information.

Figure 5K:
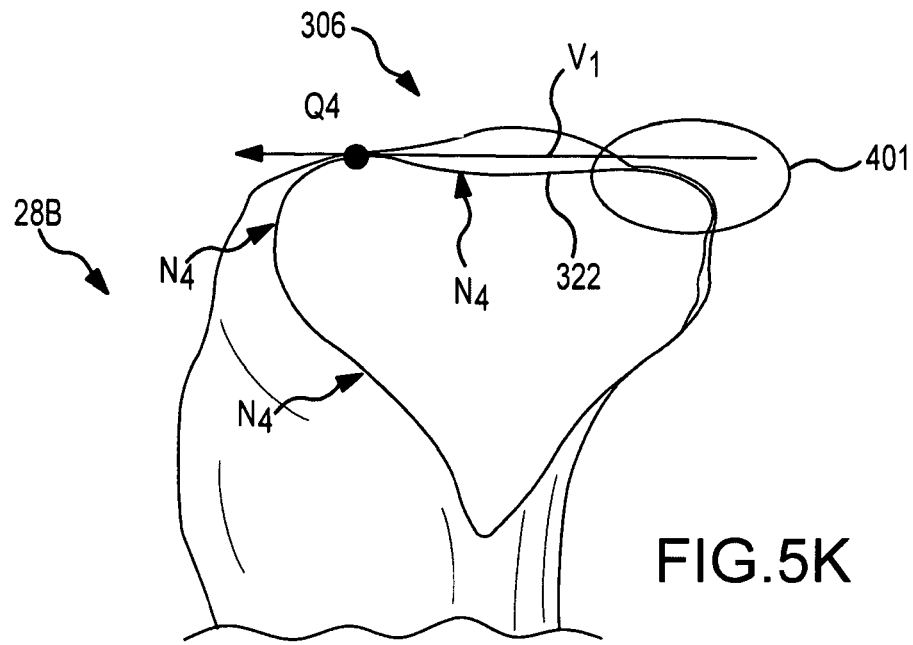
FIG. 5K is the same view as FIG. 5G, except employing reference vector $V_1$ as opposed to $U_1$.
Figure 5L:
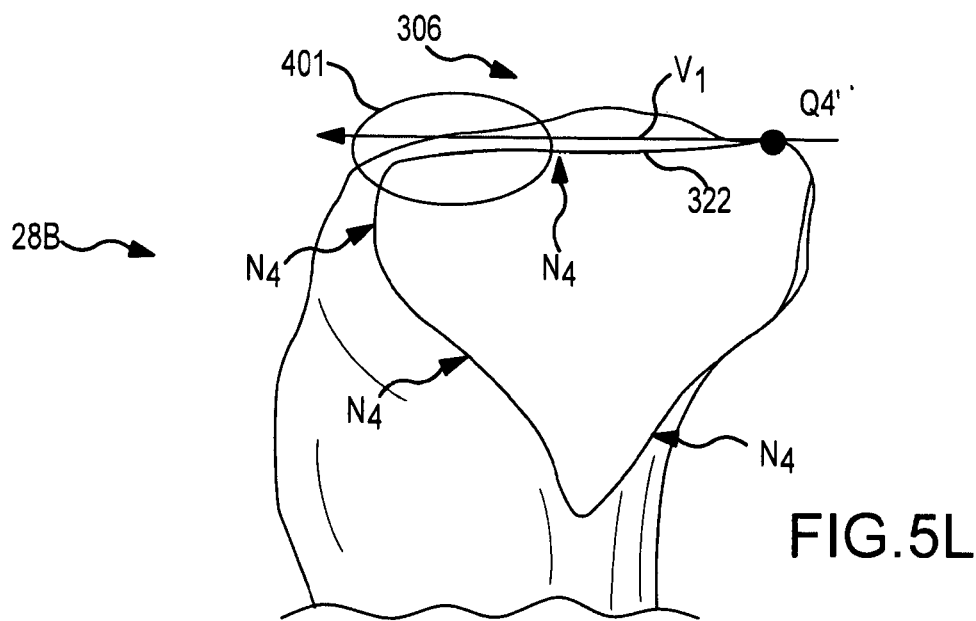
FIG. 5L is the same view as FIG. 5H, except employing reference vector $V_1$ as opposed to $U_1$.

Once the highest point is determined through any of the above-described methods discussed with respect to FIGS. 4C, 5E and 5F, the reference side tibia plateau vector can be applied to the damaged side tibia plateau to determine the extent to which the tibia plateau contour line 322 needs to be restored ([block 215] of FIG. 2). For example, as can be understood from FIGS. 5K and 5L, which are respectively the same views as FIGS. 5G and 5H, the vector from the reference side lateral tibia plateau 304 (e.g., the vector $V_1$ from the N1 image slice) is applied to the damaged side medial tibia plateau 306 such that the vector $V_1$ intersects the existing highest point. Thus, as shown in FIG. 5K, where the existing highest point is the anterior point Q4, the vector $V_1$ will extend through the anterior point Q4 and will spaced apart from damage 401 in the posterior region of the tibia plateau contour line 322 by the distance the posterior region of the tibia plateau contour line 322 needs to be restored. Similarly, as shown in FIG. 5L, where the existing highest point is the posterior point Q4', the vector $V_1$ will extend through the posterior point Q4' and will spaced apart from the damage 401 of the anterior region of the tibia plateau contour line 322 by the distance the anterior region of the tibia plateau contour line 322 needs to be restored.

Figure 5M:
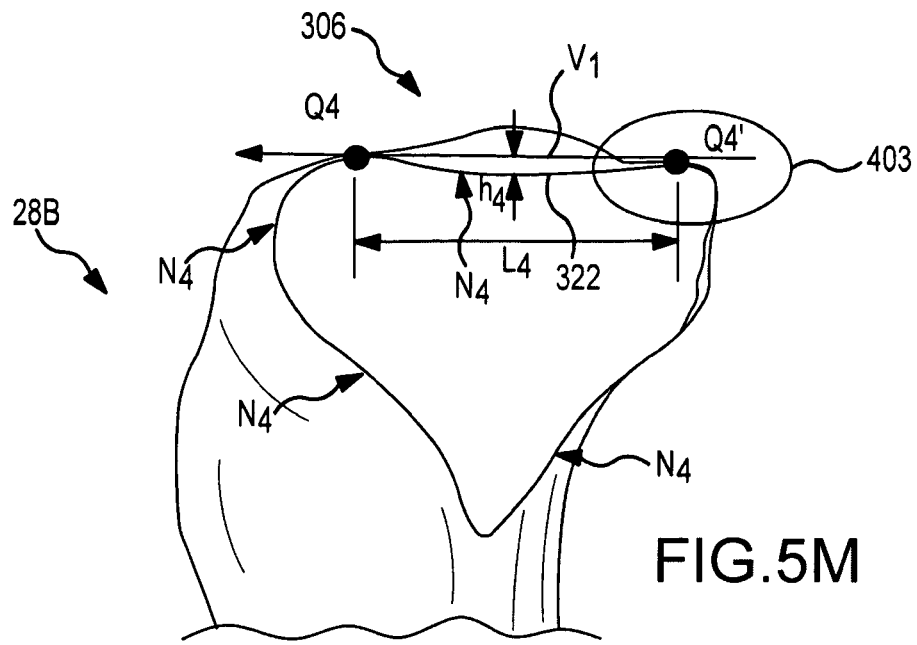
FIG. 5M is the same view as FIG. 5I, except employing reference vector $V_1$ as opposed to $U_1$.
Figure 5N:
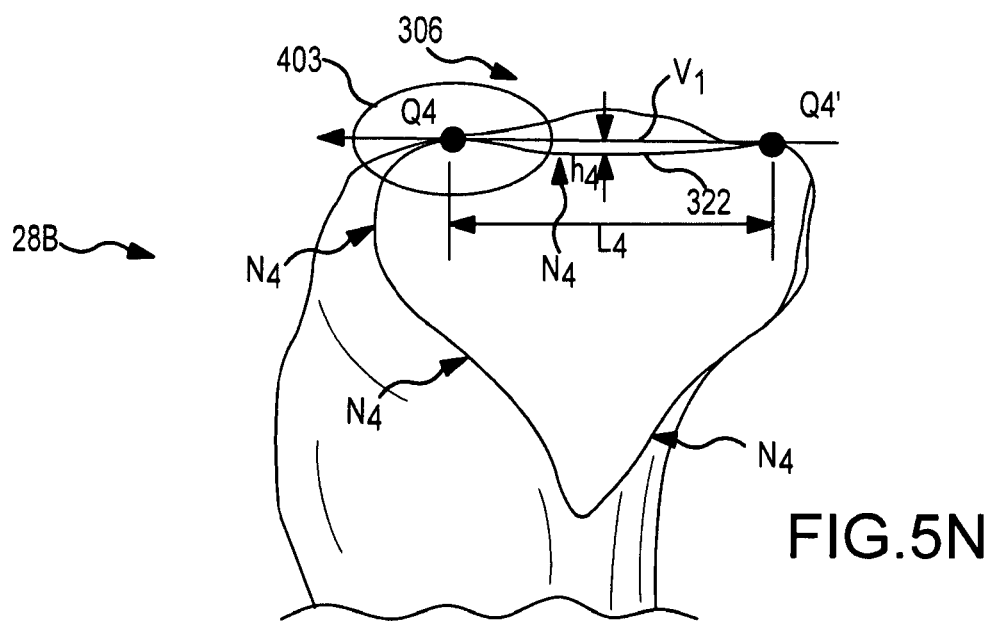
FIG. 5N is the same view as FIG. 5J, except employing reference vector $V_1$ as opposed to $U_1$.

As shown in FIGS. 5M and 5N, which are respectively the same views as FIGS. 5I and 5J, the damaged region 401 of the of the tibia plateau contour line 322 is extended up to intersect the reference vector $V_1$, thereby restoring the missing posterior high point Q4' in the case of FIG. 5M and the anterior high point Q4 in the case of and FIG. 5N, the restoring resulting in restored regions 403. As can be understood from FIGS. 5E, 5F, 5M and 5N, in one embodiment, the reference side femur condyle ellipse 305-N1 may be applied to the damaged side tibia plateau 306 to serve as a guide to locate the proper offset distance $L_4$ between the existing high point (i.e., Q4 in FIG. 5M and Q4' in FIG. 5N) and the newly restored high point (i.e., Q4' in FIG. 5M and Q4 in FIG. 5N) of the restored region 403. Also, in one embodiment, the reference side femur condyle ellipse 305-N1 may be applied to the damaged side tibia plateau 306 to serve as a guide to achieve the proper curvature for the tibia plateau contour line 322. The curvature of the tibia plateau contour line 322 may such that the contour line 322 near the midpoint between the anterior and posterior high points Q4, Q4' is offset from the reference vector $U_1$ by a distance $h_4$. In some embodiments, the ratio of the distances $h_4/L_4$ after the restoration is less than approximately 0.01. As discussed above, the reference ellipse may be applied to the damaged contour line and adjusted in size, but maintaining the ratio, until the ellipse matches a portion of the damaged contour line.

As discussed above with respect to the femur condyle image slices being positionally referenced to each other via a femur reference axis $AO_F$, and as can be understood from FIG. 5B, each tibia image slice N1, N2, N3, N4 will be generated relative to a tibia reference axis $AO_T$, which may be the same as or different from the femur reference axis $AO_F$. The tibia reference axis $AO_T$ will extend medial-lateral and may pass through a center point of each area defined by the contour line of each tibia image slice N1, N2, N3, N4. The tibia reference axis $AO_T$ may extend through other regions of the tibia image slices N1, N2, N3, N4 or may extend outside of the tibia image slices, even, for example, through the origins $O_1$, $O_2$, $O_3$, $O_4$ of the respective femur images slices N1, N2, N3, N4 (in such a case the tibia reference axis $AO_F$ and femur reference axis $AO_F$ may be the same or share the same location).

The axis $AO_T$ can be used to properly orient reference side data (e.g., the ellipse 305-N1 and vector $V_1$ of the N1 slice in the current example) when being superimposed onto a damaged side image slice (e.g., the N4 image slice in the current example). The orientation of the data or information of the reference side does not change as the data or information is being superimposed or otherwise applied to the damaged side image slice. For example, the orientation of the ellipse 305-N1 and vector $V_1$ of the N1 slice is maintained or held constant during the superimposing of such reference information onto the N4 slice such that the reference information does not change when being superimposed on or otherwise applied to the N4 slice. Thus, since the reference side information is indexed to the damaged side image slice via the axis $AO_T$ and the orientation of the reference side information does not change in the process of being applied to the damaged side image slice, the reference side information can simply be adjusted with respect to size to assist in the restoration of the damaged side image slice.

The contour line $N_4$ of the N4 image slice, as with any contour line of any femur or tibia image slice, may be generated via an open or closed loop computer analysis of the cortical bone of the medial tibia plateau 306 in the N4 image slice, thereby outlining the cortical bone with an open or closed loop contour line $N_4$. Where the contour lines are closed loop, the resulting 3D models 22, 28 will be 3D volumetric models. Where the contour lines are open loop, the resulting 3D models 22, 28 will be 3D surface models.

In the current example discussed with respect to FIGS. 5K-5N, the information from the reference side tibia plateau 304 is employed to restore the damaged side tibia plateau 306. However, the information from the reference side femur condyle 300 is still used to restore the damaged side femur condyle 302 as discussed above in the preceding example with respect to FIGS. 5A-5D.

The preceding example discussed with respect to FIGS. 5K-5N is given in the context of the lateral tibia plateau 304 and lateral femur condyle 300 serving as the reference sides and the medial femur condyle 302 and medial tibia condyle 306 being the damaged sides. Specifically, reference data or information (e.g., vectors from the lateral tibia plateau 304 and ellipses, vectors, etc. from the lateral femur condyle 300) are applied to the medial femur condyle 302 and medial tibia plateau 306 for the restoration thereof. The restoration process for the contour lines of the damaged side femur condyle 302 and damaged side tibia plateau 306 take place slice-by-slice for the image slices 16 forming the damaged side of the bone models 22A, 22B ([block 220] of FIG. 2). The restored image slices 16 are then utilized when a 3D computer modeling program recompiles the image slices 16 to generate the restored bone models 28A, 28B ([block 225] of FIG. 2).

While a specific example is not given to illustrate the reversed situation, wherein the medial tibia plateau 306 and medial femur condyle 302 serve as the reference sides and the lateral femur condyle 300 and lateral tibia condyle 304 are the damaged sides, the methodology is the same as discussed with respect to FIGS. 5A-5D and 5K-5N and need not be discussed in such great detail. It is sufficient to know that reference data or information (e.g., ellipses, vectors, etc.) from the medial tibia plateau 306 and medial femur condyle 302 are applied to the lateral femur condyle 300 and lateral tibia plateau 304 for the restoration thereof, and the process is the same as discussed with respect to FIGS. 5A-5D and 5K-5N.

e. Verifying Accuracy of Restored Bone Model

Once the bone models 22A, 22B are restored into restored bone models 28A, 28B as discussed in the preceding sections, the accuracy of the bone restoration process is checked ([block 230] of FIG. 2). Before discussion example methodology of conducting such accuracy checks, the following discussion regarding the kinetics surround a knee joint is provided.

The morphological shape of the distal femur and its relation to the proximal tibia and the patella suggests the kinetics of the knee (e.g., see Eckhoff et al., "Three-Dimensional Mechanics, Kinetics, and Morphology of the Knee in Virtual Reality", JBJS (2005); 87:71-80). The movements that occur at the knee joint are flexion and extension, with some slight amount of rotation in the bent position. During the movement, the points of contact of the femur with the tibia are constantly changing. Thus, in the flexed position (90° knee extension), the hinder part of the articular surface of the tibia is in contact with the rounded back part of the femoral condyles. In the semiflexed position, the middle parts of the tibia facets articulate with the anterior rounded part of the femoral condyles. In the fully extended position (0° knee extension), the anterior and the middle parts of the tibia facets are in contact with the anterior flattened portion of the femoral condyles.

With respect to the patella, in extreme flexion, the inner articular facet rests on the outer part of the internal condyle of the femur. In flexion, the upper part of facets rest on the lower part of the trochlear surface of the femur. In mid-flexion, the middle pair rest on the middle of the trochlear surface. However, in extension, the lower pair of facets on the patella rest on the upper portion of the trochlear surface of the femur. The difference may be described as the shifting of the points of contact of the articulate surface.

The traditional knee replacement studies focus mainly around the tibial-femoral joint. The methods disclosed herein employ the patella in a tri-compartmental joint study by locating the patella groove of the knee. The posterior surface of patella presents a smooth oval articular area divided into two facets by a vertical ridge, the facets forming the medial and lateral parts of the same surface.

The vertical ridge of the posterior patella corresponds to the femoral trochlear groove. In the knee flexion/extension motion movement, the patella normally moves up and down in the femoral trochlear grove along the vertical ridge and generates quadriceps forces on the tibia. The patellofemoral joint and the movement of the femoral condyles play a major role in the primary structure/mechanics across the joint. When the knee is moving and not fully extended, the femoral condyle surfaces bear very high load or forces. In a normal knee, the patella vertical ridge is properly aligned along the femoral trochlear groove so this alignment provides easy force generation in the sliding movement. If the patella is not properly aligned along the trochlear groove or tilted in certain angles, then it is hard to initiate the sliding movement so it causes difficulty with respect to walking. Further, the misaligned axis along the trochlear groove can cause dislocation of the patella on the trochlear groove, and uneven load damage on the patella as well.

The methods disclosed herein for the verification of the accuracy of the bone restoration process employ a "trochlear groove axis" or the "trochlear groove reference plane" as discussed below. This axis or reference plane extend across the lowest extremity of trochlear groove in both the fully-extended and 90° extension of the knee. Moreover, in relation to the joint line, the trochlear groove axis is perpendicular or generally perpendicular to the joint line of the knee.

Because the vertical ridge of the posterior patella is generally straight (vertical) in the sliding motion, the corresponding trochlear groove axis should be straight as well. The trochlear groove axis is applied into the theory that the joint line of the knee is parallel to the ground. In a properly aligned knee or normal knee, the trochlear groove axis is presumed to be perpendicular or nearly perpendicular to the joint line.

For the OA, rarely is there bone damage in the trochlear groove, typically only cartilage damage. Thus, the femoral trochlear groove can serve as a reliable bone axis reference for the verification of the accuracy of the bone restoration when restoring a bone model 22 into a restored bone model 28.

Figure 6A:
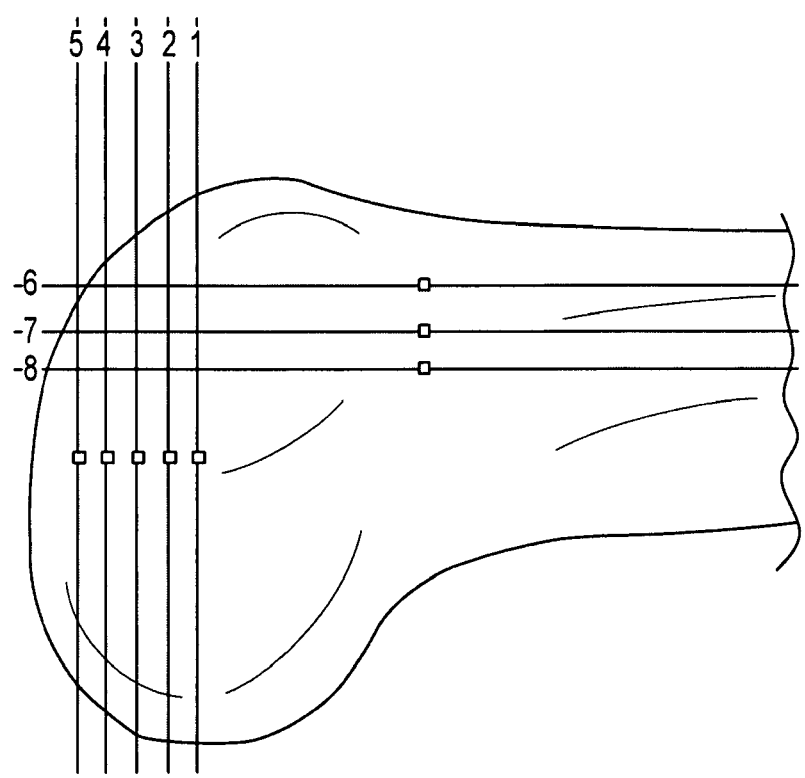
FIG. 6A is a sagittal view of a femur restored bone model illustrating the orders and orientations of imaging slices (e.g., MRI slices, CT slices, etc.) forming the femur restored bone model.
Figures 6B, 6C:
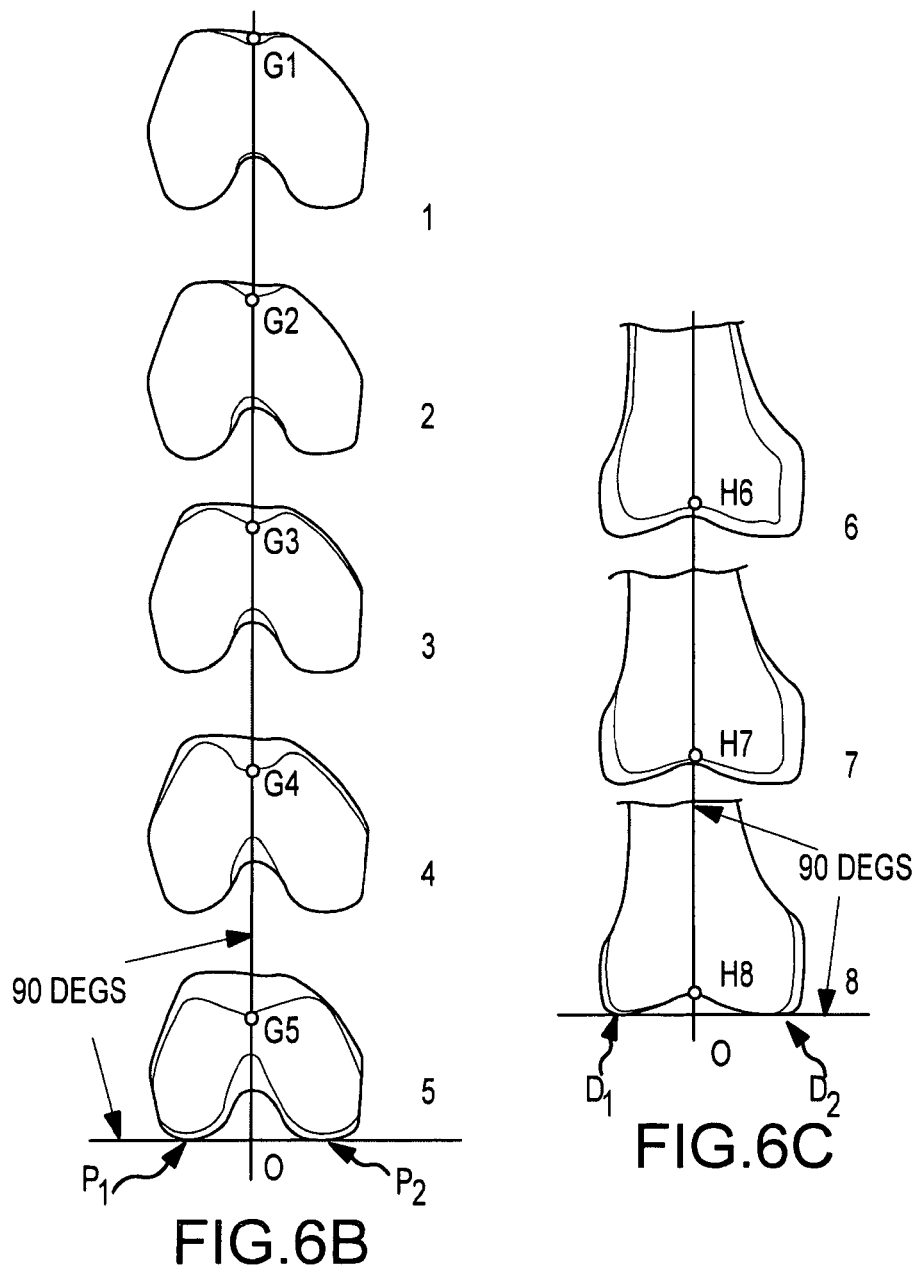
FIG. 6B is the distal images slices 1-5 taken along section lines 1-5 of the femur restored bone model in FIG. 6A.
FIG. 6C is the coronal images slices 6-8 taken along section lines 6-8 of the femur restored bone model in FIG. 6A.
Figure 6D:
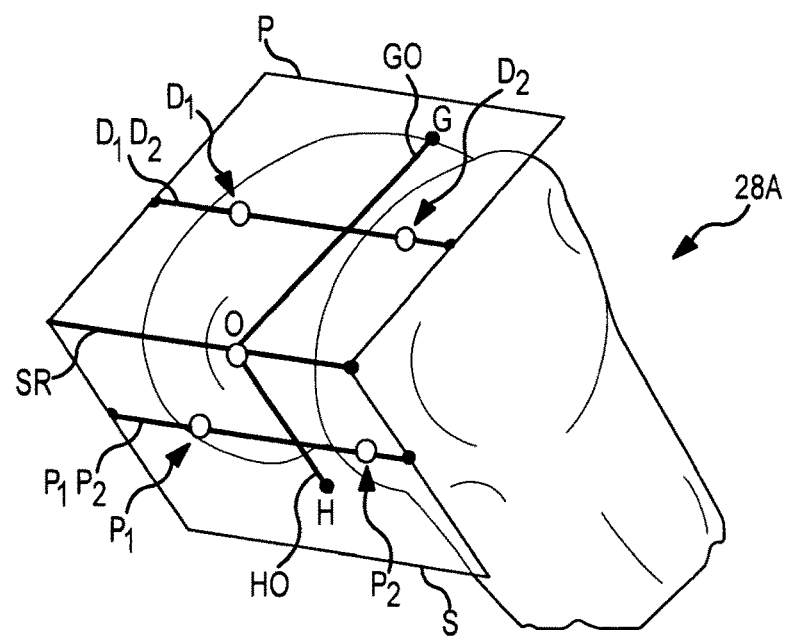
FIG. 6D is a perspective view of the distal end of the femur restored bone model.

For a detailed discussion of the methods for verifying the accuracy of the bone restoration process, reference is made to FIGS. 6A-6D. FIG. 6A is a sagittal view of a femur restored bone model 28A illustrating the orders and orientations of imaging slices 16 (e.g., MRI slices, CT slices, etc.) forming the femur restored bone model 28A. FIG. 6B is the distal images slices 1-5 taken along section lines 1-5 of the femur restored bone model 28A in FIG. 6A. FIG. 6C is the coronal images slices 6-8 taken along section lines 6-8 of the femur restored bone model 28A in FIG. 6A. FIG. 6D is a perspective view of the distal end of the femur restored bone model 28A.

As shown in FIG. 6A, a multitude of image slices are compiled into the femur restored bone model 28A from the image slices originally forming the femur bone model 22A and those restored image slices modified via the above-described methods. Image slices may extend medial-lateral in planes that would be normal to the longitudinal axis of the femur, such as image slices 1-5. Image slices may extend medial-lateral in planes that would be parallel to the longitudinal axis of the femur, such as image slices 6-8. The number of image slices may vary from 1-50 and may be spaced apart in a 2 mm spacing.

As shown in FIG. 6B, each of the slices 1-5 can be aligned vertically along the trochlear groove, wherein points G1, G2, G3, G4, G5 respectively represent the lowest extremity of trochlear groove for each slice 1-5. By connecting the various points G1, G2, G3, G4, G5, a point O can be obtained. As can be understood from FIGS. 3B and 6D, resulting line GO is perpendicular or nearly perpendicular to tangent line $P_1P_2$. In a 90° knee extension in FIG. 3B, line GO is perpendicular or nearly perpendicular to the joint line of the knee and line $P_1P_2$.

As shown in FIG. 6C, each of the slices 6-8 can be aligned vertically along the trochlear groove, wherein points H6, H7, H8 respectively represent the lowest extremity of the trochlear groove for each slice 6-8. By connecting the various points H6, H7, H8, the point O can again be obtained. As can be understood from FIGS. 3A and 6D, resulting line HO is perpendicular or nearly perpendicular to tangent line $D_1D_2$. In a 0° knee extension in FIG. 3A, line HO is perpendicular or nearly perpendicular to the joint line of the knee and line $D_1D_2$.

As illustrated in FIG. 6D, the verification of the accuracy of the restoration process includes determining if the reference lines GO and HO are within certain tolerances with respect to being parallel to certain lines and perpendicular to certain lines. The line GO, as the reference across the most distal extremity of the trochlear groove of the femur and in a 90° knee extension, should be perpendicular to tangent line $D_1D_2$ The line HO, as the reference across the most posterior extremity of trochlear groove of the femur and in a 0° knee extension, should be perpendicular to tangent line $P_1P_2$.

Line HO and line $P_1P_2$ may form a plane S, and lines GO and line $D_1D_2$ may form a plane P that is perpendicular to plane S and forms line SR therewith. Line HO and line GO are parallel or nearly parallel to each other. Lines $P_1P_2$, $D_1D_2$ and SR are parallel or nearly parallel to each other. Lines $P_1P_2$, $D_1D_2$ and SR are perpendicular or nearly perpendicular to lines HO and GO.

As can be understood from FIG. 6D, in one embodiment, lines HO and GO must be within approximately three degrees of being perpendicular with lines $P_1P_2$, and $D_1D_2$ or the restored bones models 28A, 28B will be rejected and the restoration process will have to be repeated until the resulting restored bone models 28A, 28B meet the stated tolerances, or there has been multiple failed attempts to meet the tolerances ([block 230] [block 240] of FIG. 2). Alternatively, as can be understood from FIG. 6D, in another embodiment, lines HO and GO must be within approximately six degrees of being perpendicular with lines $P_1P_2$, and $D_1D_2$ or the restored bones models 28A, 28B will be rejected and the restoration process will have to be repeated until the resulting restored bone models 28A, 28B meet the stated tolerances, or there has been multiple failed attempts to meet the tolerances ([block 230]-[block 240] of FIG. 2). If multiple attempts to provide restored bone models 28A, 28B satisfying the tolerances have been made without success, then bone restoration reference data may be obtained from another similar joint that is sufficiently free of deterioration. For example, in the context of knees, if repeated attempts have been made without success to restore a right knee medial femur condyle and tibia plateau from reference information obtained from the right knee lateral sides, then reference data could be obtained from the left knee lateral or medial sides for use in the restoration process in a manner similar to described above.

In some embodiments, as depicted in the table illustrated in FIG. 7, some OA knee conditions are more likely to be restored via the methods disclosed herein than other conditions when it comes to obtaining the reference data from the same knee as being restored via the reference data. For example, the damaged side of the knee may be light (e.g., no bone damage or bone damage less than 1 mm), medium (e.g., bone damage of approximately 1 mm) or severe (e.g., bone damage of greater than 1 mm). As can be understood from FIG. 7, the bone restoration provided via some of the above-described embodiments may apply to most OA patients having light-damaged knees and medium-damaged knees and some OA patients having severe-damaged knees, wherein restoration data is obtained from a reference side of the knee having the damaged side to be restored. However, for most OA patients having severe-damaged and some OA patients having medium-damaged knees, in some embodiments as described below, bone restoration analysis entails obtaining restoration data from a good first knee of the patient for application to, and restoration of, a bad second knee of the patient.

It should be understood that the indications represented in the table of FIG. 7 are generalities for some embodiments disclosed herein with respect to some patients and should not be considered as absolute indications of success or failure with respect to whether or not any one or more of the embodiments disclosed herein may be successfully applied to an individual patient having any one of the conditions (light, medium, severe) reflected in the table of FIG. 7. Therefore, the table of FIG. 7 should not be considered to limit any of the embodiments disclose herein.

f. Further Discussion of Bone Model Restoration Methods

Figure 8A:
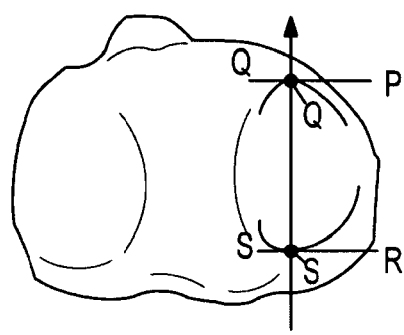
FIGS. 8A-8D are various views of the tibia plateau with reference to restoration of a side thereof.

For further discussion regarding embodiments of bone model restoration methods, reference is made to FIGS. 8A-8D. FIG. 8A shows the construction of reference line SQ in a medial portion of the tibia plateau. In one embodiment, the reference line SQ may be determined by superimposing an undamaged femoral condyle ellipse onto the medial tibia plateau to obtain two tangent points Q and S. In another embodiment, the tangent points Q and S may be located from the image slices by identifying the highest points at the posterior and anterior edges of the medial tibia plateau. By identifying tangent points Q and S, the tangent lines QP and SR may be determined by extending lines across each of the tangent points Q and S, wherein the tangent lines QP and SR are respectively tangent to the anterior and posterior curves of the medial tibia plateau. Reference line SQ may be obtained where tangent line QP is perpendicular or generally perpendicular to reference line SQ and tangent line SR is perpendicular or generally perpendicular to reference line SQ.

Figure 8B:
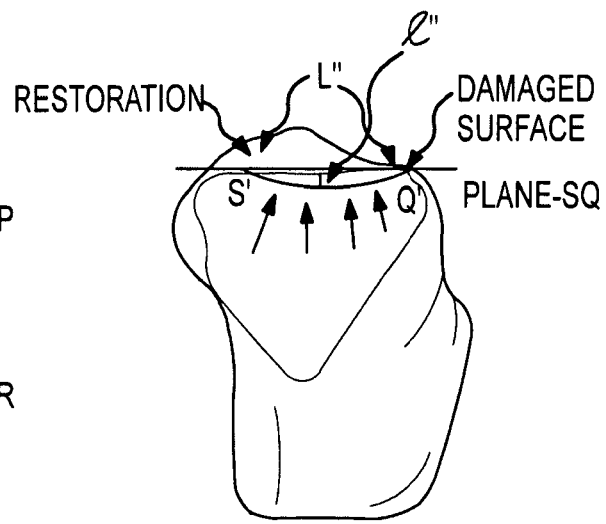

FIG. 8B shows the restoration of a damaged anterior portion of the lateral tibia plateau. The reference vector line or the vector plane is obtained from FIG. 8A, as line SQ or plane SQ. The reference vector plane SQ from the medial side may be applied as the reference plane in the damaged lateral side of the tibia plateau surface. In FIG. 8B, the contour of the damaged anterior portion of the lateral tibia plateau may be adjusted to touch the proximity of the reference vector plane SQ from the undamaged medial side. That is, points S' and Q' are adjusted to reach the proximity of the plane SQ. The outline between points S' and Q' are adjusted and raised to the reference plane SQ. By doing this adjustment, a restored tangent point Q' may be obtained via this vector plane SQ reference.

Figure 8C:
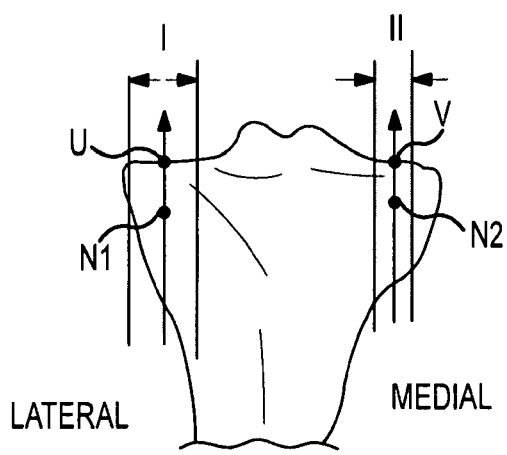
Figure 8D:
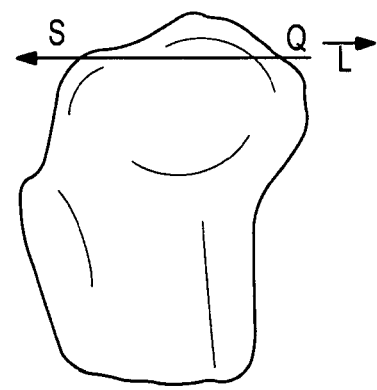

As shown in FIG. 8D, the reference vector plane SQ in the medial side is parallel or nearly parallel to the restored vector plane S'Q' in the lateral side. In FIG. 8B, the length L" represents the length of line S'Q'. The length l" is the offset from the recessed surface region of the tibia plateau to the plane S'Q' after the restoration. In the bone restoration assessment, the ratio of l"/L" may be controlled to be less than 0.01.

FIG. 8C is the coronal view of the restored tibia after 3D reconstruction, with a 0° knee extension model. The points U and V represent the lowest extremity of tangent contact points on each of the lateral and medial tibia plateau, respectively. In one embodiment, tangent points U and V are located within the region between the tibia spine and the medial and lateral epicondyle edges of the tibia plateau, where the slopes of tangent lines in this region are steady and constant. In one embodiment, the tangent point U in the lateral plateau is in area I between the lateral side of lateral intercondylar tubercle to the attachment of the lateral collateral ligament. For the medial portion, the tangent point V is in area II between the medial side of medial intercondylar tubercle to the medial condyle of tibia, as shown in FIG. 8C.

As previously stated, FIG. 8C represents the restored tibia models and, therefore, the reference lines N1 and N2 can apply to the restored tibia model in FIG. 8C, when the knee is at 0° extension. As can be understood from FIG. 8C, line N1 when extended across point U is perpendicular or generally perpendicular to line-UV, while line N2 when extended across point V is perpendicular or generally perpendicular to line UV. In restored the tibia model, line UV may be parallel or nearly parallel to the joint line of the knee. Within all these reference lines, in one embodiment, the tolerable range of the acute angle between nearly perpendicular or nearly parallel lines or planes may be within an absolute 6-degree angle, |X~X'|≤6°. If the acute angle difference from FIG. 8C is less than 6°, the numerical data for the femur and/or tibia restoration is acceptable. This data may be transferred to the further assess the varus/valgus alignment of the knee models.

Figure 9A:
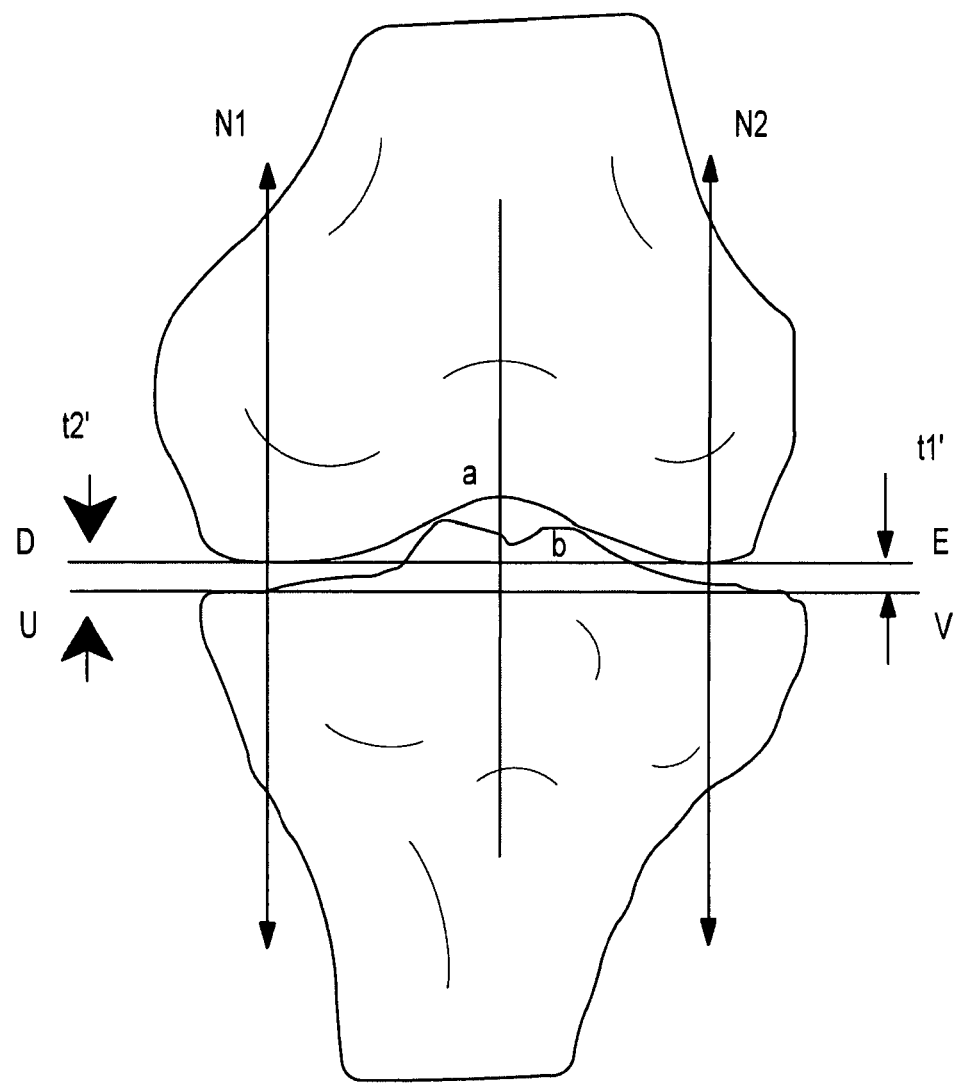
FIGS. 9A and 9B are, respectively, coronal and sagittal views of the restored bone models.

FIG. 9A is a coronal view of the restored knee models of proximal femur and distal tibia with 0° extension of the knee. Line ab extends across the lowest extremity of trochlear groove of the distal femur model. Reference lines N1 and N2 are applied to the restored knee model of varus/valgus alignment, where line-N1 is parallel or generally parallel to line N2 and line ab. Depending on the embodiment, the acute angles between these lines may be controlled within a 3 degree range or a 5 degree range. The tangent points D and E represent the lowest extremities of the restored proximal femur model. The tangent points U and V are obtained from the restored distal tibia plateau surface. In the medial portion, t1' represents the offset of the tangent lines between the medial condyle and medial tibia plateau. In the lateral portion, t2' represents the offset of the tangent lines between the lateral condyle and lateral tibia plateau. In the varus/valgus rotation and alignment, t1' is substantially equal to t2', or |t1'−t2'|<<1 mm. Therefore, line DE may be generally parallel to the joint line of the knee and generally parallel to line UV.

Figure 9B:
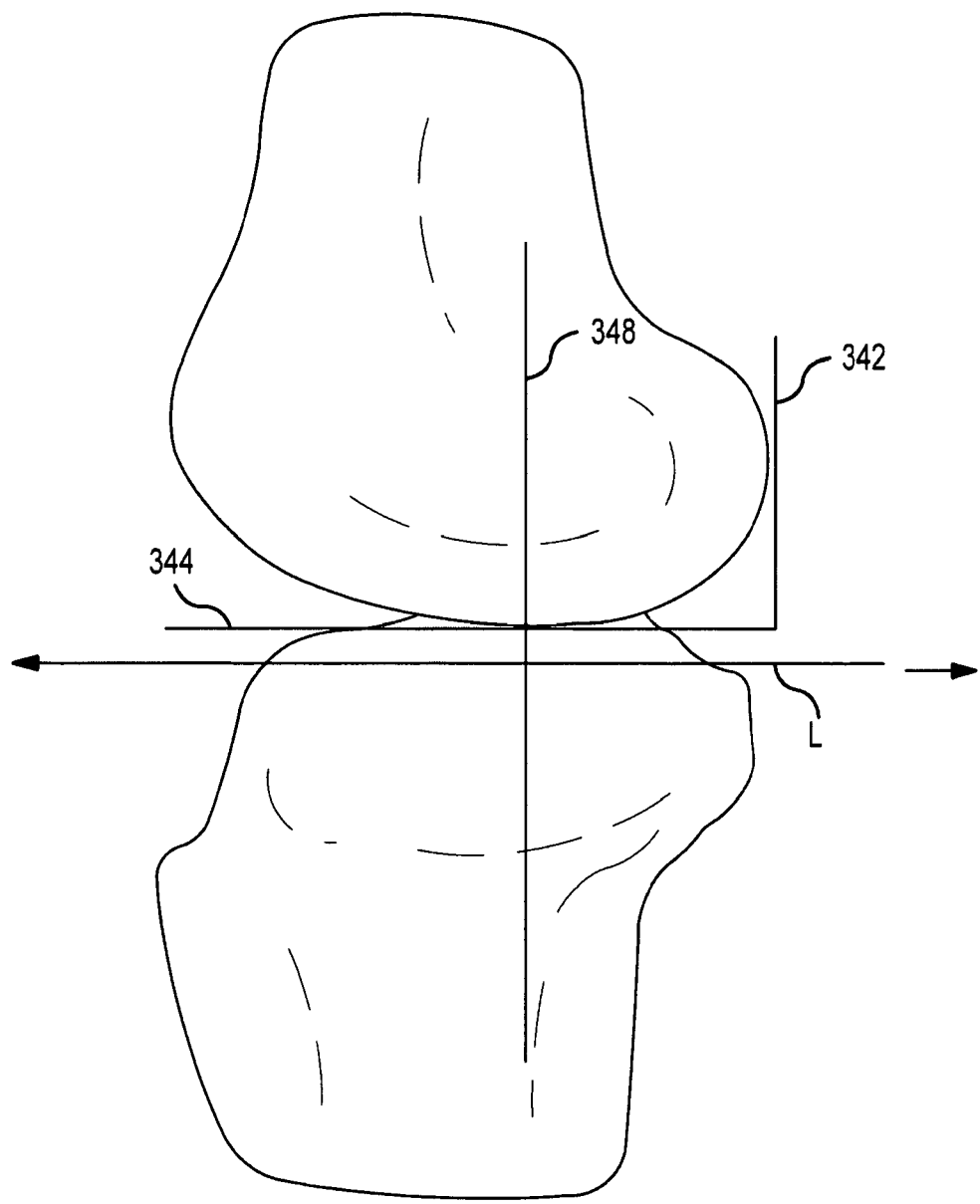

FIG. 9B is a sagittal view of the restored knee models. Line 348 represents the attachment location of lateral collateral ligament which lies on the lateral side of the joint. Line 342 represents the posterior extremity portion of the lateral femoral condyle. Line 344 represents the distal extremity portion of the lateral condyle. In this restored knee model, line 344 may be parallel or generally parallel to line L. That is, plane 344 is parallel or generally parallel to plane L and parallel or generally parallel to the joint plane of the knee. In one embodiment, the tolerable range of acute angle between these planes may be controlled within an absolute 6 degrees. If the angle is less than an absolute 6 degrees, the information of the femur and tibia model will then be forwarded to the preoperative design for the implant modeling. If the acute angle is equal or larger than an absolute 6 degrees, the images and 3D models will be rejected. In this situation, the procedure will be returned to start all over from the assessment procedure of reference lines/planes.

g. Using Reference Information from a Good Joint to Create a Restored Bone Model for a Damaged Joint As mentioned above with respect to the table of FIG. 7, the knee that is the target of the arthroplasty procedure may be sufficiently damaged on both the medial and lateral sides such that neither side may adequately serve as a reference side for the restoration of the other side. In a first embodiment and in a manner similar to that discussed above with respect to FIGS. 2-6D, reference data for the restoration of the deteriorated side of the target knee may be obtained from the patient's other knee, which is often a healthy knee or at least has a healthy side from which to obtain reference information. In a second embodiment, the image slices of the healthy knee are reversed in a mirrored orientation and compiled into a restored bone model representative of the deteriorated knee prior to deterioration, assuming the patient's two knees where generally mirror images of each other when they were both healthy. These two embodiments, which are discussed below in greater detail, may be employed when the knee targeted for arthroplasty is sufficiently damaged to preclude restoration in a manner similar to that described above with respect to FIGS. 2-6D. However, it should be noted that the two embodiments discussed below may also be used in place of, or in addition to, the methods discussed above with respect to FIGS. 2-6D, even if the knee targeted for arthroplasty has a side that is sufficiently healthy to allow the methods discussed above with respect to FIGS. 2-6D to be employed.

Figure 10A:
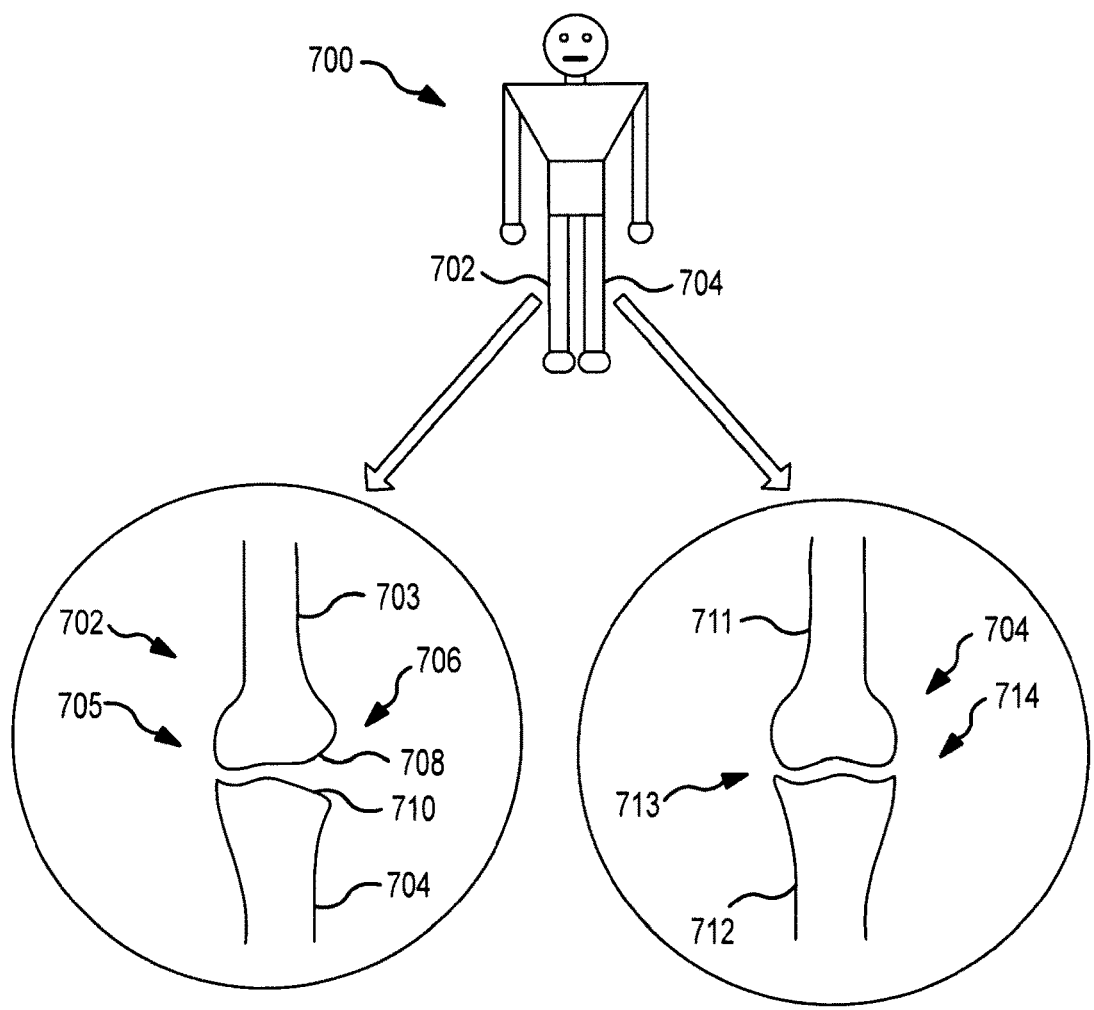
FIG. 10A is a diagram illustrating the condition of a patient's right knee, which is in a deteriorated state, and left knee, which is generally healthy.
Figure 10B:
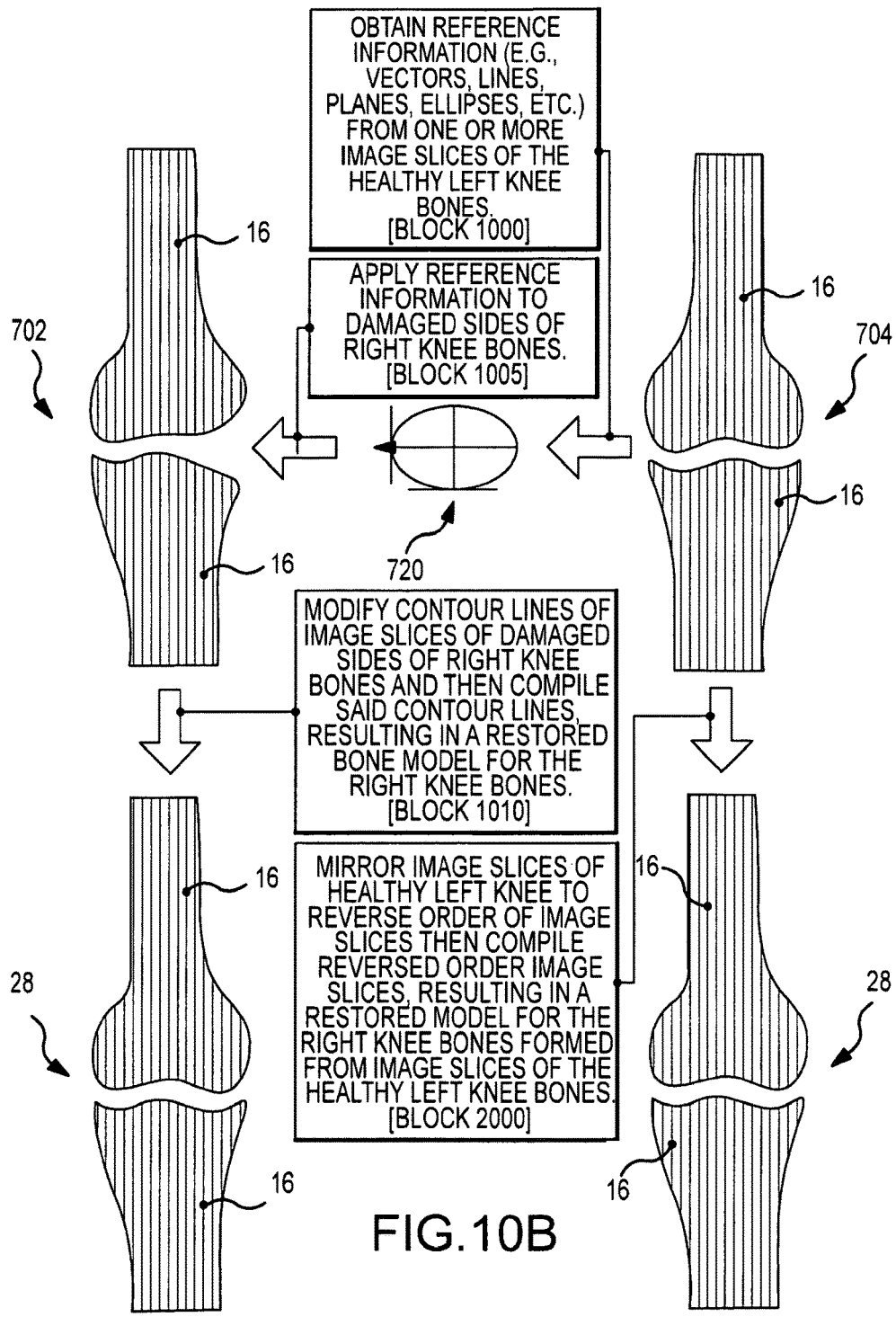
FIG. 10B is a diagram illustrating two options for creating a restored bone model for a deteriorated right knee from image slices obtained from a healthy left knee.

For a discussion of the two embodiments for creating a restored bone model for a deteriorated knee targeted for arthroplasty from image slices obtained from a healthy knee, reference is made to FIGS. 10A and 10B. FIG. 10A is a diagram illustrating the condition of a patient's right knee, which is in a deteriorated state, and left knee, which is generally healthy. FIG. 10B is a diagram illustrating the two embodiments. While in FIGS. 10A and 10B and the following discussion the right knee 702 of the patient 700 is designated as the deteriorate knee 702 and the left knee 704 of the patient 700 is designated as the healthy knee 704, of course such designations are for example purposes only and the conditions of the knees could be the reverse.

As indicated in FIG. 10A, the patient 700 has a deteriorated right knee 702 formed of a femur 703 and a tibia 707 and which has one or both of sides in a deteriorated condition. In this example, the lateral side 705 of the right knee 702 is generally healthy and the medial side 706 of the right knee 702 is deteriorated such that the right medial condyle 708 and right medial tibia plateau 710 will need to be restored in any resulting restored bone model 28. As can be understood from FIG. 10A, the patient also has a left knee 704 that is also formed of a femur 711 and a tibia 712 and which has a medial side 713 and a lateral side 714. In FIG. 10A, both sides 713, 714 of the left knee 704 are generally healthy, although, for one of the following embodiments, a single healthy side is sufficient to generate a restored bone model 28 for the right knee 702.

As indicated in FIG. 10B, image slices 16 of the deteriorated right knee 702 and healthy left knee 704 are generated as discussed above with respect to FIGS. 1A and 1B. In the first embodiment, which is similar to the process discussed above with respect to FIGS. 2-6D, except the process takes place with a deteriorated knee and a health knee as opposed to the deteriorated and healthy sides of the same knee, reference information (e.g., vectors, lines, planes, ellipses, etc. as discussed with respect to FIGS. 2-6D) 720 is obtained from a healthy side of the healthy left knee 704 [block 1000 of FIG. 10B]. The reference information 720 obtained from the image slices 16 of the health left knee 704 is applied to the deteriorated sides of the right knee 702 [block 1005 of FIG. 10B]. Specifically, the applied reference information 720 is used to modify the contour lines of the images slices 16 of the deteriorated sides of the right knee 702, after which the modified contour lines are compiled, resulting in a restored bone model 28 that may be employed as described with respect to FIG. 1C. The reference information 720 obtained from the healthy left knee image slices 16 may be coordinated with respect to position and orientation with the contour lines of the deteriorated right knee image slices 16 by identifying a similar location or feature on each knee joint that is generally identical between the knees and free of bone deterioration, such as a point or axis of the femur trochlear groove or tibia plateau spine.

In the second embodiment, image slices 16 are generated of both the deteriorate right knee 702 and healthy left knee 704 as discussed above with respect to FIG. 1B. The image slices 16 of the deteriorated right knee 702 may be used to generate the arthritic model 36 as discussed above with respect to FIG. 1D. The image slices 16 of the healthy left knee 704 are mirrored medially/laterally to reverse the order of the image slices 16 [block 2000 of FIG. 10B]. The mirrored/reversed order image slices 16 of the healthy left knee 704 are compiled, resulting in a restored bone model 28 for the right knee 702 that is formed from the image slices 16 of the left knee 704 [block 2000 of FIG. 10B]. In other words, as can be understood from [block 2000] and its associated pictures in FIG. 10B, by medially/laterally mirroring the image slices 16 of left knee 704 to medially/laterally reverse their order and then compiling them in such a reversed order, the image slices 16 of the left knee 704 may be formed into a bone model that would appear to be a bone model of the right knee 702 in a restored condition, assuming the right and left knees 702, 704 were generally symmetrically identical mirror images of each other when both were in a non-deteriorated state.

To allow for the merger of information (e.g., saw cut and drill hole data 44 and jig data 46) determined respectively from the restored bone model 28 and the arthritic model 28 as discussed above with respect to FIG. 1E, the restored bone model 28 generated from the mirrored image slices 16 of the healthy left knee 704 may be coordinated with respect to position and orientation with the arthritic model 36 generated from the image slices 16 of the deteriorated right knee 702. In one embodiment, this coordination between the models 28, 36 may be achieved by identifying a similar location or feature on each knee joint that is generally identical between the knees and free of bone deterioration, such as a point or axis of the femur trochlear groove or tibia plateau spine. Such a point may serve as the coordination or reference point P' $(X_{0-k}, Y_{0-k}, Z_{0-k})$ as discussed with respect to FIG. 1E.

While the two immediately preceding embodiments are discussed in the context of knee joints, these embodiments, like the rest of the embodiments disclosed throughout this Detailed Description, are readily applicable to other types of joints including ankle joints, hip joints, wrist joints, elbow joints, shoulder joints, finger joints, toe joints, etc., and vertebrae/vertebrae interfaces and vertebrae/skull interfaces. Consequently, the content of this Detailed Description should not be interpreted as being limited to knees, but should be consider to encompass all types of joints and bone interfaces, without limitation.

Although the present invention has been described with reference to preferred embodiments, persons skilled in the art will recognize that changes may be made in form and detail without departing from the spirit and scope of the invention.

The invention claimed is:

1. A method of planning and performing an arthroplasty of a knee joint that has assumed a degenerated state, the arthroplasty being planned to achieve a post-surgical alignment of the knee joint that is a natural alignment of the knee joint that hypothetically existed prior to the knee joint assuming the degenerated state, the method comprising:

accessing on a computer degenerated image data of a first bone of the knee joint, the degenerated image data reflecting the first bone in the degenerated state, the degenerated image data including a degenerated portion and a reference portion, the degenerated portion representing a degenerated condyle of the first bone, the reference portion representing a reference condyle of the first bone, the degenerated condyle being more degenerated than the reference condyle;

modifying with the computer the degenerated image data by adjusting the degenerated portion in view of the reference portion, the modifying of the degenerated image data resulting in restored image data of the first bone, the restored image data reflecting the first bone in a less degenerated state as compared to the degenerated image data reflecting the first bone in the degenerated state;

generating with the computer a three-dimensional restored bone model from the restored image data of the first bone, the three-dimensional restored bone model reflecting the first bone in the less degenerated state;

computer defining a resection of the first bone that allows a prosthetic implanted on the first bone to achieve the post-surgical alignment of the knee joint that is the natural alignment, the computer defining including aligning condylar surfaces of a computer model of the prosthetic with corresponding surfaces of the three-dimensional restored bone model reflecting the first bone in the less degenerated state;

computer referencing with respect to location and orientation in a three dimensional computer coordinate system the defined resection with a registration surface defined on a degenerated computer model of the first bone in the degenerated state, the degenerated computer model of the first bone including, or being a product of, the degenerated image data; and contacting the first bone of the knee joint at a location corresponding to the registration surface and resecting the bone according to the defined resection, the contacting registering the defined resection with the first bone.

2. The method of claim 1, wherein the computer defining further includes superimposing the computer model of the prosthetic and the three-dimensional restored bone model reflecting the first bone in the less degenerated state.

3. A method of planning and performing an arthroplasty of a knee joint that has assumed a degenerated state, the arthroplasty being planned to achieve a post-surgical alignment of the knee joint that is a natural alignment of the knee joint that hypothetically existed prior to the knee joint assuming the degenerated state, the method comprising:

accessing on a computer degenerated image data of a first bone of the knee joint, the degenerated image data reflecting the first bone in the degenerated state, the degenerated image data including a degenerated portion and a reference portion, the degenerated portion representing a degenerated condyle of the first bone, the reference portion representing a reference condyle of the first bone, the degenerated condyle being more degenerated than the reference condyle;

modifying with the computer the degenerated image data by adjusting the degenerated portion in view of the reference portion, the modifying of the degenerated image data resulting in restored image data of the first bone, the restored image data reflecting the first bone in a less degenerated state as compared to the degenerated image data reflecting the first bone in the degenerated state;

generating with the computer a three-dimensional restored bone model from the restored image data of the first bone, the three-dimensional restored bone model reflecting the first bone in the less degenerated state;

defining a resection of the first bone that allows a prosthetic implanted on the first bone to achieve the post-surgical alignment of the knee joint that is the natural alignment, the computer defining including superimposing a computer model of the prosthetic and the three-dimensional restored bone model reflecting the first bone in the less degenerated state;

computer referencing with respect to location and orientation in a three dimensional computer coordinate system the defined resection with a registration surface defined on a degenerated computer model of the first bone in the degenerated state, the degenerated computer model of the first bone including, or being a product of, the degenerated image data; and contacting the first bone of the knee joint at a location corresponding to the registration surface and resecting the bone according to the defined resection, the contacting registering the defined resection with the first bone.

4. A method of manufacturing a custom arthroplasty jig for use in an arthroplasty of a knee joint that has assumed a degenerated state, the arthroplasty being planned to achieve a post-surgical alignment of the knee joint that is a natural alignment of the knee joint that hypothetically existed prior to the knee joint assuming the degenerated state, the method comprising:

accessing on a computer degenerated image data of a first bone of the knee joint, the degenerated image data reflecting the first bone in the degenerated state, the degenerated image data including a degenerated portion and a reference portion, the degenerated portion representing a degenerated condyle of the first bone, the reference portion representing a reference condyle of the first bone, the degenerated condyle being more degenerated than the reference condyle;

modifying with the computer the degenerated image data by adjusting the degenerated portion in view of the reference portion, the modifying of the degenerated image data resulting in restored image data of the first bone, the restored image data reflecting the first bone in a less degenerated state as compared to the degenerated image data reflecting the first bone in the degenerated state;

generating with the computer a three-dimensional restored bone model from the restored image data of the first bone, the three-dimensional restored bone model reflecting the first bone in the less degenerated state;

computer defining a resection of the first bone that allows a prosthetic implanted on the first bone to achieve the post-surgical alignment of the knee joint that is the natural alignment, the computer defining including aligning condylar surfaces of a computer model of the prosthetic with corresponding surfaces of the three-dimensional restored bone model reflecting the first bone in the less degenerated state;

computer referencing with respect to location and orientation in a three dimensional computer coordinate system the defined resection with a registration surface defined on a degenerated computer model of the first bone in the degenerated state, the degenerated computer model of the first bone including, or being a product of, the degenerated image data; and manufacturing the custom arthroplasty jig to have a resection guide and a custom mating surface defined according to the resection and the registration surface, respectively.

5. The method of claim 1, wherein the reference portion of the degenerated image data includes a condyle contour of the reference condyle and the degenerated portion of the degenerated image data includes a condyle contour of the degenerated condyle.

6. The method of claim 5, wherein computer modifying the degenerated image data by adjusting the degenerated portion in view of the reference portion includes: determining a reference vector from the condyle contour of the reference condyle; applying the reference vector to the condyle contour of the degenerated condyle; and causing the condyle contour of the degenerated condyle to extend to the reference vector.

7. The method of claim 6, wherein the reference vector is associated with a femoral condyle ellipse of the condyle contour of the reference condyle.

8. The method of claim 7, wherein the femoral condyle ellipse is determined via a femoral sagittal image slice taken near a femoral condyle point that is at least one of the most distal femoral condylar contact point when the knee joint is in zero degree extension or the most posterior femoral condylar point when the knee joint is in 90 degree extension.

9. The method of claim 8, wherein the reference vector corresponds to the major axis of the femoral condyle ellipse.

10. The method of claim 6, wherein the reference vector is associated with highest tibial anterior and posterior points of the condyle contour of the reference condyle.

11. The method of claim 6, further comprising verify an accuracy of modifying the degenerated image data by comparing an axis extending along a trochlear groove of the restored image data to a joint line of the restored image data.

12. The method of claim 11, wherein the accuracy is acceptable wherein the axis extending along the trochlear groove and the joint line are within approximately six degrees of being perpendicular.

13. The method of claim 1, wherein the degenerated image data includes image contour lines determined from MRI or CT images taken of the first bone.

14. The method of claim 1, wherein the restored image data includes two-dimensional contour lines.

* * * * *